US012784907B2

(12) United States Patent
Rohlwing et al.

(10) Patent No.: US 12,784,907 B2
(45) Date of Patent: Nov. 3, 2026

(54) AUTOMATED INFUSION PUMP UPDATING

(71) Applicant: ICU Medical, Inc., San Clemente, CA (US)

(72) Inventors: Mark C. Rohlwing, Mesa, AZ (US); Michael Niemotka, Mundelein, IL (US); Robert P. Cousineau, Boston, MA (US); James R. Shults, Ramona, CA (US); Nursel Asikhan-Berlinguette, San Clemente, CA (US); Rahul Ashok, Chennai (IN)

(73) Assignee: ICU Medical, Inc., San Clemente, CA (US)

( * ) Notice: Subject to any disclaimer, the term of this patent is extended or adjusted under 35 U.S.C. 154(b) by 198 days.

(21) Appl. No.: 18/187,521

(22) Filed: Mar. 21, 2023

(65) Prior Publication Data

US 2024/0071609 A1 Feb. 29, 2024

Related U.S. Application Data

(63) Continuation of application No. PCT/US2023/062752, filed on Feb. 16, 2023.

(30) Foreign Application Priority Data

Feb. 18, 2022 (IN) ............................. 202211008675

(51) Int. Cl.
*G16H 40/40* (2018.01)
*G16H 20/17* (2018.01)
(Continued)

(52) U.S. Cl.
CPC ............. *G16H 40/40* (2018.01); *G16H 20/17* (2018.01); *G16H 40/67* (2018.01); *G16H 70/40* (2018.01)

(58) Field of Classification Search
None
See application file for complete search history.

(56) References Cited

U.S. PATENT DOCUMENTS

| | | | |
|---|---|---|---|
| 4,024,864 | A | 5/1977 | Davies et al. |
| 4,055,175 | A | 10/1977 | Clemens et al. |

(Continued)

FOREIGN PATENT DOCUMENTS

| | | |
|---|---|---|
| AU | 2004226440 | 10/2004 |
| AU | 2004305087 | 7/2005 |

(Continued)

OTHER PUBLICATIONS

Marinkovic et al., Ultra Low Power Signal Oriented Approach for Wireless Health Monitoring, Sensors 2012, 12, 7917-7937; doi: 10.3390/s120607917.*

(Continued)

*Primary Examiner* — Kambiz Abdi
(74) *Attorney, Agent, or Firm* — Knobbe, Martens, Olson & Bear, LLP

(57) ABSTRACT

An infusion pump configured to automatically determine whether to receive an update comprises a battery, a processor, communication engine, a memory, and a clock. The processor is configured to receive power from the battery. The communication is in communication with the processor and configured to communicate with a remote location. The memory is in communication with the processor and stores instructions. When executed by the processor, the instructions configure the processor to wake the processor from an off state, determine that the infusion pump is receiving electrical power from the battery, and determine whether the battery contains sufficient energy to complete an update to the infusion pump. In response to determining that the battery contains sufficient energy, the instructions further configure the processor to wake the communication engine (Continued)

from an off to determine whether the update is available to be acquired from the remote location.

20 Claims, 18 Drawing Sheets

(51) Int. Cl.
*G16H 40/67* (2018.01)
*G16H 70/40* (2018.01)

(56) References Cited

U.S. PATENT DOCUMENTS

| | | | |
|---|---|---|---|
| 4,151,845 | A | 5/1979 | Clemens |
| 4,213,454 | A | 7/1980 | Shim |
| 4,240,438 | A | 12/1980 | Updike et al. |
| 4,280,494 | A | 7/1981 | Cosgrove et al. |
| 4,308,866 | A | 1/1982 | Jeliffe |
| 4,370,983 | A | 2/1983 | Lichtenstein et al. |
| 4,373,527 | A | 2/1983 | Fischell |
| 4,392,849 | A | 7/1983 | Petre et al. |
| 4,395,259 | A | 7/1983 | Prestele et al. |
| 4,457,751 | A | 7/1984 | Rodler |
| 4,464,170 | A | 8/1984 | Clemens |
| 4,469,481 | A | 9/1984 | Kobayashi |
| 4,475,901 | A | 10/1984 | Kraegen et al. |
| 4,494,950 | A | 1/1985 | Fischell |
| 4,498,843 | A | 2/1985 | Schneider et al. |
| 4,515,584 | A | 5/1985 | Abe et al. |
| 4,526,568 | A | 7/1985 | Clemens et al. |
| 4,529,401 | A | 7/1985 | Leslie et al. |
| 4,543,955 | A | 10/1985 | Schroeppel |
| 4,551,133 | A | 11/1985 | Zegers de Beyl et al. |
| 4,553,958 | A | 11/1985 | LeCocq |
| 4,559,037 | A | 12/1985 | Franetzki et al. |
| 4,613,937 | A | 9/1986 | Batty |
| 4,624,661 | A | 11/1986 | Arimond |
| 4,633,878 | A | 1/1987 | Bombardieri |
| 4,634,426 | A | 1/1987 | Kamen |
| 4,634,427 | A | 1/1987 | Hannula et al. |
| 4,674,652 | A | 6/1987 | Aten et al. |
| 4,676,776 | A | 6/1987 | Howson et al. |
| 4,679,562 | A | 7/1987 | Luksha |
| 4,685,903 | A | 8/1987 | Cable et al. |
| 4,695,954 | A | 9/1987 | Rose |
| 4,696,671 | A | 9/1987 | Epstein et al. |
| 4,714,462 | A | 12/1987 | DiDomenico |
| 4,722,734 | A | 2/1988 | Kolin |
| 4,730,849 | A | 3/1988 | Siegel |
| 4,731,051 | A | 3/1988 | Fischell |
| 4,741,732 | A | 5/1988 | Crankshaw et al. |
| 4,756,706 | A | 7/1988 | Kerns et al. |
| 4,776,842 | A | 10/1988 | Franetzki et al. |
| 4,785,969 | A | 11/1988 | Mclaughlin |
| 4,803,625 | A | 2/1989 | Fu et al. |
| 4,835,372 | A | 5/1989 | Gombrich et al. |
| 4,838,275 | A | 6/1989 | Lee |
| 4,838,856 | A | 6/1989 | Mulreany et al. |
| 4,838,857 | A | 6/1989 | Strowe et al. |
| 4,854,324 | A | 8/1989 | Hirschman et al. |
| 4,857,716 | A | 8/1989 | Gombrich et al. |
| 4,858,154 | A | 8/1989 | Anderson et al. |
| 4,898,578 | A | 2/1990 | Rubalcaba, Jr. |
| 4,908,017 | A | 3/1990 | Howson et al. |
| 4,933,873 | A | 6/1990 | Kaufman et al. |
| 4,943,279 | A | 7/1990 | Samiotes et al. |
| 4,946,439 | A | 8/1990 | Eggers |
| 4,953,745 | A | 9/1990 | Rowlett |
| 4,978,335 | A | 12/1990 | Arthur, III |
| 5,000,739 | A | 3/1991 | Kulisz et al. |
| 5,010,473 | A | 4/1991 | Jacobs |
| 5,014,698 | A | 5/1991 | Cohen |
| 5,016,172 | A | 5/1991 | Dessertine |
| 5,026,084 | A | 6/1991 | Paisfield |
| 5,034,004 | A | 7/1991 | Crankshaw |
| 5,041,086 | A | 8/1991 | Koenig et al. |
| 5,058,161 | A | 10/1991 | Weiss |
| 5,078,683 | A | 1/1992 | Sancoff et al. |
| 5,084,828 | A | 1/1992 | Kaufman et al. |
| 5,088,981 | A | 2/1992 | Howson et al. |
| 5,097,505 | A | 3/1992 | Weiss |
| 5,100,380 | A | 3/1992 | Epstein et al. |
| 5,102,392 | A | 4/1992 | Sakai et al. |
| 5,104,374 | A | 4/1992 | Bishko et al. |
| 5,109,850 | A | 5/1992 | Blanco et al. |
| 5,131,816 | A | 7/1992 | Brown |
| 5,142,484 | A | 8/1992 | Kaufman et al. |
| 5,153,827 | A | 10/1992 | Coutre et al. |
| 5,157,640 | A | 10/1992 | Backner |
| 5,161,222 | A | 11/1992 | Montejo et al. |
| 5,177,993 | A | 1/1993 | Beckman et al. |
| 5,181,910 | A | 1/1993 | Scanlon |
| 5,190,522 | A | 3/1993 | Wocicki et al. |
| 5,199,439 | A | 4/1993 | Zimmerman et al. |
| 5,200,891 | A | 4/1993 | Kehr et al. |
| 5,216,597 | A | 6/1993 | Beckers |
| 5,221,268 | A | 6/1993 | Barton et al. |
| 5,230,061 | A | 7/1993 | Welch |
| 5,243,982 | A | 9/1993 | Möstl et al. |
| 5,244,463 | A | 9/1993 | Cordner, Jr. et al. |
| 5,249,260 | A | 9/1993 | Nigawara et al. |
| 5,254,096 | A | 10/1993 | Rondelet et al. |
| 5,256,156 | A | 10/1993 | Kern et al. |
| 5,256,157 | A | 10/1993 | Samiotes et al. |
| 5,261,702 | A | 11/1993 | Mayfield |
| 5,317,506 | A | 5/1994 | Coutre et al. |
| 5,319,355 | A | 6/1994 | Russek |
| 5,319,363 | A | 6/1994 | Welch et al. |
| 5,330,634 | A | 7/1994 | Wong et al. |
| 5,338,157 | A | 8/1994 | Blomquist |
| 5,341,476 | A | 8/1994 | Lowell |
| 5,364,346 | A | 11/1994 | Schrezenmeir |
| 5,366,346 | A | 11/1994 | Danby |
| 5,368,562 | A | 11/1994 | Blomquist et al. |
| 5,373,454 | A | 12/1994 | Kanda et al. |
| 5,376,070 | A | 12/1994 | Purvis et al. |
| 5,378,231 | A | 1/1995 | Johnson et al. |
| 5,389,071 | A | 2/1995 | Kawahara et al. |
| 5,389,078 | A | 2/1995 | Zalesky et al. |
| 5,417,222 | A | 5/1995 | Dempsey et al. |
| 5,423,748 | A | 6/1995 | Uhala |
| 5,429,602 | A | 7/1995 | Hauser |
| 5,431,627 | A | 7/1995 | Pastrone et al. |
| 5,432,777 | A | 7/1995 | Le Boudec et al. |
| 5,445,621 | A | 8/1995 | Poli et al. |
| 5,447,164 | A | 9/1995 | Shaya et al. |
| 5,455,851 | A | 10/1995 | Chaco et al. |
| 5,461,365 | A | 10/1995 | Schlager et al. |
| 5,464,392 | A | 11/1995 | Epstein et al. |
| 5,465,082 | A | 11/1995 | Chaco |
| 5,485,408 | A | 1/1996 | Blomquist |
| 5,486,286 | A | 1/1996 | Peterson et al. |
| 5,493,430 | A | 2/1996 | Lu et al. |
| 5,496,273 | A | 3/1996 | Pastrone et al. |
| 5,505,828 | A | 4/1996 | Wong et al. |
| 5,507,288 | A | 4/1996 | Bocker et al. |
| 5,507,786 | A | 4/1996 | Morgan et al. |
| 5,508,499 | A | 4/1996 | Ferrario |
| 5,515,713 | A | 5/1996 | Saugues et al. |
| 5,520,637 | A | 5/1996 | Pager et al. |
| 5,522,798 | A | 6/1996 | Johnson et al. |
| 5,547,470 | A | 8/1996 | Johnson et al. |
| 5,554,013 | A | 9/1996 | Owens et al. |
| 5,562,615 | A | 10/1996 | Nassif |
| 5,577,169 | A | 11/1996 | Prezioso |
| 5,582,323 | A | 12/1996 | Kurtenbach |
| 5,582,593 | A | 12/1996 | Hultman |
| 5,594,786 | A | 1/1997 | Chaco et al. |
| 5,598,519 | A | 1/1997 | Narayanan |
| 5,620,608 | A | 4/1997 | Rosa et al. |
| 5,630,710 | A | 5/1997 | Tune et al. |
| 5,636,044 | A | 6/1997 | Yuan et al. |
| 5,643,212 | A | 7/1997 | Coutre et al. |
| 5,651,775 | A | 7/1997 | Walker et al. |

(56) References Cited

U.S. PATENT DOCUMENTS 5,658,131 A 8/1997 Aoki et al.
5,658,250 A 8/1997 Blomquist et al.
5,665,065 A 9/1997 Colman et al.
5,669,877 A 9/1997 Blomquist
5,672,154 A 9/1997 Sillén et al.
5,681,285 A 10/1997 Ford et al.
5,685,844 A 11/1997 Marttila
5,687,717 A 11/1997 Halpern et al.
5,689,229 A 11/1997 Chaco et al.
5,697,899 A 12/1997 Hillman et al.
5,699,509 A 12/1997 Gary et al.
5,708,714 A 1/1998 Lopez et al.
5,713,350 A 2/1998 Yokota et al.
5,713,856 A 2/1998 Eggers et al.
5,718,562 A 2/1998 Lawless et al.
5,719,761 A 2/1998 Gatti et al.
5,733,259 A 3/1998 Valcke et al.
5,738,102 A 4/1998 Lemelson
5,744,027 A 4/1998 Connell et al.
5,752,621 A 5/1998 Passamante
5,754,111 A 5/1998 Garcia
5,764,034 A 6/1998 Bowman et al.
5,764,159 A 6/1998 Neftel et al.
5,772,635 A 6/1998 Dastur et al.
5,774,865 A 6/1998 Glynn
5,778,256 A 7/1998 Darbee
5,778,345 A 7/1998 McCartney
5,781,442 A 7/1998 Engleson et al.
5,782,805 A 7/1998 Meinzer et al.
5,788,669 A 8/1998 Peterson
5,797,515 A 8/1998 Liff et al.
5,800,387 A 9/1998 Duffy et al.
5,814,015 A 9/1998 Gargano et al.
5,822,544 A 10/1998 Chaco et al.
5,822,715 A 10/1998 Worthington et al.
5,827,179 A 10/1998 Lichter et al.
5,832,448 A 11/1998 Brown
5,836,910 A 11/1998 Duffy et al.
5,850,344 A 12/1998 Conkright
5,867,821 A 2/1999 Ballantyne et al.
5,870,733 A 2/1999 Bass et al.
5,871,465 A 2/1999 Vasko
5,873,731 A 2/1999 Predergast
5,885,245 A 3/1999 Lynch et al.
5,897,493 A 4/1999 Brown
5,897,498 A 4/1999 Canfield et al.
5,910,252 A 6/1999 Truitt et al.
5,912,818 A 6/1999 McGrady et al.
5,915,240 A 6/1999 Karpf
5,920,054 A 7/1999 Uber, III
5,920,263 A 7/1999 Huttenhoff et al.
5,924,074 A 7/1999 Evans
5,931,764 A 8/1999 Freeman et al.
5,935,099 A 8/1999 Peterson et al.
5,935,106 A 8/1999 Olsen
5,941,846 A 8/1999 Duffy et al.
5,956,501 A 9/1999 Brown
5,957,885 A 9/1999 Bollish et al.
5,960,085 A 9/1999 de la Huerga
5,961,448 A 10/1999 Swenson et al.
5,967,559 A 10/1999 Abramowitz
5,971,594 A 10/1999 Sahai et al.
5,975,081 A 11/1999 Hood et al.
5,990,838 A 11/1999 Burns et al.
5,997,476 A 12/1999 Brown
6,000,828 A 12/1999 Leet
6,003,006 A 12/1999 Colella et al.
6,012,034 A 1/2000 Hamparian et al.
6,017,318 A 1/2000 Gauthier et al.
6,021,392 A 2/2000 Lester et al.
6,024,539 A 2/2000 Blomquist
6,024,699 A 2/2000 Surwit et al.
6,032,155 A 2/2000 de la Huerga
6,032,676 A 3/2000 Moore
6,039,251 A 3/2000 Holowko et al.
6,070,761 A 6/2000 Bloom et al.
6,073,106 A 6/2000 Rozen et al.
6,104,295 A 8/2000 Gaisser et al.
6,112,182 A 8/2000 Akers et al.
6,112,323 A 8/2000 Meizlik et al.
RE36,871 E 9/2000 Epstein et al.
6,115,365 A 9/2000 Newberg
6,115,390 A 9/2000 Chuah
6,122,536 A 9/2000 Sun et al.
6,126,637 A 10/2000 Kriesel et al.
6,135,949 A 10/2000 Russo et al.
6,150,942 A 11/2000 O'Brien
6,151,643 A 11/2000 Cheng et al.
6,157,914 A 12/2000 Seto et al.
6,159,147 A 12/2000 Lichter et al.
6,167,567 A 12/2000 Chiles et al.
6,182,667 B1 2/2001 Hanks et al.
6,189,105 B1 2/2001 Lopes
6,195,589 B1 2/2001 Ketcham
6,208,974 B1 3/2001 Campbell et al.
6,222,323 B1 4/2001 Yamashita et al.
6,223,440 B1 5/2001 Rashman
6,226,277 B1 5/2001 Chuah
6,227,371 B1 5/2001 Song
6,234,176 B1 5/2001 Domae et al.
6,241,704 B1 6/2001 Peterson et al.
6,248,067 B1 6/2001 Causey, III et al.
6,249,705 B1 6/2001 Snell
6,257,265 B1 7/2001 Brunner et al.
6,259,355 B1 7/2001 Chaco et al.
6,269,340 B1 7/2001 Ford et al.
6,270,455 B1 8/2001 Brown
6,271,813 B1 8/2001 Palalau
6,277,072 B1 8/2001 Bardy
6,280,380 B1 8/2001 Bardy
6,283,761 B1 9/2001 Joao
6,285,665 B1 9/2001 Chuah
6,292,860 B1 9/2001 Cochcroft, Jr.
6,312,378 B1 11/2001 Bardy
6,327,254 B1 12/2001 Chuah
6,330,008 B1 12/2001 Razdow et al.
6,339,718 B1 1/2002 Zatezalo et al.
6,346,886 B1 2/2002 de la Huerga
6,363,282 B1 3/2002 Nichols et al.
6,371,719 B1 4/2002 Hildebrandt
6,377,548 B1 4/2002 Chuah
6,388,951 B1 5/2002 Matsumoto et al.
6,406,426 B1 6/2002 Reuss et al.
6,408,330 B1 6/2002 de la Huerga
6,418,334 B1 7/2002 Unger et al.
6,427,088 B1 7/2002 Bowman et al.
6,428,483 B1 8/2002 Carlebach
6,442,432 B2 8/2002 Lee
6,469,991 B1 10/2002 Chuah
6,475,180 B2 11/2002 Peterson et al.
6,482,158 B2 11/2002 Mault
6,485,418 B2 11/2002 Yasushi et al.
6,494,694 B2 12/2002 Lawless et al.
6,494,831 B1 12/2002 Koritzinsky
6,497,680 B1 12/2002 Holst et al.
6,514,460 B1 2/2003 Fendrock
6,517,482 B1 2/2003 Eiden et al.
6,519,569 B1 2/2003 White et al.
6,520,930 B2 2/2003 Critchlow et al.
6,540,672 B1 4/2003 Simonsen et al.
6,542,902 B2 4/2003 Dulong et al.
6,544,212 B2 4/2003 Galley et al.
6,544,228 B1 4/2003 Heitmeier
6,546,350 B1 4/2003 Hartmann et al.
6,551,276 B1 4/2003 Mann et al.
6,554,798 B1 4/2003 Mann et al.
6,558,320 B1 5/2003 Causey et al.
6,558,351 B1 5/2003 Steil et al.
6,565,509 B1 5/2003 Say et al.
6,567,416 B1 5/2003 Chuah
6,571,294 B2 5/2003 Simmon et al.
6,572,542 B1 6/2003 Houben et al.
6,572,545 B2 6/2003 Knobbe et al.
6,578,002 B1 6/2003 Derzay et al.

(56) References Cited

U.S. PATENT DOCUMENTS 6,581,117 B1 6/2003 Klein et al.
6,587,034 B1 7/2003 Heiman et al.
6,589,229 B1 7/2003 Connelly et al.
6,599,281 B1 7/2003 Struys et al.
6,602,191 B2 8/2003 Quy
6,605,072 B2 8/2003 Struys et al.
6,628,809 B1 9/2003 Rowe et al.
6,631,353 B1 10/2003 Davis et al.
6,640,246 B1 10/2003 Gardy, Jr. et al.
6,641,533 B2 11/2003 Causey, III et al.
6,647,299 B2 11/2003 Bourget
6,652,455 B1 11/2003 Kocher
6,653,937 B2 11/2003 Nelson et al.
6,659,947 B1 12/2003 Carter et al.
6,669,630 B1 12/2003 Joliat et al.
6,671,563 B1 12/2003 Engleson et al.
6,673,033 B1 1/2004 Sciulli et al.
6,674,403 B2 1/2004 Gray et al.
6,681,003 B2 1/2004 Linder et al.
6,689,091 B2 2/2004 Bui et al.
6,692,241 B2 2/2004 Watanabe et al.
6,694,191 B2 2/2004 Starkweather et al.
6,694,334 B2 2/2004 DuLong et al.
6,721,286 B1 4/2004 Williams et al.
6,721,582 B2 4/2004 Trepagnier et al.
6,725,200 B1 4/2004 Rost
6,731,989 B2 5/2004 Engleson et al.
6,740,072 B2 5/2004 Starkweather et al.
6,751,651 B2 6/2004 Crockett
6,752,787 B1 6/2004 Causey, III et al.
6,753,830 B2 6/2004 Gelbman
6,758,810 B2 7/2004 Lebel et al.
6,773,396 B2 8/2004 Flach et al.
6,774,786 B1 8/2004 Havekost et al.
6,775,577 B2 8/2004 Cmkovich et al.
6,780,156 B2 8/2004 Haueter et al.
6,790,198 B1 9/2004 White et al.
6,792,470 B2 9/2004 Hakenberg et al.
6,796,956 B2 9/2004 Hartlaub et al.
6,799,149 B2 9/2004 Hartlaub
6,809,653 B1 10/2004 Mann et al.
6,811,534 B2 11/2004 Bowman, IV et al.
6,816,605 B2 11/2004 Rowe et al.
6,839,753 B2 1/2005 Biondi et al.
6,852,104 B2 2/2005 Blomquist
6,859,134 B1 2/2005 Heiman et al.
6,871,211 B2 3/2005 Labounty et al.
6,873,268 B2 3/2005 Lebel et al.
6,876,303 B2 4/2005 Reeder et al.
6,885,881 B2 4/2005 Leonhardt
6,891,525 B2 5/2005 Ogoro
6,892,278 B2 5/2005 Ebergen
6,899,695 B2 5/2005 Herrera
6,915,170 B2 7/2005 Engleson et al.
6,923,763 B1 8/2005 Kovatchev et al.
6,924,781 B1 8/2005 Gelbman
6,928,338 B1 8/2005 Buchser et al.
6,928,490 B1 8/2005 Bucholz et al.
6,936,029 B2 8/2005 Mann et al.
6,945,954 B2 9/2005 Hochman et al.
6,948,492 B2 9/2005 Wemeling et al.
6,958,677 B1 10/2005 Carter
6,958,691 B1 10/2005 Anderson et al.
6,958,705 B2 10/2005 Lebel et al.
6,961,448 B2 11/2005 Nichols et al.
6,969,352 B2 11/2005 Chiang et al.
6,969,865 B2 11/2005 Duchon et al.
6,974,437 B2 12/2005 Lebel et al.
6,979,326 B2 12/2005 Mann et al.
6,980,958 B1 12/2005 Surwit et al.
6,985,870 B2 1/2006 Martucci et al.
6,986,347 B2 1/2006 Hickle
6,997,880 B2 2/2006 Carlebach et al.
6,997,920 B2 2/2006 Mann et al.
6,998,984 B1 2/2006 Zittrain
7,016,752 B1 3/2006 Ruben et al.
7,017,293 B2 3/2006 Riley
7,025,743 B2 4/2006 Mann et al.
7,029,455 B2 4/2006 Flaherty
7,038,584 B2 5/2006 Carter
7,060,031 B2 6/2006 Webb et al.
7,060,059 B2 6/2006 Keith et al.
7,069,552 B2 6/2006 Lindberg et al.
7,072,725 B2 7/2006 Bristol et al.
7,079,035 B2 7/2006 Bock et al.
7,092,943 B2 8/2006 Roese et al.
7,096,072 B2 8/2006 Engleson et al.
7,099,809 B2 8/2006 Dori
7,103,419 B2 9/2006 Engleson et al.
7,103,578 B2 9/2006 Beck et al.
7,107,106 B2 9/2006 Engleson et al.
7,108,680 B2 9/2006 Rohr et al.
7,109,878 B2 9/2006 Mann et al.
7,114,002 B1 9/2006 Okumura et al.
7,117,041 B2 10/2006 Engleson et al.
7,136,645 B2 11/2006 Hanson et al.
7,137,964 B2 11/2006 Flaherty
7,142,190 B2 11/2006 Martinez
7,150,741 B2 12/2006 Erickson et al.
7,153,289 B2 12/2006 Vasko
7,154,397 B2 12/2006 Zerhusen et al.
7,156,807 B2 1/2007 Carter et al.
7,158,030 B2 1/2007 Chung
7,161,484 B2 1/2007 Tsoukalis et al.
7,167,755 B2 1/2007 Seeberger et al.
7,167,920 B2 1/2007 Traversat
7,171,277 B2 1/2007 Engleson et al.
7,171,492 B1 1/2007 Borella et al.
7,181,493 B2 2/2007 English et al.
7,185,288 B2 2/2007 Mckeever
7,193,514 B2 3/2007 Ritson
7,197,025 B2 3/2007 Chuah
7,201,734 B2 4/2007 Hickle
7,204,823 B2 4/2007 Estes et al.
7,213,009 B2 5/2007 Pestotnik
7,216,802 B1 5/2007 de la Huerga
7,220,240 B2 5/2007 Struys et al.
7,224,979 B2 5/2007 Singhal et al.
7,229,430 B2 6/2007 Hickle et al.
7,230,529 B2 6/2007 Ketcherside
7,236,936 B2 6/2007 White et al.
7,238,164 B2 7/2007 Childers et al.
7,247,154 B2 7/2007 Hickle
7,248,239 B2 7/2007 Dowling
7,250,856 B2 7/2007 Havekost et al.
7,255,683 B2 8/2007 Vanderveen et al.
7,256,888 B2 8/2007 Staehr et al.
7,258,534 B2 8/2007 Fathallah et al.
7,263,213 B2 8/2007 Rowe
7,267,664 B2 9/2007 Rizzo
7,267,665 B2 9/2007 Steil et al.
7,275,156 B2 9/2007 Balfanz et al.
7,278,983 B2 10/2007 Ireland et al.
7,289,815 B2 10/2007 Gfeller et al.
7,289,948 B1 10/2007 Mohri
7,293,107 B1 11/2007 Hanson et al.
7,295,119 B2 11/2007 Rappaport et al.
7,295,556 B2 11/2007 Roese et al.
7,301,451 B2 11/2007 Hastings
7,308,300 B2 12/2007 Toews et al.
7,315,825 B2 1/2008 Rosenfeld et al.
7,319,386 B2 1/2008 Collins, Jr. et al.
7,324,000 B2 1/2008 Zittrain et al.
7,327,705 B2 2/2008 Fletcher et al.
7,343,224 B2 3/2008 DiGianfilippo et al.
7,346,025 B2 3/2008 Bryson
7,347,836 B2 3/2008 Peterson et al.
7,354,420 B2 4/2008 Steil et al.
7,369,897 B2 5/2008 Boveja et al.
7,369,948 B1 5/2008 Ferenczi et al.
7,383,088 B2 6/2008 Spinelli et al.
7,384,410 B2 6/2008 Eggers et al.
7,398,183 B2 7/2008 Holland et al.
7,398,279 B2 7/2008 Muno, Jr. et al.

(56) References Cited

U.S. PATENT DOCUMENTS 7,399,277 B2 7/2008 Saidara et al.
7,402,153 B2 7/2008 Steil et al.
7,420,472 B2 9/2008 Tran
7,432,807 B2 10/2008 Schmitt
7,436,454 B2 10/2008 Yamaguchi et al.
7,447,643 B1 11/2008 Olson
7,454,314 B2 11/2008 Holland et al.
7,457,804 B2 11/2008 Uber, III et al.
7,464,040 B2 12/2008 Joao
7,469,213 B1 12/2008 Rao
7,471,994 B2 12/2008 Ford et al.
7,483,756 B2 1/2009 Engleson et al.
7,489,808 B2 2/2009 Gerder
7,490,021 B2 2/2009 Holland et al.
7,490,048 B2 2/2009 Joao
7,491,187 B2 2/2009 Van Den Berghe et al.
7,519,905 B2 4/2009 Kougiouris et al.
7,523,401 B1 4/2009 Aldridge
7,524,304 B2 4/2009 Genosar
7,551,078 B2 6/2009 Carlson
7,559,321 B2 7/2009 Wermeling et al.
7,565,197 B2 7/2009 Haulbrich et al.
7,572,230 B2 8/2009 Neumann et al.
7,578,802 B2 8/2009 Hickle
7,621,009 B2 11/2009 Elhabashy
D606,533 S 12/2009 De Jong et al.
7,636,718 B1 12/2009 Steen et al.
7,640,172 B2 12/2009 Kuth
7,645,258 B2 1/2010 White et al.
7,647,237 B2 1/2010 Malave et al.
7,662,124 B2 2/2010 Duchon et al.
7,668,731 B2 2/2010 Martucci et al.
7,671,733 B2 3/2010 McNeal et al.
7,678,071 B2 3/2010 Lebel et al.
7,687,678 B2 3/2010 Jacobs
7,697,994 B2 4/2010 VanDanacker et al.
7,698,239 B2 4/2010 Lieuallen
7,705,727 B2 4/2010 Pestotnik
7,724,147 B2 5/2010 Brown et al.
7,739,126 B1 6/2010 Cave
7,746,218 B2 6/2010 Collins, Jr.
7,766,873 B2 8/2010 Moberg et al.
7,776,029 B2 8/2010 Whitehurst et al.
7,776,031 B2 8/2010 Hartlaub et al.
7,785,313 B2 8/2010 Mastrototaro
7,788,369 B2 8/2010 McAllen et al.
7,806,852 B1 10/2010 Jurson
7,806,886 B2 10/2010 Kanderian, Jr. et al.
7,826,981 B2 11/2010 Goode, Jr. et al.
7,835,927 B2 11/2010 Schlotterbeck et al.
7,836,314 B2 11/2010 Chieu
7,856,276 B2 12/2010 Ripart et al.
7,860,583 B2 12/2010 Condurso et al.
7,864,771 B2 1/2011 Tavares et al.
7,868,754 B2 1/2011 Salvat, Jr.
7,871,394 B2 1/2011 Halbert et al.
7,886,231 B2 2/2011 Hopermann et al.
7,895,053 B2 2/2011 Holland et al.
7,896,842 B2 3/2011 Palmroos et al.
7,899,546 B2 3/2011 Sieracki et al.
7,905,710 B2 3/2011 Wang et al.
7,920,061 B2 4/2011 Klein et al.
7,933,780 B2 4/2011 de la Huerga
7,938,796 B2 5/2011 Moubayed
7,945,452 B2 5/2011 Fathallah et al.
7,974,714 B2 7/2011 Hoffberg
7,976,508 B2 7/2011 Hoag
7,996,241 B2 8/2011 Zak
8,034,026 B2 10/2011 Grant
8,038,593 B2 10/2011 Friedman et al.
8,048,040 B2 11/2011 Kiani
8,060,576 B2 11/2011 Chan et al.
8,065,161 B2 11/2011 Howard et al.
8,066,672 B2 11/2011 Mandro
8,075,514 B2 12/2011 Butterfield et al.
8,078,983 B2 12/2011 Davis et al.
8,082,018 B2 12/2011 Duchon et al.
8,082,312 B2 12/2011 Chan et al.
8,095,692 B2 1/2012 Mehta et al.
8,126,730 B2 2/2012 Dicks et al.
8,147,448 B2 4/2012 Sundar et al.
8,149,131 B2 4/2012 Blomquist
8,169,914 B2 5/2012 Bajpai
8,171,094 B2 5/2012 Chan et al.
8,172,798 B2 5/2012 Hungerford et al.
8,185,322 B2 5/2012 Schroeder et al.
8,195,478 B2 6/2012 Petersen et al.
8,206,350 B2 6/2012 Mann et al.
8,219,413 B2 7/2012 Martinez et al.
8,231,578 B2 7/2012 Fathallah et al.
8,234,128 B2 7/2012 Martucci et al.
8,267,892 B2 9/2012 Spencer et al.
8,271,106 B2 9/2012 Wehba et al.
8,287,495 B2 10/2012 Michaud et al.
8,291,337 B2 10/2012 Gannin et al.
8,298,184 B2 10/2012 DiPerna et al.
8,312,272 B1 11/2012 Serenyl et al.
8,352,290 B2 1/2013 Bartz et al.
8,359,338 B2 1/2013 Butterfield et al.
8,380,536 B2 * 2/2013 Howard ................ A61M 5/142
705/2
8,387,112 B1 2/2013 Ranjan et al.
8,394,077 B2 3/2013 Jacobson et al.
8,398,592 B2 3/2013 Leibner-Druska
8,403,908 B2 3/2013 Jacobson et al.
8,435,206 B2 5/2013 Evans et al.
8,449,523 B2 5/2013 Brukalo et al.
8,452,953 B2 5/2013 Buck et al.
8,453,645 B2 6/2013 Figueiredo et al.
8,472,630 B2 6/2013 Konrad et al.
8,480,648 B2 7/2013 Burnett et al.
8,486,019 B2 7/2013 White et al.
8,489,427 B2 7/2013 Simpson et al.
8,494,879 B2 7/2013 Davis et al.
8,504,179 B2 8/2013 Blomquist
8,517,990 B2 8/2013 Teel et al.
8,518,021 B2 8/2013 Stewart et al.
8,543,416 B2 9/2013 Palmroos et al.
8,551,038 B2 10/2013 Tsoukalis et al.
8,560,345 B2 10/2013 Wehba et al.
8,567,681 B2 10/2013 Borges et al.
8,577,692 B2 11/2013 Silkaitis et al.
8,579,884 B2 11/2013 Lanier et al.
8,626,530 B1 1/2014 Tran et al.
8,655,676 B2 2/2014 Wehba et al.
8,660,860 B2 2/2014 Wehba et al.
8,662,388 B2 3/2014 Belkin
8,666,769 B2 3/2014 Butler et al.
8,667,293 B2 3/2014 Birtwhistle et al.
8,687,811 B2 4/2014 Nierzwick et al.
8,700,421 B2 4/2014 Feng et al.
8,731,960 B2 5/2014 Butler et al.
8,768,719 B2 7/2014 Wehba et al.
8,771,251 B2 7/2014 Ruchti et al.
8,777,894 B2 7/2014 Butterfield et al.
8,777,895 B2 7/2014 Hsu et al.
8,799,012 B2 8/2014 Butler et al.
8,876,793 B2 11/2014 Ledford et al.
8,886,316 B1 11/2014 Juels
8,922,330 B2 12/2014 Moberg et al.
8,936,565 B2 1/2015 Chawla
8,945,043 B2 2/2015 Lee et al.
8,952,794 B2 2/2015 Blomquist et al.
8,959,617 B2 2/2015 Newlin et al.
8,998,100 B2 4/2015 Halbert et al.
9,026,370 B2 5/2015 Rubalcaba et al.
9,069,887 B2 6/2015 Gupta et al.
9,077,544 B2 7/2015 Baker et al.
9,089,642 B2 7/2015 Murphy et al.
9,114,217 B2 8/2015 Sur et al.
9,123,077 B2 9/2015 Silkaitis et al.
9,192,712 B2 11/2015 DeBelser et al.
9,240,002 B2 1/2016 Hume et al.
9,283,339 B2 3/2016 Sherman

(56) References Cited

U.S. PATENT DOCUMENTS 9,292,692 B2 3/2016 Wallrabenstein
9,302,035 B2 4/2016 Marseille et al.
9,313,154 B1 4/2016 Son
9,381,296 B2 7/2016 Arrizza et al.
9,393,362 B2 7/2016 Cozmi et al.
9,430,655 B1 8/2016 Stockton et al.
9,438,580 B2 9/2016 Kupper
9,483,615 B2 11/2016 Roberts
9,498,583 B2 11/2016 Sur et al.
9,539,383 B2 1/2017 Kohlbrecher
9,572,923 B2 2/2017 Howard et al.
9,594,875 B2 3/2017 Arrizza et al.
9,604,000 B2 3/2017 Wehba et al.
9,641,432 B2 5/2017 Jha et al.
9,649,431 B2 5/2017 Gray et al.
9,662,436 B2 5/2017 Belkin et al.
9,690,909 B2 6/2017 Stewart et al.
9,707,341 B2 7/2017 Dumas, III et al.
9,717,845 B2 8/2017 Istoc
9,724,470 B2 8/2017 Day et al.
9,729,330 B2 8/2017 Verma
9,764,082 B2 9/2017 Day et al.
9,886,550 B2 2/2018 Lee et al.
9,904,765 B2 2/2018 Borges
9,943,269 B2 4/2018 Muhsin et al.
9,967,739 B2 5/2018 Proennecke et al.
9,971,871 B2 5/2018 Arrizza et al.
9,980,140 B1 5/2018 Spencer et al.
9,995,611 B2 6/2018 Ruchti et al.
10,022,498 B2 7/2018 Ruchti et al.
10,042,986 B2 8/2018 Ruchti et al.
10,046,112 B2 8/2018 Oruklu et al.
10,166,328 B2 1/2019 Oruklu et al.
10,173,008 B2 1/2019 Simpson et al.
10,188,849 B2 1/2019 Fangrow
10,233,179 B2 3/2019 Ng et al.
10,238,799 B2 3/2019 Kohlbrecher
10,238,801 B2 3/2019 Wehba et al.
10,242,060 B2 3/2019 Butler et al.
10,300,194 B2 5/2019 Day et al.
10,311,972 B2 6/2019 Kohlbrecher et al.
10,314,974 B2 6/2019 Day et al.
10,333,843 B2 6/2019 Jha et al.
10,341,866 B1 7/2019 Spencer et al.
10,356,087 B1 7/2019 Vetter
10,366,210 B2 * 7/2019 Moskal .................. G16H 40/40
10,409,995 B1 9/2019 Wasiq
10,430,761 B2 10/2019 Hume et al.
10,434,246 B2 10/2019 Silkaitis et al.
10,438,001 B1 10/2019 Hariprasad
10,452,842 B2 10/2019 Dhondse
10,453,157 B2 10/2019 Kamen et al.
10,463,788 B2 11/2019 Day
10,516,536 B2 12/2019 Rommel
10,617,815 B2 4/2020 Day et al.
10,646,651 B2 5/2020 Day et al.
10,681,207 B1 6/2020 Johnson et al.
10,692,595 B2 6/2020 Xavier et al.
10,728,262 B1 7/2020 Vaswani
10,740,436 B2 8/2020 Moskal et al.
10,741,280 B2 8/2020 Xavier et al.
10,757,219 B2 8/2020 Moskal
10,765,799 B2 9/2020 Belkin et al.
10,799,632 B2 10/2020 Kohlbrecher
10,812,380 B2 10/2020 Jha et al.
10,861,592 B2 12/2020 Xavier et al.
10,898,641 B2 1/2021 Day et al.
10,950,339 B2 3/2021 Xavier et al.
10,964,428 B2 3/2021 Xavier et al.
11,013,861 B2 5/2021 Wehba et al.
11,037,668 B2 6/2021 Ruchti et al.
11,052,193 B2 7/2021 Day et al.
11,139,058 B2 10/2021 Xavier et al.
11,151,290 B2 10/2021 Karakoyunlu et al.
11,152,108 B2 10/2021 Xavier et al.
11,152,109 B2 10/2021 Xavier et al.
11,152,110 B2 10/2021 Xavier et al.
11,194,810 B2 12/2021 Butler et al.
11,235,100 B2 2/2022 Howard et al.
11,289,183 B2 3/2022 Kohlbrecher
11,309,070 B2 4/2022 Xavier et al.
11,324,960 B2 5/2022 Sjoquist
11,328,804 B2 5/2022 Xavier et al.
11,328,805 B2 5/2022 Xavier et al.
11,373,753 B2 6/2022 Xavier et al.
11,437,132 B2 9/2022 Xavier et al.
11,470,000 B2 10/2022 Jha et al.
11,483,402 B2 10/2022 Xavier et al.
11,483,403 B2 10/2022 Xavier et al.
11,501,877 B2 11/2022 Kohlbrecher et al.
11,571,508 B2 2/2023 Jacobson et al.
11,574,721 B2 2/2023 Kohlbrecher
11,574,737 B2 2/2023 Dharwad et al.
11,587,669 B2 2/2023 Xavier et al.
11,590,057 B2 2/2023 Tagliamento et al.
11,594,326 B2 2/2023 Xavier et al.
11,605,468 B2 3/2023 Jacobson et al.
11,626,205 B2 4/2023 Arrizza et al.
11,628,246 B2 4/2023 Day et al.
11,628,254 B2 4/2023 Day et al.
11,654,237 B2 5/2023 Wehba et al.
11,670,416 B2 6/2023 Xavier et al.
11,763,927 B2 9/2023 Ruchti et al.
11,783,935 B2 10/2023 Xavier et al.
11,881,297 B2 1/2024 Xavier et al.
11,923,076 B2 3/2024 Xavier et al.
11,986,623 B2 5/2024 Jacobson et al.
11,996,188 B2 5/2024 Arrizza et al.
12,002,562 B2 6/2024 Kohlbrecher
12,036,390 B2 7/2024 Wehba et al.
12,040,068 B2 7/2024 Xavier et al.
12,042,623 B2 7/2024 Day et al.
12,042,631 B2 7/2024 Day et al.
12,046,361 B2 7/2024 Xavier et al.
12,047,292 B2 7/2024 Jha et al.
12,097,351 B2 9/2024 Belkin et al.
12,130,910 B2 10/2024 Vivek et al.
12,142,370 B2 11/2024 Xavier et al.
12,205,699 B1 1/2025 Kim et al.
12,205,702 B2 1/2025 Xavier et al.
12,303,464 B2 5/2025 Tagliamento et al.
12,337,142 B2 6/2025 Wehba et al.
12,380,982 B2 8/2025 Kohlbrecher
12,380,997 B2 8/2025 Arrizza et al.
12,395,429 B2 8/2025 Jha et al.
12,420,009 B2 9/2025 Day et al.
12,431,238 B2 9/2025 Vivek et al.
12,458,749 B2 11/2025 Jacobson et al.
12,562,268 B2 2/2026 Fryman
12,592,305 B2 3/2026 Xavier et al.
2001/0016056 A1 8/2001 Westphal et al.
2001/0029178 A1 10/2001 Criss et al.
2001/0031944 A1 10/2001 Peterson et al.
2001/0032099 A1 10/2001 Joao
2001/0037060 A1 11/2001 Thompson et al.
2001/0044731 A1 11/2001 Coffman et al.
2001/0048027 A1 12/2001 Walsh
2001/0051787 A1 12/2001 Haller et al.
2001/0056358 A1 12/2001 Dulong et al.
2002/0010595 A1 1/2002 Kapp
2002/0013551 A1 1/2002 Zaitsu et al.
2002/0013723 A1 1/2002 Mise
2002/0015018 A1 2/2002 Shimazu et al.
2002/0019584 A1 2/2002 Schulze et al.
2002/0021700 A1 2/2002 Hata et al.
2002/0026103 A1 2/2002 Norris et al.
2002/0029776 A1 3/2002 Blomquist
2002/0032583 A1 3/2002 Joao
2002/0040208 A1 4/2002 Flaherty et al.
2002/0040282 A1 4/2002 Bailey et al.
2002/0044043 A1 4/2002 Chaco et al.
2002/0044059 A1 4/2002 Reeder et al.
2002/0046335 A1 4/2002 Baum-Waidner
2002/0082728 A1 6/2002 Mueller et al.

(56) References Cited

U.S. PATENT DOCUMENTS

2002/0087115 A1 7/2002 Hartlaub
2002/0087116 A1 7/2002 Hartlaub
2002/0095486 A1 7/2002 Bahl
2002/0103675 A1 8/2002 Vanelli
2002/0123905 A1 9/2002 Goodroe et al.
2002/0143580 A1 10/2002 Bristol et al.
2002/0152239 A1 10/2002 Bautista-Lloyd et al.
2002/0154600 A1 10/2002 Ido et al.
2002/0161591 A1 10/2002 Danneels
2002/0173702 A1 11/2002 Lebel et al.
2002/0173875 A1 11/2002 Wallace et al.
2002/0193679 A1 12/2002 Malave et al.
2002/0194329 A1 12/2002 Alling
2003/0009244 A1 1/2003 Engleson
2003/0013959 A1 1/2003 Grunwald et al.
2003/0014222 A1 1/2003 Klass et al.
2003/0014817 A1 1/2003 Gallant et al.
2003/0025602 A1 2/2003 Medema et al.
2003/0028082 A1 2/2003 Thompson
2003/0036683 A1 2/2003 Kehr et al.
2003/0036744 A1 2/2003 Struys et al.
2003/0047126 A1 3/2003 Tomaschko
2003/0047600 A1 3/2003 Nakanishi et al.
2003/0050621 A1 3/2003 Lebel et al.
2003/0059750 A1 3/2003 Bindler et al.
2003/0060688 A1 3/2003 Ciarniello et al.
2003/0069963 A1 4/2003 Jayant et al.
2003/0079746 A1 5/2003 Hickle
2003/0097529 A1 5/2003 Arimilli et al.
2003/0104982 A1 6/2003 Wittmann et al.
2003/0105389 A1 6/2003 Noonan et al.
2003/0106553 A1 6/2003 Vanderveen
2003/0115358 A1 6/2003 Yun
2003/0120384 A1 6/2003 Haitin et al.
2003/0125662 A1 7/2003 Bui
2003/0130616 A1 7/2003 Steil
2003/0135087 A1 7/2003 Hickle et al.
2003/0139701 A1 7/2003 White et al.
2003/0140928 A1 7/2003 Bui et al.
2003/0140929 A1 7/2003 Wilkes et al.
2003/0141981 A1 7/2003 Bui et al.
2003/0143746 A1 7/2003 Sage, Jr.
2003/0144878 A1 7/2003 Wilkes et al.
2003/0158749 A1 8/2003 Olchanski et al.
2003/0187338 A1 10/2003 Say et al.
2003/0200116 A1 10/2003 Forrester
2003/0204416 A1 10/2003 Acharya
2003/0204781 A1 10/2003 Peebles et al.
2003/0212364 A1 11/2003 Mann et al.
2003/0212379 A1 11/2003 Bylund et al.
2003/0212821 A1 11/2003 Gillies et al.
2003/0216831 A1 11/2003 Hart et al.
2003/0217962 A1 11/2003 Childers et al.
2004/0008123 A1 1/2004 Carrender et al.
2004/0010786 A1 1/2004 Cool et al.
2004/0015132 A1 1/2004 Brown
2004/0019464 A1 1/2004 Martucci et al.
2004/0019607 A1 1/2004 Moubayed et al.
2004/0030323 A1 2/2004 Ullestad et al.
2004/0039257 A1 2/2004 Hickle
2004/0057226 A1 3/2004 Berthou et al.
2004/0064341 A1 4/2004 Langan et al.
2004/0064342 A1 4/2004 Browne et al.
2004/0064435 A1 4/2004 Moubayed et al.
2004/0073161 A1 4/2004 Tachibana
2004/0073811 A1 4/2004 Sanin
2004/0077934 A1 4/2004 Massad
2004/0078231 A1 4/2004 Wilkes et al.
2004/0078236 A1 4/2004 Stoodley et al.
2004/0085186 A1 5/2004 Eveland et al.
2004/0104271 A1 6/2004 Martucci et al.
2004/0122530 A1 6/2004 Hansen
2004/0128162 A1 7/2004 Schlotterbeck et al.
2004/0128163 A1 7/2004 Goodman et al.
2004/0133441 A1 7/2004 Brady et al.
2004/0139004 A1 7/2004 Cohen et al.
2004/0145480 A1 7/2004 Despotis
2004/0147034 A1 7/2004 Gore et al.
2004/0167464 A1 8/2004 Ireland et al.
2004/0167465 A1 8/2004 Kohler
2004/0167804 A1 8/2004 Simpson
2004/0172222 A1 9/2004 Simpson et al.
2004/0172283 A1 9/2004 Vanderveen
2004/0172301 A1 9/2004 Mihai et al.
2004/0172302 A1 9/2004 Martucci et al.
2004/0176667 A1 9/2004 Mihai et al.
2004/0176980 A1 9/2004 Bulitta et al.
2004/0176984 A1 9/2004 White et al.
2004/0181314 A1 9/2004 Zaleski
2004/0189708 A1 9/2004 Larcheveque et al.
2004/0193325 A1 9/2004 Bonderud
2004/0193328 A1 9/2004 Butterfield et al.
2004/0204673 A1 10/2004 Flaherty et al.
2004/0215278 A1 10/2004 Stegink et al.
2004/0220517 A1 11/2004 Starkweather et al.
2004/0225252 A1 11/2004 Gillespie et al.
2004/0236240 A1 11/2004 Kraus et al.
2004/0243438 A1 12/2004 Mintz
2004/0254434 A1 12/2004 Goodnow et al.
2005/0010269 A1 1/2005 Lebel et al.
2005/0020886 A1 1/2005 Hutchinson et al.
2005/0021006 A1 1/2005 Tonnies
2005/0027560 A1 2/2005 Cook
2005/0027567 A1 2/2005 Taha
2005/0038311 A1 2/2005 Kuth
2005/0038669 A1 2/2005 Sachdeva et al.
2005/0038680 A1 2/2005 McMahon
2005/0040226 A1 2/2005 Al-Sheikh
2005/0043620 A1 2/2005 Fallows et al.
2005/0049910 A1 3/2005 Lancaster et al.
2005/0055242 A1 3/2005 Bello et al.
2005/0055244 A1 3/2005 Mullan et al.
2005/0065465 A1 3/2005 Lebel et al.
2005/0065817 A1 3/2005 Mihai et al.
2005/0075544 A1 4/2005 Shapiro et al.
2005/0080801 A1 4/2005 Kothandaraman et al.
2005/0086071 A1 4/2005 Fox, Jr. et al.
2005/0086072 A1 4/2005 Fox
2005/0088704 A1 4/2005 Vaschillo et al.
2005/0090808 A1 4/2005 Malave et al.
2005/0099624 A1 5/2005 Staehr
2005/0102162 A1 5/2005 Blumenfeld
2005/0102165 A1 5/2005 Oshita et al.
2005/0102167 A1 5/2005 Kapoor
2005/0102669 A1 5/2005 Marney et al.
2005/0107923 A1 5/2005 Vanderveen
2005/0108057 A1 5/2005 Cohen et al.
2005/0117529 A1 6/2005 Ramos-Escano
2005/0119788 A1 6/2005 Engleson et al.
2005/0119914 A1 6/2005 Batch
2005/0131739 A1 6/2005 Rabinowitz et al.
2005/0135306 A1 6/2005 McAllen et al.
2005/0137522 A1 6/2005 Aoki
2005/0137573 A1 6/2005 McLaughlin
2005/0138428 A1 6/2005 McAllen et al.
2005/0154769 A1 7/2005 Eckart et al.
2005/0160057 A1 7/2005 Wefers et al.
2005/0171503 A1 8/2005 Van Den Berghe et al.
2005/0171815 A1 8/2005 Vanderveen
2005/0177096 A1 8/2005 Bollish et al.
2005/0177395 A1 8/2005 Blomquist
2005/0182306 A1 8/2005 Sloan
2005/0182355 A1 8/2005 Bui
2005/0187950 A1 8/2005 Parker
2005/0192557 A1 9/2005 Brauker et al.
2005/0197554 A1 9/2005 Polcha
2005/0197621 A1 9/2005 Poulsen et al.
2005/0210037 A1 9/2005 Wefers et al.
2005/0216479 A1 9/2005 Wefers et al.
2005/0216480 A1 9/2005 Wefers et al.
2005/0223045 A1 10/2005 Funahashi et al.
2005/0224083 A1 10/2005 Crass
2005/0234746 A1 10/2005 Funahashi
2005/0240305 A1 10/2005 Bogash et al.

(56) References Cited

U.S. PATENT DOCUMENTS

2005/0246416 A1 11/2005 Blomquist
2005/0251418 A1 11/2005 Fox, Jr. et al.
2005/0261660 A1 11/2005 Choi
2005/0273059 A1 12/2005 Mernoe et al.
2005/0273367 A1 12/2005 Nourie et al.
2005/0277873 A1 12/2005 Stewart et al.
2005/0277890 A1 12/2005 Stewart et al.
2005/0278194 A1 12/2005 Holland et al.
2006/0002556 A1 1/2006 Paul
2006/0004772 A1 1/2006 Hagan et al.
2006/0009727 A1 1/2006 O'Mahony et al.
2006/0009734 A1 1/2006 Martin
2006/0010098 A1 1/2006 Goodnow et al.
2006/0042139 A1 3/2006 Mendes
2006/0047270 A1 3/2006 Shelton
2006/0053036 A1 3/2006 Coffman et al.
2006/0064020 A1 3/2006 Burnes et al.
2006/0074633 A1 4/2006 Mahesh et al.
2006/0074920 A1 4/2006 Wefers et al.
2006/0079831 A1 4/2006 Gilbert
2006/0089539 A1 4/2006 Miodownik et al.
2006/0089854 A1 4/2006 Holland et al.
2006/0089855 A1 4/2006 Holland et al.
2006/0100746 A1 5/2006 Leibner-Druska
2006/0100907 A1 5/2006 Holland et al.
2006/0106649 A1 5/2006 Eggers et al.
2006/0111943 A1 5/2006 Wu
2006/0116639 A1 6/2006 Russell
2006/0116904 A1 6/2006 Brem
2006/0116907 A1 6/2006 Rhodes et al.
2006/0122481 A1 6/2006 Sievenpiper et al.
2006/0122867 A1 6/2006 Eggers et al.
2006/0129140 A1 6/2006 Todd et al.
2006/0129429 A1 6/2006 Moubayed et al.
2006/0129434 A1 6/2006 Smitherman et al.
2006/0129435 A1 6/2006 Smitherman et al.
2006/0136266 A1 6/2006 Tarassenko et al.
2006/0136271 A1 6/2006 Eggers et al.
2006/0143051 A1 6/2006 Eggers et al.
2006/0173260 A1 8/2006 Gaoni et al.
2006/0173406 A1 8/2006 Hayes et al.
2006/0173715 A1 8/2006 Wang et al.
2006/0173927 A1 8/2006 Beyer et al.
2006/0190302 A1 8/2006 Eggers et al.
2006/0195022 A1 8/2006 Trepagnier et al.
2006/0200007 A1 9/2006 Brockway et al.
2006/0200369 A1 9/2006 Batch et al.
2006/0211404 A1 9/2006 Cromp et al.
2006/0224141 A1 10/2006 Rush et al.
2006/0229918 A1 10/2006 Fotsch et al.
2006/0236373 A1 10/2006 Graves et al.
2006/0247606 A1 11/2006 Batch
2006/0253554 A1 11/2006 Uwais
2006/0258985 A1 11/2006 Russell
2006/0259327 A1 11/2006 Hoag
2006/0264895 A1 11/2006 Flanders
2006/0267753 A1 11/2006 Hussey et al.
2006/0268710 A1 11/2006 Appanna et al.
2006/0270971 A1 11/2006 Gelfand et al.
2006/0277206 A1 12/2006 Bailey et al.
2006/0287885 A1 12/2006 Frick
2007/0015972 A1 1/2007 Wang et al.
2007/0016443 A1 1/2007 Wachman et al.
2007/0021715 A1 1/2007 Kohlbrenner et al.
2007/0027506 A1 2/2007 Stender et al.
2007/0060796 A1 3/2007 Kim
2007/0060870 A1 3/2007 Tolle et al.
2007/0060871 A1 3/2007 Istoc
2007/0061393 A1 3/2007 Moore
2007/0065363 A1 3/2007 Dalal et al.
2007/0073419 A1 3/2007 Sesay
2007/0073822 A1 3/2007 Bennett et al.
2007/0078314 A1 4/2007 Grounsell
2007/0083870 A1 4/2007 Kanakogi
2007/0088333 A1 4/2007 Levin et al.
2007/0093786 A1 4/2007 Goldsmith et al.
2007/0100665 A1 5/2007 Brown
2007/0100667 A1 5/2007 Bardy
2007/0106126 A1 5/2007 Mannheimer et al.
2007/0112298 A1 5/2007 Mueller et al.
2007/0116037 A1 5/2007 Moore
2007/0118405 A1 5/2007 Campbell et al.
2007/0135866 A1 6/2007 Baker et al.
2007/0136098 A1 6/2007 Smythe et al.
2007/0142822 A1 6/2007 Remde
2007/0156282 A1 7/2007 Dunn
2007/0156452 A1 7/2007 Batch
2007/0169008 A1 7/2007 Varanasi et al.
2007/0179448 A1 8/2007 Lim et al.
2007/0186923 A1 8/2007 Poutiatine et al.
2007/0191817 A1 8/2007 Martin
2007/0191973 A1 8/2007 Holzbauer et al.
2007/0213657 A1 9/2007 Jennewine et al.
2007/0213684 A1 9/2007 Hickle et al.
2007/0214003 A1 9/2007 Holland et al.
2007/0215545 A1 9/2007 Bissler et al.
2007/0232867 A1 10/2007 Hansmann
2007/0233035 A1 10/2007 Wehba et al.
2007/0233049 A1 10/2007 Wehba et al.
2007/0233206 A1 10/2007 Frikart
2007/0240215 A1 10/2007 Flores
2007/0251835 A1 11/2007 Mehta et al.
2007/0253021 A1 11/2007 Mehta et al.
2007/0254593 A1 11/2007 Jollota et al.
2007/0255125 A1 11/2007 Moberg et al.
2007/0257788 A1 11/2007 Carlson
2007/0258395 A1 11/2007 Jollota et al.
2007/0288423 A1 12/2007 Kimoto
2007/0291647 A1 12/2007 Smith
2007/0299687 A1 12/2007 Palmer et al.
2007/0299695 A1 12/2007 Jung et al.
2008/0001771 A1 1/2008 Faoro et al.
2008/0004904 A1 1/2008 Tran
2008/0009684 A1 1/2008 Corsetti et al.
2008/0013559 A1 1/2008 Smith
2008/0033361 A1 2/2008 Evans et al.
2008/0033966 A1 2/2008 Wahl
2008/0034323 A1 2/2008 Blomquist
2008/0041942 A1 2/2008 Aissa
2008/0052704 A1 2/2008 Wysocki
2008/0065007 A1 3/2008 Peterson et al.
2008/0065417 A1 3/2008 Jung et al.
2008/0071217 A1 3/2008 Moubayed et al.
2008/0071251 A1 3/2008 Moubayed et al.
2008/0086088 A1 4/2008 Malcolm
2008/0091466 A1 4/2008 Butler et al.
2008/0095339 A1 4/2008 Elliott
2008/0097289 A1 4/2008 Steil et al.
2008/0097552 A1 4/2008 Dicks et al.
2008/0126969 A1 5/2008 Blomquist
2008/0139907 A1 6/2008 Rao et al.
2008/0148047 A1 6/2008 Appenzeller et al.
2008/0149117 A1 6/2008 Raghuram
2008/0154177 A1 6/2008 Moubayed et al.
2008/0172337 A1 7/2008 Banfield et al.
2008/0184219 A1 7/2008 Matsumoto
2008/0188796 A1 8/2008 Steil et al.
2008/0214919 A1 9/2008 Harmon et al.
2008/0244717 A1 10/2008 Jelatis et al.
2008/0246748 A1 10/2008 Cassidy et al.
2008/0256305 A1 10/2008 Kwon
2008/0259926 A1 10/2008 Tavares et al.
2008/0262469 A1 10/2008 Bristol et al.
2008/0269714 A1 10/2008 Mastrototaro et al.
2008/0269723 A1 10/2008 Mastrototaro et al.
2008/0275384 A1 11/2008 Mastrototaro et al.
2008/0300572 A1 12/2008 Rankers et al.
2008/0301298 A1 12/2008 Bernardi et al.
2008/0320387 A1 12/2008 Sasaki et al.
2008/0320466 A1 12/2008 Dias
2009/0003554 A1 1/2009 Katis et al.
2009/0005703 A1 1/2009 Fasciano
2009/0005728 A1 1/2009 Weinert et al.
2009/0006061 A1 1/2009 Thukral et al.

(56) References Cited

U.S. PATENT DOCUMENTS

2009/0006129 A1 1/2009 Thukral
2009/0006133 A1 1/2009 Weinert
2009/0018495 A1 1/2009 Panduro
2009/0036750 A1 2/2009 Weinstein et al.
2009/0051560 A1 2/2009 Manning et al.
2009/0054743 A1 2/2009 Stewart
2009/0054754 A1 2/2009 McMahon et al.
2009/0057399 A1 3/2009 Sajkowsky
2009/0063187 A1 3/2009 Johnson et al.
2009/0069785 A1 3/2009 Miller et al.
2009/0088701 A1 4/2009 Larsen
2009/0099866 A1 4/2009 Newman
2009/0099867 A1 4/2009 Newman
2009/0135196 A1 5/2009 Holland et al.
2009/0143662 A1 6/2009 Estes et al.
2009/0149743 A1 6/2009 Barron et al.
2009/0150174 A1 6/2009 Buck et al.
2009/0150439 A1 6/2009 Gejdos et al.
2009/0150878 A1 6/2009 Pathak et al.
2009/0157695 A1 6/2009 Roberts
2009/0158274 A1 6/2009 Roberts
2009/0177146 A1 7/2009 Nesbitt et al.
2009/0177769 A1 7/2009 Roberts
2009/0183147 A1 7/2009 Davis et al.
2009/0209938 A1 8/2009 Aalto-Setala
2009/0210250 A1 8/2009 Prax et al.
2009/0221890 A1 9/2009 Saffer et al.
2009/0231249 A1 9/2009 Wang et al.
2009/0270833 A1 10/2009 DeBelser
2009/0275886 A1 11/2009 Blomquist et al.
2009/0275896 A1 11/2009 Kamen et al.
2009/0284691 A1 11/2009 Marhefka et al.
2009/0292340 A1 11/2009 Mass et al.
2009/0306573 A1 12/2009 Gagner et al.
2009/0326340 A1 12/2009 Wang
2009/0326516 A1 12/2009 Bangera et al.
2010/0008377 A1 1/2010 Hasti et al.
2010/0022988 A1 1/2010 Wochner
2010/0036310 A1 2/2010 Hillman
2010/0056992 A1 3/2010 Hayter
2010/0083060 A1 4/2010 Rahman
2010/0088507 A1 4/2010 Cho
2010/0095229 A1 4/2010 Dixon et al.
2010/0121170 A1 5/2010 Rule
2010/0121246 A1 5/2010 Peters et al.
2010/0121415 A1 5/2010 Skelton et al.
2010/0121654 A1 5/2010 Portnoy et al.
2010/0121752 A1 5/2010 Banigan et al.
2010/0130933 A1 5/2010 Holland et al.
2010/0131434 A1 5/2010 Magent et al.
2010/0138523 A1 6/2010 Umess et al.
2010/0146137 A1 6/2010 Wu et al.
2010/0156633 A1 6/2010 Buck et al.
2010/0160854 A1 6/2010 Gauthier
2010/0160860 A1 6/2010 Celentano et al.
2010/0174266 A1 7/2010 Estes
2010/0191525 A1 7/2010 Rabenko et al.
2010/0198034 A1 8/2010 Thomas et al.
2010/0198196 A1 8/2010 Wei
2010/0200506 A1 8/2010 Ware et al.
2010/0209268 A1 8/2010 Davis
2010/0212675 A1 8/2010 Walling et al.
2010/0217621 A1 8/2010 Schoenberg
2010/0234708 A1 9/2010 Buck et al.
2010/0250732 A1 9/2010 Bucknell
2010/0271479 A1 10/2010 Heydlauf
2010/0273738 A1 10/2010 Valcke et al.
2010/0274218 A1 10/2010 Yodfat et al.
2010/0280486 A1 11/2010 Khair et al.
2010/0292634 A1 11/2010 Kircher
2010/0298765 A1 11/2010 Budiman et al.
2010/0305499 A1 12/2010 Matsiev
2010/0318025 A1 12/2010 John
2011/0001605 A1 1/2011 Kiani et al.
2011/0021898 A1 1/2011 Wei et al.
2011/0028885 A1 2/2011 Eggers et al.
2011/0040158 A1 2/2011 Katz et al.
2011/0060758 A1 3/2011 Schlotterbeck et al.
2011/0067092 A1 3/2011 Baker
2011/0071844 A1 3/2011 Cannon et al.
2011/0072379 A1 3/2011 Gannon
2011/0078253 A1 3/2011 Chan et al.
2011/0078608 A1 3/2011 Gannon et al.
2011/0093284 A1 4/2011 Dicks et al.
2011/0099313 A1 4/2011 Bolanowski
2011/0106318 A1 5/2011 Ledford et al.
2011/0125095 A1 5/2011 Lebel et al.
2011/0133946 A1 6/2011 Kopp
2011/0138185 A1 6/2011 Ju et al.
2011/0166628 A1 7/2011 Jain
2011/0175728 A1 7/2011 Baker, Jr.
2011/0178462 A1 7/2011 Moberg et al.
2011/0185010 A1 7/2011 Shatsky et al.
2011/0196748 A1 8/2011 Caron et al.
2011/0231216 A1 9/2011 Fyke et al.
2011/0252230 A1 10/2011 Segre et al.
2011/0257496 A1 10/2011 Terashima et al.
2011/0257798 A1 10/2011 Ali et al.
2011/0259954 A1 10/2011 Bartz et al.
2011/0264043 A1 10/2011 Kotnick et al.
2011/0264044 A1 10/2011 Bartz et al.
2011/0266221 A1 11/2011 Ware et al.
2011/0270045 A1 11/2011 Lebel et al.
2011/0275904 A1 11/2011 Lebel et al.
2011/0286457 A1 11/2011 Ee
2011/0289162 A1 11/2011 Furlong
2011/0289314 A1 11/2011 Whitcomb
2011/0289497 A1 11/2011 Kiaie et al.
2011/0295196 A1 12/2011 Chazot et al.
2011/0295341 A1 12/2011 Estes et al.
2011/0296051 A1 12/2011 Vange
2011/0296411 A1 12/2011 Tang et al.
2011/0313789 A1 12/2011 Karmen et al.
2011/0319813 A1 12/2011 Kamen et al.
2011/0320049 A1 12/2011 Chossat et al.
2012/0005680 A1 1/2012 Dolby et al.
2012/0011253 A1 1/2012 Friedman et al.
2012/0016305 A1 1/2012 Jollota
2012/0029941 A1 2/2012 Malave et al.
2012/0036102 A1 2/2012 Fletcher et al.
2012/0036550 A1 2/2012 Rodriguez
2012/0066501 A1 3/2012 Xiong
2012/0070045 A1 3/2012 Vesper et al.
2012/0079084 A1 3/2012 Forssell et al.
2012/0095437 A1 4/2012 Hemmerling
2012/0112903 A1 5/2012 Kaib et al.
2012/0130198 A1 5/2012 Beaule
2012/0143116 A1 6/2012 Ware et al.
2012/0150556 A1 6/2012 Galasso et al.
2012/0157920 A1 6/2012 Flachbart et al.
2012/0172802 A1* 7/2012 Blomquist ............. G16H 20/13
340/533
2012/0179135 A1 7/2012 Rinehart et al.
2012/0179136 A1 7/2012 Rinehart et al.
2012/0185267 A1 7/2012 Kamen et al.
2012/0203177 A1 8/2012 Lanier
2012/0210123 A1 8/2012 Castelnuovo
2012/0245554 A1 9/2012 Kawamura
2012/0259978 A1 10/2012 Petersen et al.
2012/0260012 A1 10/2012 Gao-Saari et al.
2012/0277716 A1 11/2012 Ali et al.
2012/0283630 A1 11/2012 Lee et al.
2012/0284734 A1 11/2012 McQuaid et al.
2012/0323212 A1 12/2012 Murphy
2012/0330380 A1 12/2012 Corndorf
2013/0006666 A1 1/2013 Schneider
2013/0006702 A1 1/2013 Wu
2013/0012877 A1 1/2013 Debelser et al.
2013/0012879 A1 1/2013 Debelser et al.
2013/0012880 A1 1/2013 Blomquist
2013/0015980 A1 1/2013 Evans et al.
2013/0036403 A1 2/2013 Geist
2013/0036412 A1 2/2013 Birtwhistle et al.
2013/0066265 A1 3/2013 Grant

(56) References Cited

U.S. PATENT DOCUMENTS

2013/0072872 A1 3/2013 Yodfat et al.
2013/0091350 A1 4/2013 Gluck
2013/0096444 A1 4/2013 Condurso et al.
2013/0096648 A1 4/2013 Benson
2013/0102963 A1 4/2013 Marsh et al.
2013/0104120 A1* 4/2013 Arrizza .................... G06F 8/65 717/173
2013/0114594 A1 5/2013 Van Zijst
2013/0116578 A1 5/2013 An
2013/0132721 A1 5/2013 Busser
2013/0133083 A1 5/2013 Kurumai
2013/0138452 A1 5/2013 Cork et al.
2013/0150824 A1 6/2013 Estes et al.
2013/0167245 A1 6/2013 Birtwhistle et al.
2013/0173473 A1 7/2013 Birtwhistle et al.
2013/0191770 A1 7/2013 Bartz et al.
2013/0204188 A1 8/2013 Kamen et al.
2013/0218080 A1 8/2013 Peterfreund et al.
2013/0274669 A1 10/2013 Stempfle et al.
2013/0275539 A1 10/2013 Gross et al.
2013/0276785 A1 10/2013 Melker et al.
2013/0291116 A1 10/2013 Homer
2013/0296823 A1 11/2013 Melker et al.
2013/0296984 A1 11/2013 Burnett et al.
2013/0317753 A1 11/2013 Kamen et al.
2013/0346108 A1 12/2013 Kamen et al.
2014/0025392 A1 1/2014 Chandrasenan
2014/0108783 A1 4/2014 Suzuki
2014/0142540 A1 5/2014 Imhof
2014/0142963 A1 5/2014 Hill et al.
2014/0163517 A1 6/2014 Finan et al.
2014/0172994 A1 6/2014 Raumann et al.
2014/0180711 A1 6/2014 Kamen et al.
2014/0197950 A1 7/2014 Shupp et al.
2014/0215490 A1 7/2014 Mathur et al.
2014/0249500 A1 9/2014 Estes et al.
2014/0257251 A1 9/2014 Bush et al.
2014/0266790 A1 9/2014 Al-Ali et al.
2014/0266794 A1 9/2014 Brown et al.
2014/0269643 A1 9/2014 Sun
2014/0276571 A1 9/2014 Ludolph
2014/0280522 A1 9/2014 Watte
2014/0294177 A1 10/2014 Shastry et al.
2014/0297329 A1 10/2014 Rock
2014/0316819 A1 10/2014 Dunsirn et al.
2014/0318639 A1 10/2014 Peret et al.
2014/0366878 A1 12/2014 Baron
2014/0371543 A1 12/2014 Steinhauer et al.
2015/0005935 A1 1/2015 Bae et al.
2015/0006907 A1 1/2015 Brouwer et al.
2015/0025503 A1* 1/2015 Searle .................... G16H 20/13 604/67
2015/0045729 A1 2/2015 Denzer et al.
2015/0058960 A1 2/2015 Schmoyer et al.
2015/0066531 A1 3/2015 Jacobson et al.
2015/0081894 A1 3/2015 Blomquist
2015/0100038 A1 4/2015 McCann et al.
2015/0100787 A1 4/2015 Westin et al.
2015/0117234 A1 4/2015 Raman et al.
2015/0151051 A1 6/2015 Tsoukalis
2015/0161354 A1 6/2015 Blomquist
2015/0196709 A1* 7/2015 Jacobson .............. A61M 5/142 604/67
2015/0199192 A1 7/2015 Borges et al.
2015/0199485 A1* 7/2015 Borges ................... G16H 40/40 600/323
2015/0207626 A1 7/2015 Neftel et al.
2015/0220890 A1 8/2015 Seshadri et al.
2015/0230760 A1 8/2015 Schneider
2015/0281128 A1 10/2015 Sindhu
2015/0325064 A1 11/2015 Downey
2015/0328396 A1 11/2015 Adams et al.
2015/0352301 A1 12/2015 Stedman et al.
2015/0365512 A1 12/2015 Mackenzie
2015/0371004 A1 12/2015 Jones
2015/0379237 A1 12/2015 Mills et al.
2016/0001003 A1 1/2016 Perazzo et al.
2016/0006695 A1 1/2016 Prodoehl et al.
2016/0015885 A1 1/2016 Pananen et al.
2016/0034655 A1 2/2016 Gray et al.
2016/0045661 A1 2/2016 Gray et al.
2016/0063471 A1 3/2016 Kobres et al.
2016/0119445 A1 4/2016 Hsieh
2016/0158437 A1 6/2016 Biasi et al.
2016/0204937 A1 7/2016 Edwards et al.
2016/0228633 A1 8/2016 Welsch et al.
2016/0241391 A1 8/2016 Fenster
2016/0277152 A1 9/2016 Xiang et al.
2016/0285876 A1 9/2016 Perez et al.
2016/0317742 A1 11/2016 Gannon et al.
2016/0321480 A1* 11/2016 Hamlin ................... G16Z 99/00
2016/0350513 A1 12/2016 Jacobson et al.
2016/0378618 A1 12/2016 Cmielowski
2017/0034277 A1 2/2017 Jackson et al.
2017/0041151 A1 2/2017 Kommireddy
2017/0054563 A1 2/2017 Verma
2017/0063559 A1 3/2017 Wallrabenstein
2017/0099148 A1 4/2017 Ochmanski et al.
2017/0104645 A1 4/2017 Wooton et al.
2017/0111301 A1 4/2017 Robinson
2017/0134357 A1 5/2017 Ohlsson
2017/0140134 A1 5/2017 Brough et al.
2017/0146381 A1 5/2017 Eckel et al.
2017/0149567 A1 5/2017 Moskal
2017/0149929 A1 5/2017 Moskal
2017/0214762 A1 7/2017 Swain et al.
2017/0258401 A1 9/2017 Volpe
2017/0258986 A1 9/2017 Tsoiukalis
2017/0262590 A1 9/2017 Karakosta et al.
2017/0325091 A1 11/2017 Freeman et al.
2017/0331804 A1 11/2017 Jellison et al.
2017/0351841 A1* 12/2017 Moskal .................. G16H 40/67
2018/0063724 A1 3/2018 Zhang et al.
2018/0121613 A1 5/2018 Connely, IV et al.
2018/0122502 A1 5/2018 Jones et al.
2018/0126067 A1 5/2018 Ledford et al.
2018/0157821 A1 6/2018 Fan
2018/0181712 A1 6/2018 Ensey et al.
2018/0247712 A1 8/2018 Muhsin et al.
2018/0272117 A1 9/2018 Fangrow
2018/0278594 A1 9/2018 Schiffman et al.
2018/0317826 A1 11/2018 Muhsin et al.
2018/0322948 A1 11/2018 Drost et al.
2018/0359085 A1 12/2018 Dervyn
2019/0006044 A1 1/2019 Brask
2019/0030329 A1 1/2019 Hannaman et al.
2019/0036688 A1 1/2019 Wasily et al.
2019/0066831 A1 2/2019 Mairs et al.
2019/0096518 A1 3/2019 Pace
2019/0116160 A1 4/2019 Bhat et al.
2019/0132196 A1 5/2019 Trivedi et al.
2019/0166501 A1 5/2019 Debates et al.
2019/0172590 A1 6/2019 Vesto et al.
2019/0182349 A1 6/2019 Goel et al.
2019/0207965 A1 7/2019 Espinosa
2019/0228863 A1 7/2019 Dharwad et al.
2019/0229982 A1 7/2019 Ikuta et al.
2019/0244689 A1 8/2019 Atkin
2019/0244707 A1 8/2019 Becker
2019/0245942 A1 8/2019 Moskal
2019/0272365 A1 9/2019 Huh
2019/0311803 A1 10/2019 Kohlbrecher et al.
2019/0328618 A1 10/2019 Hasegawa
2019/0329056 A1 10/2019 Sjoquist et al.
2019/0348160 A1 11/2019 Heavelyn et al.
2019/0392929 A1 12/2019 Gassman
2020/0023127 A1 1/2020 Simpson et al.
2020/0051190 A1 2/2020 Kamen et al.
2020/0054825 A1 2/2020 Kamen et al.
2020/0118692 A1 4/2020 Booker et al.
2020/0153627 A1 5/2020 Wentz
2020/0206413 A1 7/2020 Silkaitis et al.
2020/0213946 A1* 7/2020 Kruse ............... H04W 52/0229
2020/0220865 A1 7/2020 Finger et al.

(56) References Cited

U.S. PATENT DOCUMENTS

2020/0280608 A1* 9/2020 Borges .................... H04L 67/34
2020/0282139 A1 9/2020 Susi
2020/0334497 A1 10/2020 Barrett et al.
2020/0335194 A1 10/2020 Jacobson et al.
2020/0351376 A1 11/2020 Moskal
2020/0353167 A1 11/2020 Vivek et al.
2020/0353168 A1 11/2020 Keenan et al.
2020/0382323 A1 12/2020 Keselman
2021/0008457 A1 1/2021 Schouviller et al.
2021/0014259 A1 1/2021 Harris et al.
2021/0045640 A1 2/2021 Poltorak
2021/0085855 A1 3/2021 Belkin et al.
2021/0136157 A1 5/2021 Kauppila et al.
2021/0375421 A1 12/2021 Ruchti et al.
2021/0375438 A1 12/2021 Xavier et al.
2021/0409362 A1 12/2021 Katis et al.
2022/0037011 A1 2/2022 Fryman
2022/0037012 A1 2/2022 Fryman
2022/0051777 A1* 2/2022 Xavier ................... G16H 20/17
2022/0054746 A1 2/2022 Patel et al.
2022/0062541 A1 3/2022 Kamen et al.
2022/0070221 A1 3/2022 Labudde et al.
2022/0129452 A1 4/2022 Butler et al.
2022/0139536 A1 5/2022 Xavier et al.
2022/0139537 A1 5/2022 Xavier et al.
2022/0150307 A1 5/2022 Walsh et al.
2022/0165404 A1 5/2022 Vivek et al.
2022/0189605 A1 6/2022 Kelly et al.
2022/0191191 A1 6/2022 Brockhaus
2022/0223283 A1 7/2022 Biasi et al.
2022/0328175 A1 10/2022 Arrizza et al.
2022/0331513 A1 10/2022 Howard et al.
2022/0344023 A1 10/2022 Xavier et al.
2022/0375565 A1 11/2022 Xavier et al.
2022/0384059 A1 12/2022 Xavier et al.
2023/0009405 A1 1/2023 Xavier et al.
2023/0009417 A1 1/2023 Xavier et al.
2023/0108034 A1 4/2023 Fischer et al.
2023/0139360 A1 5/2023 Kohlbrecher et al.
2023/0145267 A1 5/2023 Xavier et al.
2023/0147762 A1 5/2023 Xavier et al.
2023/0231834 A1 7/2023 Carter
2023/0253108 A1 8/2023 Dharwad et al.
2023/0298768 A1 9/2023 Jacobson et al.
2024/0047035 A1 2/2024 Ruchti et al.
2024/0062867 A1* 2/2024 Lim ...................... G06F 1/3265
2024/0293610 A1 9/2024 Jacobson
2024/0321441 A1 9/2024 Rohlwing
2024/0371508 A1 11/2024 Mills et al.
2024/0424211 A1 12/2024 Day et al.
2025/0232033 A1 7/2025 Vivek et al.
2025/0381344 A1 12/2025 Wehba et al.
2026/0012334 A1 1/2026 Dandekar et al.
2026/0018280 A1 1/2026 Arrizza et al.
2026/0054005 A1 2/2026 Day et al.

FOREIGN PATENT DOCUMENTS

CA 2 060 151 8/1997
CA 2 125 300 10/1999
CA 2 630 102 10/2008
CA 2 687 587 12/2008
CA 2 897 897 7/2014
CA 2 898 825 7/2014
CA 2 900 564 10/2014
CA 2 606 968 1/2020
CN 1759398 4/2006
CN 102521474 6/2012
CN 103816582 5/2014
CN 103920206 7/2014
CN 102300501 4/2015
CN 104487976 4/2015
CN 106960128 7/2017
CN 107810536 1/2023
DE 31 12 762 1/1983
DE 34 35 647 7/1985
DE 198 44 252 3/2000
DE 199 32 147 1/2001
DE 100 53 116 5/2001
DE 103 52 456 7/2005
EP 0 319 267 6/1989
EP 0 380 061 8/1990
EP 0 384 155 8/1990
EP 0 460 533 12/1991
EP 0 564 127 6/1993
EP 0 633 035 1/1995
EP 0 652 528 5/1995
EP 0 672 427 9/1995
EP 0 683 465 11/1995
EP 0 880 936 12/1998
EP 1 050 993 11/2000
EP 1 157 711 11/2001
EP 1 174 817 1/2002
EP 0 664 102 4/2002
EP 1 197 178 4/2002
EP 0 830 775 8/2002
EP 1 500 025 4/2003
EP 1 487 171 7/2007
EP 1 933 497 6/2008
EP 2 026 223 2/2009
EP 2 113 842 11/2009
EP 2 228 004 9/2010
EP 2 243 506 10/2010
EP 2 410 448 1/2012
EP 2 742 961 6/2014
EP 2 874 087 5/2015
ES 2 371 995 1/2012
FR 2 717 919 9/1995
GB 2 285 135 6/1995
JP 04-161139 6/1992
JP 07-502678 3/1995
JP 11-500643 1/1999
JP 2000-316820 11/2000
JP 2002-531154 9/2002
JP 2003-016183 1/2003
JP 2003-296173 10/2003
JP 2003-308586 10/2003
JP 2005-021463 1/2005
JP 2005-527284 9/2005
JP 2005-284846 10/2005
JP 2006-047319 2/2006
JP 2006-520949 9/2006
JP 2007-518479 7/2007
JP 2007-525256 9/2007
JP 2008-080036 4/2008
JP 2008-516303 5/2008
JP 2008-158622 7/2008
JP 2008-529675 8/2008
JP 2009-163534 7/2009
JP 2010-502361 1/2010
JP 2011-506048 3/2011
JP 2012-011204 1/2012
JP 2012-070991 4/2012
JP 2012-523895 10/2012
JP 2014-068283 4/2014
JP 5647644 1/2015
TW 200426656 12/2004
TW I631966 8/2018
TW M589351 1/2020
TW M598505 7/2020
WO WO 84/001719 5/1984
WO WO 91/016416 10/1991
WO WO 92/010985 7/1992
WO WO 92/013322 8/1992
WO WO 94/005355 3/1994
WO WO 96/008755 3/1996
WO WO 96/025186 8/1996
WO WO 96/025963 8/1996
WO WO 98/012670 3/1998
WO WO 98/019263 5/1998
WO WO 99/051003 10/1999
WO WO 00/013580 3/2000
WO WO 00/053243 9/2000
WO WO 01/014974 3/2001

(56) References Cited

FOREIGN PATENT DOCUMENTS

| | | |
|---|---|---|
| WO | WO 01/033484 | 5/2001 |
| WO | WO 01/045014 | 6/2001 |
| WO | WO 01/083007 | 11/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/023551 | 3/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/059495 | 5/2008 |
| WO | WO 2008/064254 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/025394 | 2/2013 |
| WO | WO 2013/045506 | 4/2013 |
| WO | WO 2014/100557 | 6/2014 |
| WO | WO 2014/100687 | 6/2014 |
| WO | WO 2014/100736 | 6/2014 |
| WO | WO 2014/131729 | 9/2014 |
| WO | WO 2014/131730 | 9/2014 |
| WO | WO 2015/047595 | 4/2015 |
| WO | WO 2015/124569 | 8/2015 |
| WO | WO 2016/099551 | 6/2016 |
| WO | WO 2016/179389 | 11/2016 |
| WO | WO 2017/200989 | 11/2017 |
| WO | WO 2019/219290 | 11/2019 |
| WO | WO 00/003344 | 1/2020 |
| WO | WO 2020/227403 | 11/2020 |
| WO | WO 2021/201884 | 10/2021 |
| WO | WO 2022/006014 | 1/2022 |
| WO | WO 2022/051230 | 3/2022 |
| WO | WO 2023/044335 | 3/2023 |
| WO | WO 2023/159134 | 8/2023 |
| WO | WO 2024/196590 | 9/2024 |
| WO | WO 2025/122515 | 6/2025 |

OTHER PUBLICATIONS

Shah et al. Implementation of Smart Infusion Pumps: A Scoping Review and Case Study Discussion of the Evidence of the Role of the Pharmacist, Pharmacy 2020, 8, 239; doi: 10.3390/.*

Ahn et al., "Towards Scalable Authentication in Health Services", Eleventh IEEE International Workshops on Enabling Technologies: Infrastructure for Collaborative Enterprises, Jun. 2002, pp. 83-88.

Akridge, Jeannie, "New Pumps Outsmart User Error", Healthcare Purchasing News, Apr. 2011, pp. 10, <http://web.archive.org/web/20110426122450/http://www.hpnonline.com/inside/2011-04/1104-OR-Pumps.html>.

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.

Aragon, Daleen RN, Ph.D., CORN, "Evaluation of Nursing Work Effort and Perceptions About Blood Glucose Testing in Tight Glycemic Control", American Journal of Critical Care, Jul. 2006, vol. 15, No. 4, pp. 370-377.

ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.

Beard et al., "Total Quality Pain Management: History, Background, Resources", Abbott Laboratories, TQPM Survey History, available Feb. 2015 or earlier, pp. 1-3.

Bektas et al., "Bluetooth Communication Employing Antenna Diversity", Proceedings of Eight IEEE International Symposium on Computers and Communication, Jul. 2003, pp. 6.

Bellare et al., "Security Proofs for Identity-Based Identification and Signature Schemes", Lecture Notes in Computer Science, Jan. 2009, vol. 22, No. 1, pp. 18.

Bequette, Ph.D., "A Critical Assessment of Algorithms and Challenges in the Development of a Closed- Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.

Braun, "Infusomat® Space and Accessories", Instructions for Use, Nov. 2010, pp. 68. <http://corp.bbraun.ee/Extranet/Infusionipumbad/Kasutusjuhendid/Vanad/Kasutusjuhend-Infusomat_Space(vers688J,inglise_k).pdf>.

Brownlee, Seth, "Product Spotlight: The Plum A+ with Hospira MedNet Infusion System", PP&P Magazine, Dec. 2005, vol. 2, No. 7, pp. 2.

Cannon, MD et al., "Automated Heparin-Delivery System to Control Activated Partial Thromboplastin Time", Circulation, Feb. 16, 1999, vol. 99, pp. 751-756.

Cardinal Health, "Alaris® Syringe Pumps" Technical Service Manual, Copyright 2002-2006, Issue 9, pp. 1-88, <http://www.frankshospitalworkshop.com/equipment/documents/infusion_pumps/service_manuals/Cardinal_Alaris_-_Service_Manual.pdf>.

"CareAware® Infusion Management", Cerner Store, as printed May 12, 2011, pp. 3, <https://store.cerner.com/items/7>.

Chen et al., "Enabling Location-Based Services on Wireless LANs", The 11th IEEE International Conference on Networks, ICON 2003, Sep. 28-Oct. 1, 2003, pp. 567-572.

(56) References Cited

OTHER PUBLICATIONS

"Computer Dictionary", Microsoft Press, Third Edition, Microsoft Press, 1997, pp. 430 & 506.
"Context-Free Grammar", Wikipedia.org, as last modified Mar. 5, 2010 in 11 pages, <https://en.wikipedia.org/w/index.php/?title=Context-free_grammar&oldid=347915989>.
Crawford, Anne J., MSN, RNC, "Building a Successful Quality Pain Service: Using Patient Satisfaction Data and the Clinical Practice Guideline", USA, 1995, pp. 1-6.
Crocker et al., "Augmented BNF for Syntax Specifications: ABNF", Network Working Group, Standards Track, Jan. 2008, pp. 16.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.
Dayhoff et al., "Medical Data Capture and Display: The Importance of Clinicians' Workstation Design", AMIA, Inc., 1994, pp. 541-545.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
Doesburg et al., "Improved Usability of a Multi-Infusion Setup Using a Centralized Control Interface: A Task-Based Usability Test", Aug. 11, 2017, PLoS ONE, vol. 12, No. 8, pp. 10.
"Download", Free On-Line Dictionary of Computing, as archived Jun. 16, 2010 in 1 page, http://web.archive.org/web/20100616010314/https://foldoc.org/download.
East PhD et al., "Digital Electronic Communication Between ICU Ventilators and Computers and Printers", Respiratory Care, Sep. 1992, vol. 37, No. 9, pp. 1113-1122.
Edworthy, Judy, "Medical Audible Alarms: A Review", Journal of the American Medical Informatics Association, vol. 20, No. 3, 2013, pp. 584-589.
Einhorn, George W., "Total Quality Pain Management: A Computerized Quality Assessment Tool for Postoperative Pain Management", Abbott Laboratories, Chicago, IL, Mar. 2, 2000, pp. 1-4.
Eskew et al., "Using Innovative Technologies to Set New Safety Standards for the Infusion of Intravenous Medications", Hospital Pharmacy, 2002, vol. 37, No. 11, pp. 1179-1189.
Felleiter et al., "Data Processing in Prehospital Emergency Medicine", International journal of Clinical Monitoring and Computing, Feb. 1995, vol. 12, No. 1, pp. 37-41.
"File Verification", Wikipedia.org, as last modified Oct. 11, 2011 in 2 pages, <https://en.wikipedia.org/w/index.php?title=File_verification&oldid=455048290>.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Gabel et al., "Camp: A Common API for Measuring Performance", 21st Large Installations System Administration Conference (LISA '07), 2007, pp. 49-61.
Gage et al., "Automated Anesthesia Surgery Medical Record System", International Journal of Clinical Monitoring and Computing, Dec. 1990, vol. 7, No. 4, pp. 259-263.
Galt et al., "Personal Digital Assistant-Based Drug Information Sources: Potential to Improve Medication Safety", Journal of Medical Library Association, Apr. 2005, vol. 93, No. 2, pp. 229-236.
Gardner, Ph.D et al., "Real Time Data Acquisition: Recommendations for the Medical Information Bus (MIB)", 1992, pp. 813-817.
"General-Purpose Infusion Pumps", Health Devices, EXRI Institute, Oct. 1, 2002, vol. 31, No. 10, pp. 353-387.
Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
"GPS Tracker for Medical Equipment", <http://www.trackingsystem.com/forbusinesses/corporate-trackingsystem/1098-gps-tracker-formedicalequipment.html>, Mar. 15, 2015, pp. 2.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Nos. from 3000 to 59,999", Technical Service Manual, Graseby Medical Ltd., Apr. 2002, Issue A, pp. 71.
Gutwin et al., "Gone but not Forgotten: Designing for Disconnection in Synchronous Groupware", CSCW 2010, Feb. 6-10, 2010, Savannah, Georgia, USA., pp. 179-188.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hamann et al., "Pumpsim: A Software Package for Simulating Computer-Controlled Drug Infusion Pumps", Annual International Conference of the IEEE Engineering in Medicine and Biology Society, 1990, vol. 12, No. 5, pp. 2019-2020.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.
Hospira, GemStar® Pain Management Infusion System 9-084-PR1-2-2, <www.hospira.com/products/gemstar_painmanagement.aspx>, Jan. 28, 2010, pp. 1-2.
Huang et al., "Secure Identity-Based Data Sharing and Profile Matching for Mobile Healthcare Social Networks in Cloud Computing", vol. 6, Jul. 2018, pp. 36584-36594.
Introducing Abbott TQPM (Total Quality Pain Management), Abbott Laboratories, Abbott Park, IL, May 2000, pp. 1-4.
"Infusion Pump", Wikipedia.org, as last modified Mar. 27, 2014, in 3 pages, <https://web.archive.org/web/20140703024932/https://en.wikipedia.org/wiki/Infusion_pump>.
International Search Report and Written Opinion received in PCT Application No. PCT/US2023/062752, dated Jun. 8, 2023 in 12 pages.
Isaka et al., "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety in Veterans Administration Medical Centers", Journal of Healthcare Information Management, Dec. 6, 2004, vol. 16, No. 1, pp. 46-51.
Kent Displays, "Reflex TM Electronic Skins", Product Brief 25127B, 2009, pp. 2.
Kent Displays, "Reflex Electronic Skins Engineering Evaluation Kit", 25136A, Mar. 10, 2009.
Lefkowitz et al., "A Trial of the Use of Bar Code Technology to Restructure a Drug Distribution and Administration System", Hospital Pharmacy, Mar. 31, 1991, vol. 26, No. 3, pp. 239-242.
Lenssen et al., "Bright Color Electronic Paper Technology and Applications", IDS '09 Publication EP1-2 (Phillips Research), 2009, pp. 529-532.
Leveson, Nancy, "Medical Devices: The Therac-25", Appendix A, University of Washington, 1995, pp. 49.

(56) References Cited

OTHER PUBLICATIONS

Li et al., "Hijacking an Insulin Pump: Security Attacks and Defenses for a Diabetes Therapy System", 2011 IEEE 13th International Conference on e-Health Networking, Applications and Services, 2011, pp. 150-156.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
"McKesson Automation and ALARIS Medical Systems Developing Point-of-Care Bar Coding Solution to Improve IV Medication Safety", PR Newswire, NY, Dec. 9, 2002, pp. 4.
Medfusion™, "Medfusion Syringe Infusion Pump Model 4000", Operator's Manual, Software Version V1.1, Sep. 2011, pp. 154. <http://www.medfusionpump.com/assets/literature/manuals/Operators_Manual_4000_40-5760-51A.pdf>.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Michienzi, Kelly, "Managing Drug Library Updates", Pharmacy Purchasing Products, https://www.pppmag.com/article/1061, Feb. 2012, vol. 9, pp. 22-23.
Micrel Medical Devices, "MP Daily +" <http://web.archive.org/web/20130803235715/http://www.micrelmed.com/index.aspx?productid=9> as archived Aug. 3, 2013 in 1 page.
Moghissi, Etie, MD, FACP, FACE, "Hyperglycemia in Hospitalized Patients", A Supplement to ACP Hospitalist, Jun. 15, 2008, pp. 32.
Murray, Jr. et al., "Automated Drug Identification System (during surgery)", IEEE Proceedings of Southeastcon '91, Apr. 7-10, 1991, pp. 265.
Nicholson et al., "Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.
Nojoumian et al., "Social Secret Sharing in Cloud Computing Using a New Trust Function", 2012 Tenth Annual International Conference on Privacy, Security and Trust, pp. 161-167.
Nolan et al., "The P1073 Medical Information Bus Standard: Overview and Benefits for Clinical Users", 1990, pp. 216-219.
Omnilink Systems, Inc., "Portable Medical Equipment Tracking" <http://www.omnilink.com/portablemedicalequipmenttracking/>, Mar. 15, 2015, pp. 2.
O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.
Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Philips, "IntelliSpace Event Management and IntelliVue Patient Monitoring", Release 10, 2011, <http://incenter.medical.philips.com/doclib/enc/fetch/2000/4504/577242/577243/577247/582646/583147/83 59175/Philips_Patient_Monitoring_and_IntelliSpace_Event_Management_Interoperability.pdf%3fnodeid%3d8508574%26vernum%3d-2>, pp. 2.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.
Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"Sigma Spectrum: Operator's Manual", May 15, 2008, pp. 63. <https://usme.com/content/manuals/sigma-spectrum-operator-manual.pdf>.
"Sigma Spectrum: Operator's Manual", Oct. 2009, pp. 72. <http://static.medonecapital.com/manuals/userManuals/Sigma-Spectrum-Operator-Manual-October-2009.pdf>.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. <http://www.thomasland.com/hpj4209-832.pdf>.
Slack, W.V., "Information Technologies for Transforming Health Care", <https://www.andrew.cmu.edu/course/90-853/medis.dir/otadocs.dir/03ch2.pdf>, Ch. 2, 1995, pp. 29-78.
Smith, Joe, "Infusion Pump Informatics", CatalyzeCare: Transforming Healthcare, as printed May 12, 2011, pp. 2.

(56) References Cited

OTHER PUBLICATIONS

Sodders, Lisa, "VA Center Keeps Medicine in Right Hands", The Capital-Journal, Dec. 4, 1999, pp. 1-2.
"Software Versioning", Wikipedia.org, dated Oct. 16, 2011 in 11 pages, <https://en.wikipedia.org/w/index.php?title=Software_versioning&oldid=455859110>.
Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.
Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
"TCG TPM v2.0 Provisioning Guidance", Reference, Version 1, Revision 1, Mar. 15, 2017, pp. 1-43.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, November-Dec. 1994, pp. 671-677.
Yoo et al., "Code-Based Authentication Scheme for Lightweight Integrity Checking of Smart Vehicles", IEEE Access, 2018, vol. 6, pp. 46731-46741.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
Amano et al., "A Remote Drip Infusion Monitoring System Employing Bluetooth," 2012 Annual International Conference of the IEEE Engineering in Medicine and Biology Society, pp. 2029-2032.
Banerjee et al., "Token-Based Authentication Techniques on Open Source Cloud Platforms", Sistemas y Telemática, vol. 16, No. 47, 2018, p. 17.
Chan, Katherine Yin-Yee. "Mitigating Risks Associated with Secondary Intravenous Infusions: An Empirical Evaluation of a Technology-Based, Training-Based, and Practice-Based Intervention." Order No. 1570719 University of Toronto (Canada), 2013. Ann Arbor: ProQuest. Web. Nov. 23, 2024, p. 182.
Cloudflare, "What Happens in a TLS Handshake? | SSL Handshake", as archived May 19, 2020, https://web.archive.org/web/20200519192121/https:/www.cloudflare.com/en-au/learning/ssl/what-happens-in-a-tls-handshake/, 4 pages.
Fan et al., "Smart Medication Delivery Systems: Infusion Pumps", Supplementary Report, Healthcare Human Factors, Feb. 26, 2010, p. 94.
Murphy, Robert, "The Design of Safety-Critical Medical Infusion Devices", May 30, 2007, Doctor of Philosophy submission, p. 317.
O'Brien et al., "Securing wireless infusion pumps", NIST Special Publication (1800): 8B, 2018, p. 85.
Rahmani et al., "Smart e-Health Gateway: Bringing Intelligence to Internet-of-Things Based Ubiquitous Healthcare Systems", 2015 12th Annual IEEE Consumer Communications and Networking Conference (CCNC), Jul. 2015, pp. 826-834.
Sabir et al., "Authentication Model Based on JWT and Local PKI for Communication Security in Multi-agent Systems", International Conference Europe Middle East & North Africa Information Systems and Technologies to Support Learning. Springer, Cham, 2019, pp. 469-479.
Sethia et al., "Security Framework for Portable NFC Mobile Based Health Record System", Oct. 2016, IEEE 12th International Conference on Wireless and Mobile Computing, Networking and Communications, pp. 1-8.
Stack Exchange, "Avoiding SSL handshake for each call", as archived Sep. 22, 2021, https://web.archive.org/web/20210922184153/https:/security.stackexchange.com/questions/56623/avoiding-ssl-handshake-for-each-call, 3 pages.
Wang et al., "Infusion Monitoring System Based on Wireless Transmission", 2011 4th IEEE International Symposium on Microwave, Antenna, Propagation and EMC Technologies for Wireless Communications, pp. 656-659.

* cited by examiner

AUTOMATED INFUSION PUMP UPDATING

CROSS-REFERENCE TO RELATED APPLICATIONS

All applications for which a foreign or domestic priority claim is identified in the Application Data Sheet as filed with the present application are hereby incorporated by reference and made part of this specification.

BACKGROUND

Field

This disclosure relates to intravenous infusion pumps, including electronically controlled intravenous infusion pumps.

Related Art

Patients all over the world who are in need of medical care commonly receive intravenous infusion therapy, especially during surgery or when hospitalized. This generally involves inserting a needle into a patient's blood vessel, usually in the hand or arm, and then coupling the needle to a catheter in communication with one or more different types of therapeutic fluids. Once connected, the fluid travels from the fluid source(s), through the catheter, and into the patient. The fluid can provide certain desired benefits to the patient, such as maintaining hydration or nourishment, diminishing infection, reducing pain, lowing the risk of blood clots, maintaining blood pressure, providing chemotherapy, and/or delivering any other suitable drug or other therapeutic liquid to the patient. Electronic infusion pumps in communication with the fluid sources and the patient can help to increase the accuracy and consistency of fluid delivery to patients, but current electronic infusion pumps have disadvantages.

SUMMARY

In some aspects, the techniques described herein relate to a method of automatically updating software stored on an infusion pump, the method including: waking a processor within the infusion pump from an off state, while maintaining a communication engine within the infusion pump in the off state; determining that the infusion pump is receiving electrical power from a battery coupled to the infusion pump; determining that the battery contains sufficient energy to complete an update to the infusion pump; and waking the communication engine within the infusion pump from the off state, wherein the communication engine is configured to determine whether an update is available to be acquired from a remote location.

In some aspects, the techniques described herein relate to a method, further including: determining that the update is not available; and causing the communication engine and the processor to return to the off state.

In some aspects, the techniques described herein relate to a method, further including: determining that an update is available; acquiring the update; and updating the infusion pump with the update.

In some aspects, the techniques described herein relate to a method, wherein acquiring the update includes receiving the update via a wired or wireless network.

In some aspects, the techniques described herein relate to a method, wherein the update includes an operating software update.

In some aspects, the techniques described herein relate to a method, further including installing the operating software update.

In some aspects, the techniques described herein relate to a method, wherein the update includes a drug library update.

In some aspects, the techniques described herein relate to a method, wherein waking the processor includes waking the processor a predetermined number of times during a predetermined period.

In some aspects, the techniques described herein relate to a method, wherein the predetermined number of times is one of one, two, three, or four times, and the predetermined period is a day.

In some aspects, the techniques described herein relate to a method, wherein the processor receives no electrical power while in the off state.

In some aspects, the techniques described herein relate to an infusion pump configured to automatically determine whether to receive an update, including: a battery; a processor configured to receive power from the battery; a communication engine in communication with the processor and configured to communicate with a remote location; a memory in communication with the processor and storing instructions that when executed by the processor configure the processor to: wake the processor from an off state; determine that the infusion pump is receiving electrical power from the battery; determine whether the battery contains sufficient energy to complete an update to the infusion pump; and in response to determining that the battery contains sufficient energy to complete an update to the infusion pump, wake the communication engine from an off state and cause the communication engine to determine whether an update is available to be acquired from the remote location; and a clock in communication with the processor and configured to wake the processor from the off state in response to an alarm signal generated by the clock and cause the processor to execute the instructions in response to the alarm signal.

In some aspects, the techniques described herein relate to a infusion pump, wherein the processor receives no electrical power while in the off state.

In some aspects, the techniques described herein relate to a infusion pump, wherein the instructions further enable the processor to determine that the update is not available, and in response to determining that the update is not available, cause the communication engine and the processor to return to the off state.

In some aspects, the techniques described herein relate to a infusion pump, wherein the instructions further enable the processor to determine that the update is available, and in response to determining that the update is available, cause the communication engine to acquire the update, and cause the processor to update the infusion pump with the update.

In some aspects, the techniques described herein relate to a infusion pump, wherein the instructions cause the communication engine to acquire the update by receiving the update via a wired or wireless network.

In some aspects, the techniques described herein relate to a infusion pump, wherein the update includes an operating software update and wherein the instructions cause the processor to update the infusion pump by installing the operating software update on the infusion pump.

In some aspects, the techniques described herein relate to a infusion pump, wherein the update includes a drug library update, and wherein the instructions cause the processor to update the infusion pump by storing the drug library update within the infusion pump.

In some aspects, the techniques described herein relate to a infusion pump, wherein the instructions further enable the processor to, in response to determining that the battery is not storing enough energy to acquire the update and update the infusion pump with the update, cause the infusion pump to return to the off state.

In some aspects, the techniques described herein relate to a infusion pump, wherein the instructions are configured to wake the processor by waking the processor a predetermined number of times during a predetermined period.

In some aspects, the techniques described herein relate to a infusion pump, wherein the predetermined number of times is one of one, two, three, or four times, and the predetermined period is a day.

BRIEF DESCRIPTION OF THE DRAWINGS

The following drawings and the associated descriptions are provided to illustrate embodiments of the present disclosure and do not limit the scope of the claims.

DETAILED DESCRIPTION

Figure 1A:
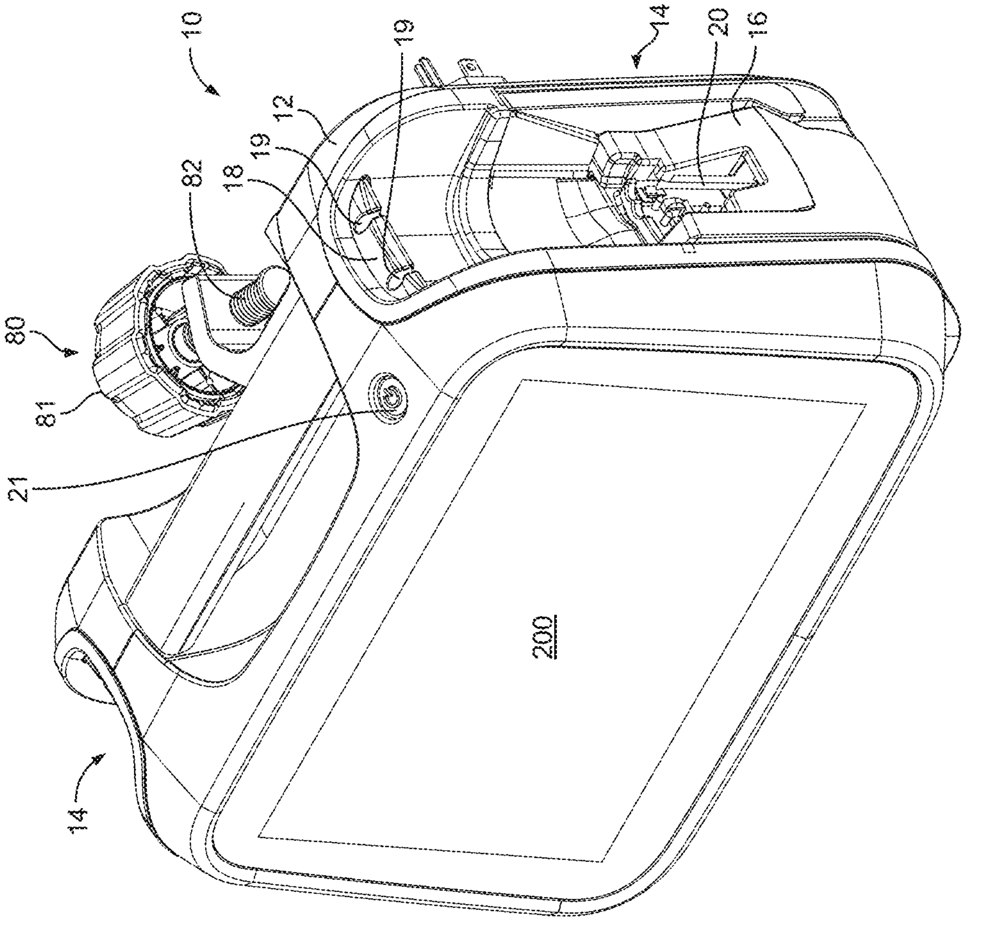
FIGS. 1A-1E show front perspective, front elevational, rear elevational, top plan, and side elevational views, respectively, of an example of an infusion pump.
Figure 1B:
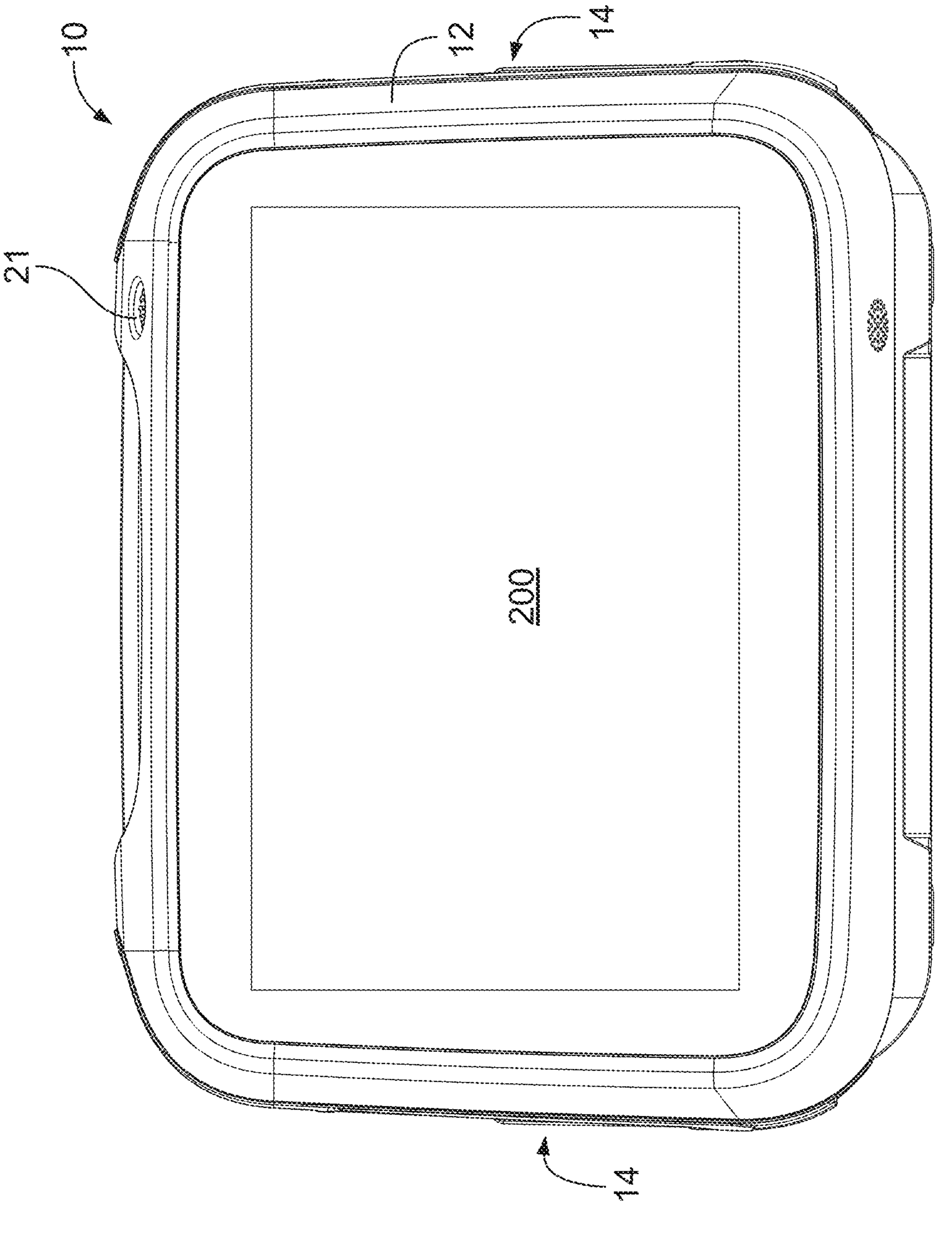
Figure 1C:
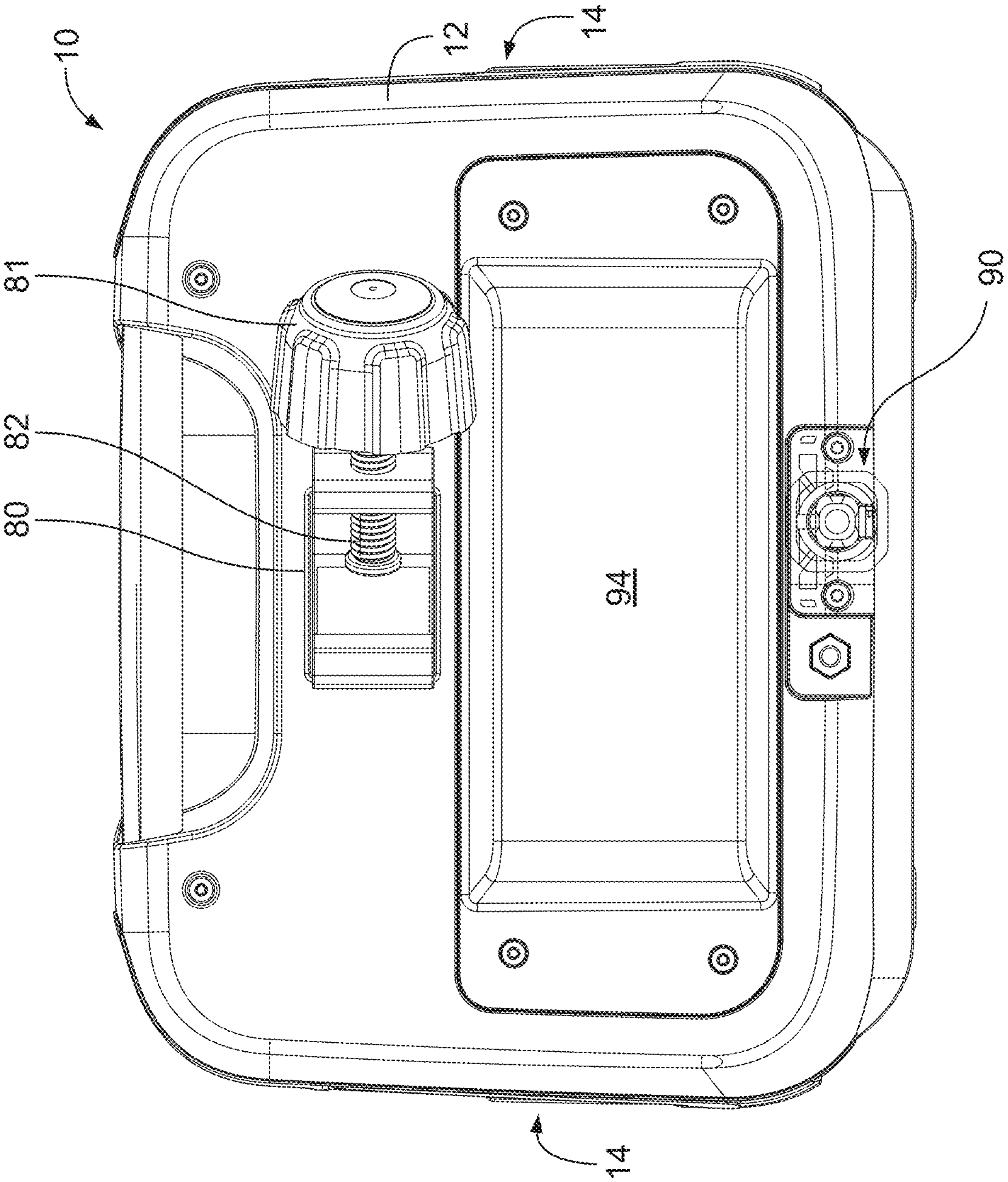
Figure 1D:
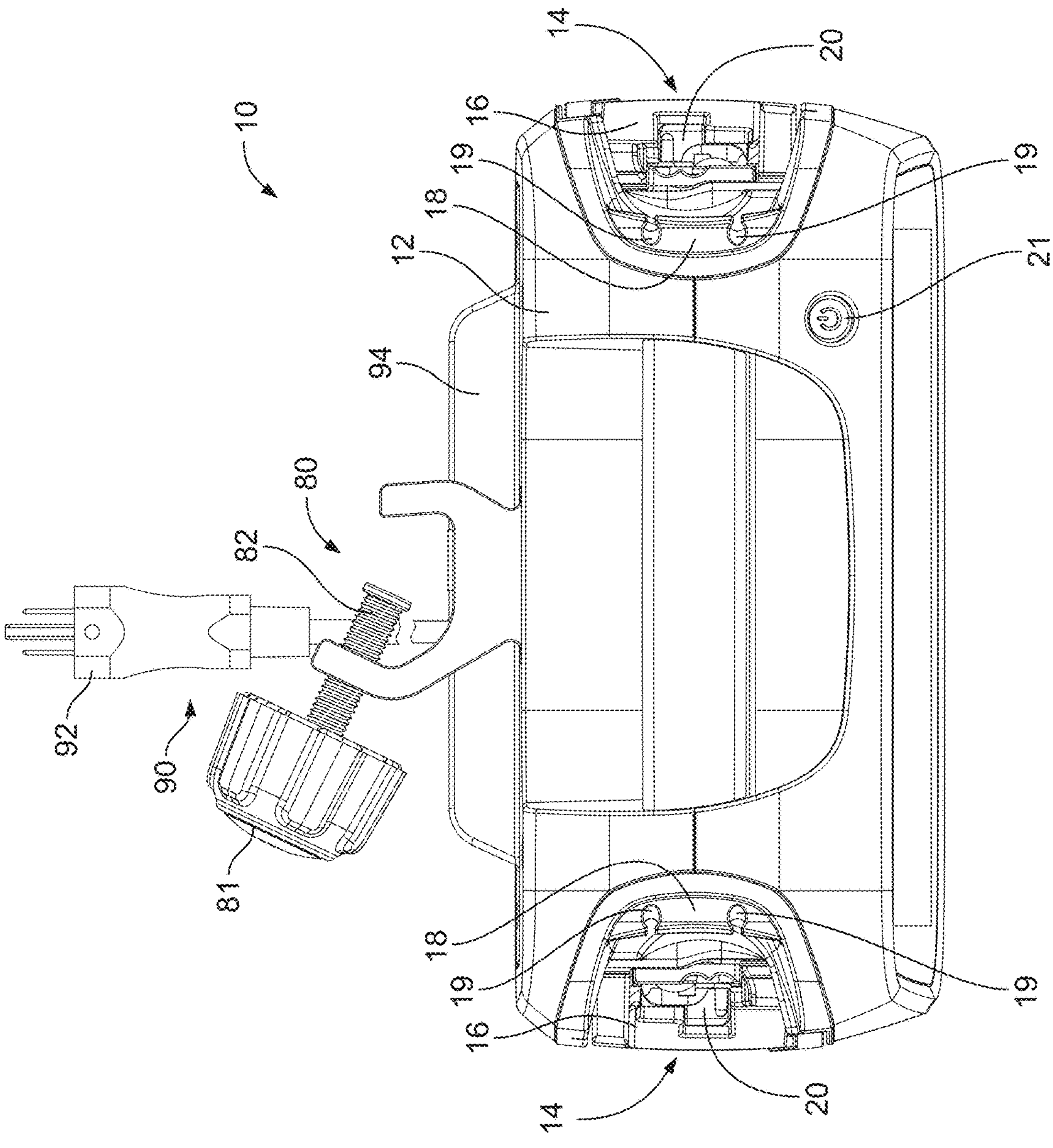
Figure 1E:
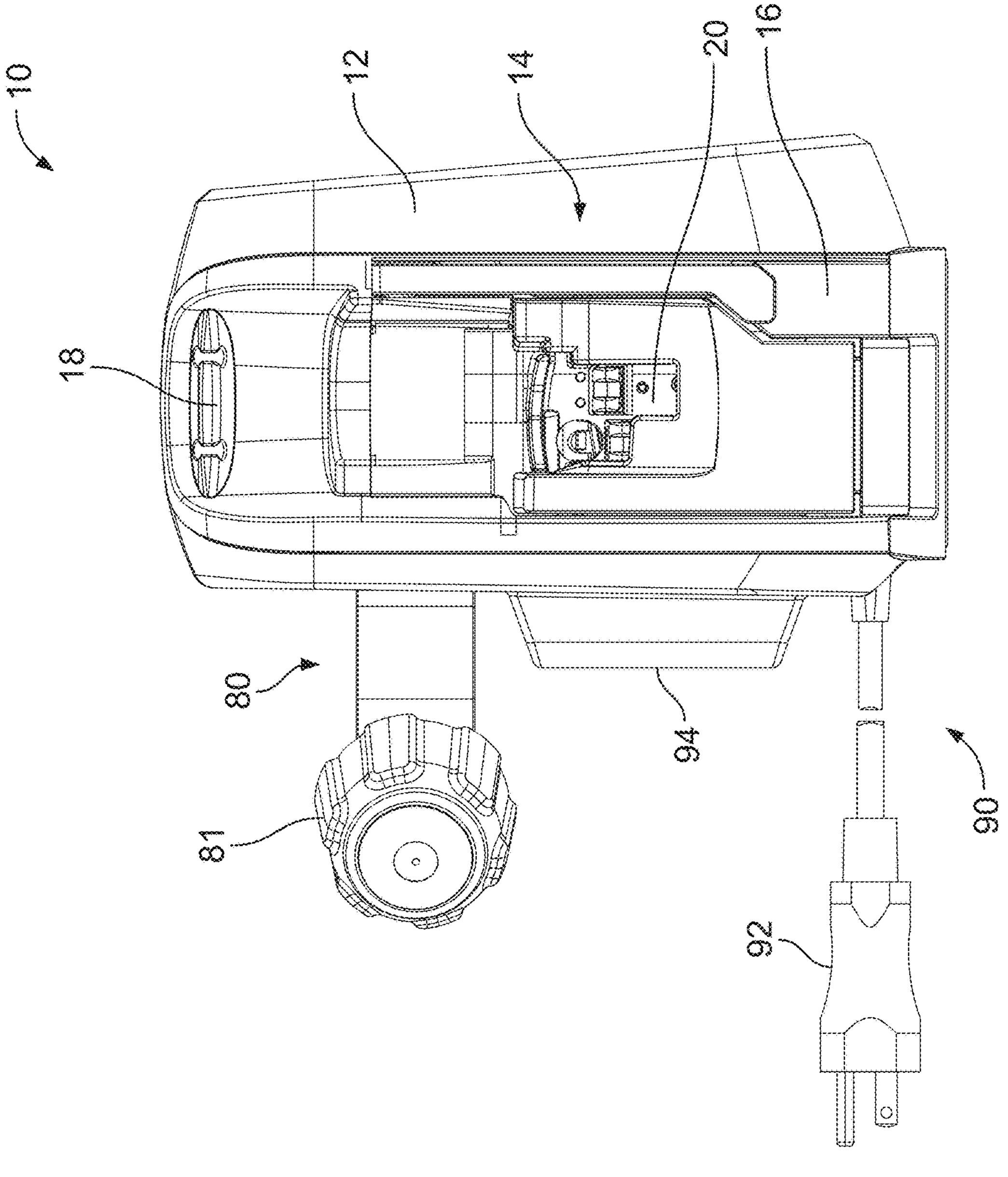

This specification provides textual descriptions and illustrations of many devices, components, assemblies, and subassemblies. Any structure, material, function, method, or step that is described and/or illustrated in one example can be used by itself or with or instead of any structure, material, function, method, or step that is described and/or illustrated in another example or used in this field. The text and drawings merely provide examples and should not be interpreted as limiting or exclusive. No feature disclosed in this application is considered critical or indispensable. The relative sizes and proportions of the components illustrated in the drawings form part of the supporting disclosure of this specification but should not be considered to limit any claim unless recited in such claim.

Various techniques for facilitating communication with and across a clinical environment and a cloud environment are also described herein. These techniques may include converting pump messages into standardized dataset messages (also referred to herein simply as “messages”), updating drug libraries, updating pump operational software, detecting health status parameters, sending health status parameters, among others. These and other embodiments are described in greater detail below with reference to FIGS. 6-13. Although many of the examples are described in the context of a hospital environment including infusion pumps, the techniques described herein can be applied to any network environment including other medical devices (e.g., patient care monitors configured to display blood pressure, heart rate, blood oxygenation, and the like), or non-medical devices, or any combination thereof.

A distributed system can include a server outside of a clinical environment and a connectivity adapter (optional) and a plurality of infusion pumps within the clinical environment. The optional connectivity adapter can receive from the server a location of an update, such as a drug library update or an operational software update, to be delivered to the infusion pumps. The location can be received over a first messaging communication channel of a network, and the update data can be received over a second, data communication channel of the network. The update data can be stored at the connectivity adapter such that it can be sent to the infusion pumps, or the update data may be sent directly to the infusion pumps.

A system can include a plurality of infusion pumps and an optional connectivity adapter in a clinical environment. The connectivity adapter can receive update data, such as a drug library update or an operational software update and can store the update data within the clinical environment. In some cases, the update data is received directly the infusion pump from the server. The connectivity adapter can send the update data to a predetermined number of infusion pumps that have requested the update. At least two subsets of the infusion pumps can receive different blocks of the update data at about the same time. Further, the same or different update data can be provided to the infusion pumps at about the same time.

Examples of Pump Systems

In some embodiments, a pump system can include a reusable pump driver and a disposable fluid holder, such as a fluid cassette, syringe, section of tubing, etc. A disposable cassette, which is typically adapted to be used only for a single patient and/or only for one fluid delivery cycle, is usually a small plastic unit having at least one inlet and an outlet respectively connected through flexible tubing to the fluid supply container and to the patient receiving the fluid. In some embodiments, the cassette can include a pumping chamber. The flow of fluid through the chamber can be controlled by a plunger or pumping element activated in a controlled manner by the reusable pump driver. For example, the cassette chamber can have one wall formed by a flexible diaphragm against which the plunger is repeatedly pressed in a reciprocating manner, which causes the fluid to flow. The pump driver can include the plunger or pumping element for controlling the flow of fluid into and out of the pumping chamber in the cassette, and it may also include one or more controls and/or vents to help deliver the fluid to the patient at a pre-set rate, in a pre-determined manner, for a particular pre-selected time, and/or at a pre-selected total dosage.

In some embodiments, the fluid can enter a cassette through an inlet and can be forced through an outlet under pressure. The fluid is delivered to the outlet when the pump plunger forces the membrane into the pumping chamber to displace the fluid. During the intake stroke, the pump plunger draws back, the membrane covering the pumping chamber retracts or pulls back from its prior inwardly displaced position, and the fluid is then drawn through the open inlet and into the pumping chamber. In a pumping stroke, the pump plunger forces the membrane back into the pumping chamber to force the fluid contained therein through the outlet. By repeating this action in an electronically controlled manner, the fluid flows into and out of the cassette in a series of spaced-apart pulses rather than in a continuous flow. When the pulses occur in rapid succession, the flow approximates a continuous flow. The entire disclosure of U.S. Pat. No. 7,258,534 is incorporated by reference herein, for all purposes, for all that it contains, including but not limited to examples of pump drivers and disposable fluid holders. It is contemplated that any structure, material, function, method, or step that is described and/or illustrated in the '534 patent can be used with or instead of any structure, material, function, method, or step that is described and/or illustrated in the text or drawings of this specification.

Examples of Pump System Components

FIGS. 1A-1E show an electronic medical intravenous pump 10 with a housing 12 and at least one pump driver 14 attached to the housing 12. As illustrated, a plurality of pump drivers 14 (e.g., at least two) can be integrally provided, contained, and/or partially contained, within the same housing 12 of a single medical pump 10. Either or both of the pump drivers 14 can include a cover 16 that partially or entirely encloses an outer surface of the pump driver 14, an indicator 18 (e.g., an illuminating communicator) attached to the cover 16, one or more tube holders 19, and a loader 20 configured to securely receive and releasable hold a disposable fluid holder (see, e.g., FIG. 2), including but not limited to a cassette, syringe, and/or tubing. The one or more tube holders 19 can be configured to removably receive and securely hold one or more fluid-conveying tubes extending into or exiting from fluid holder when the fluid holder is received into the loader 20. The indicator 18 can communicate one or more messages to a user, such as by temporarily illuminating in one or more colors. Examples of one or more messages include confirming that a pump driver 14 near the indicator is currently active and pumping or that one or more instructions being received from a user will apply to a pump driver 14 near the indicator 18. The loader 20 can be a mechanism with multiple moving parts that opens, closes, expands, contracts, clasps, grasps, releases, and/or couples with the fluid holder to securely hold the fluid holder on or within the pump 10 during fluid pumping into the patient. The loader 20 can be integrated into and positioned on or within the pump 10 near the cover 16 adjacent to the indicator 18.

A user communicator, such as display/input device 200, can be provided to convey information to and/or receive information from a user (e.g., in an interactive manner). As illustrated, the user communicator is a touch screen that is configured to provide information to a user through an illuminated dynamic display and is configured to sense a user's touch to make selections and/or to allow the user to input instructions or data. For example, the display-input device 200 can permit the user to input and see confirmation of the infusion rate, the volume of fluid to be infused (VTBI), the type of drug being infused, the name of the patient, and/or any other useful information. The display-input device 200 can be configured to display one or more pumping parameters on a continuing basis, such as the name of the drug being infused, the infusion rate, the volume that has been infused and/or the volume remaining to be infused, and/or the elapsed time of infusion and/or the time remaining for the programmed course of infusion, etc. As shown, the touch screen can be very large, for example at least about 4 inches×at least about 6 inches, or at least about 6 inches×at least about 8 inches. In the illustrated example, the touch screen fills substantially the entire front surface of the pump 10 (see FIG. 1A), with only a small protective boundary surrounding the touch screen on the front surface. As shown, the touch screen comprises at least about 80% or at least about 90% of the surface area of the front of the pump 10. In some implementations, the front of the touch screen comprises a clear glass or plastic plate that can be attached to the housing 20 in a manner that resists liquid ingress, such as using a water-proof gasket and/or adhesive that can withstand repeated exposure to cleaning and sanitizing agents commonly used in hospitals without significant degradation.

An actuator 21 can be provided separate from the user communicator. The actuator 21 can be configured to receive an input and/or display information to a user. As shown, the actuator 21 is a power button that permits the user to press on the actuator 21 to power up the pump 10. The actuator 21 can illuminated to communicate to the user that the pump 10 is power on. If the power source is running low, the actuator 21 can change the color of illumination to quickly show to a user that a power source needs to be replenished.

In some embodiments, the user communicator, such as a display/input device 200, can alternatively or additionally comprise one or more screens, speakers 502, lights, haptic vibrators 504, electronic numerical and/or alphabetic readouts, keyboards, physical or virtual buttons, capacitive touch sensors, microphones, and/or cameras, etc.

During use, the pump 10 is typically positioned near the patient who is receiving fluid infusion from the pump 10, usually lying in a bed or sitting in a chair. In some embodiments, the pump 10 may be configured to be an ambulatory pump, which will typically include a smaller housing, user communicator, battery, etc., so as to be conveniently transportable on or near a mobile patient. In many implementations, the pump 10 is attached to an IV pole stand (not shown) adjacent to the patient's bed or chair. As shown, the pump 10 can include a connector 80 that is configured to removably attach the pump 10 to the IV pole stand. As shown, the connector 80 can comprise an adjustable clamp with a large, easily graspable user actuator, such as a rotatable knob 81, that can be configured to selectively advance or retract a threaded shaft 82. At an end of the shaft 82 opposite from the knob 81 is a pole-contacting surface that can be rotatably advanced by the user to exert a force against a selected region of the pole, tightly pushing the pole against a rear surface of the pump 10, thereby securely holding the pump 10 in place on the pole during use. The selected region of the pole where the contacting surface of the shaft 82 is coupled can be chosen so as to position the pump 10 at a desired height for convenient and effective pumping and interaction with the patient and user.

The pump 10 can include a power source 90. In some embodiments, the power source can comprise one or more channels for selectively supplying power to the pump 10.

For example, as illustrated, the power source 90 can comprise an electrical cable 92 configured to be attached to an electrical outlet and/or a portable, rechargeable battery 94. One or more components of the pump 10 can operate using either or both sources of electrical power. The electrical cable 92 can be configured to supply electrical power to the pump 10 and/or supply electrical power to the battery 94 to recharge or to maintain electrical power in the battery 94.

Inside of the housing 20 of the pump 10, various electrical systems can be provided within the housing to control and regulate the pumping of medical fluid by the pump 10 into the patient and/or to communicate with the user and/or one or more other entities. For example, the pump 10 can include a circuit board with a processor that includes a user interface controller (UIC) that is in electronic communication with and is configured to control and interact with a user interface, such as a graphical user interface, that can be displayed on the user communicator or display/input device 200. The pump 10 can include a printed circuit board with a processor that includes a pump motor controller (PMC) that is in electronic communication with an is configured to control one or more pump drivers 14. In some embodiments, the PMC is located on a separate circuit board from the UIC and/or the PMC is independent from and separately operable from the UIC, each of the PMC and UIC including different electronic processors capable of concurrent and independent operation. In some embodiments, there are at least two PMC's provided, a separate and independent one for each pump driver 14, capable of concurrent and independent operation from each other. The pump 10 can include a printed circuit board with a processor that includes an electronic controller that comprises a communications engine (CE) in electrical communication with a communicator that enables and controls electronic communications between the pump 10 and other entities (aside from the user), such as electronic, wired or wireless, communication with a separate or remote user, computer, computer system, server, hospital electronic medical records system, remote healthcare provider, router, network, another pump, a mobile electronic device, a near field communication (NFC) device such as a radio-frequency identification (RFID) device, and/or a central computer controlling and/or monitoring multiple pumps 10, etc. The CE can include or can be in electronic communication with an electronic transmitter, receiver, and/or transceiver capable of transmitting and/or receiving electronic information by wire or wirelessly (e.g., by Wi-Fi, Bluetooth, cellular signal, etc.). In some embodiments, the CE, PMC(s), and/or the UIC are each located on a separate circuit board and in a different location within the housing from one or more of the others. One or more of the CE, PMC(s), and/or the CE can be independent from and separately operable from either or both of the others, each of the PMC(s), UIC, and CE including different electronic processors capable of parallel, concurrent, and/or independent operation. In some embodiments, any, some, or all of the UIC, CE, and PMC(s) are capable of operational isolation from any, some, or all of the others such that it or they can turn off, stop working, encounter an error or enter a failure mode, reboot, and/or reset, without interrupting, turning off, operationally affecting, and/or without detrimentally affecting the operation of any, some, or all of the others. In such an operationally isolated configuration, any, some, or all of the UIC, CE, and PMC(s) can still be in periodic or continuous data transfer or communication with any, some, or all of the others. The UIC, PMC(s), and/or CE can be operationally isolated, and/or physically or functionally separated, and still be configured within the housing 20 of the pump 10 to be in electronic communication with each other, transmitting data and/or instructions between or among each of them as needed. While functioning properly in the normal course of operations, any, some, or all of the UIC, CE, and PMC(s) can operate in simultaneous, real-time parallel and/or concurrent processing modes, such that any, some, or all of the UIC, CE, and PMC(s) are capable of performing different operations and tasks at generally the same time.

In some embodiments, any or all information, instructions, and/or programming entered by a user in the UIC can be evaluated, checked, and/or validated for effectiveness and safety for the patient before such information, instructions, and/or programming is conveyed, in whole or in part, or results in any signal or instruction being sent by the UIC to the PMC and/or the CE. The user is not typically permitted to modify, remove, and/or change system architecture or operating systems.

Figure 2:
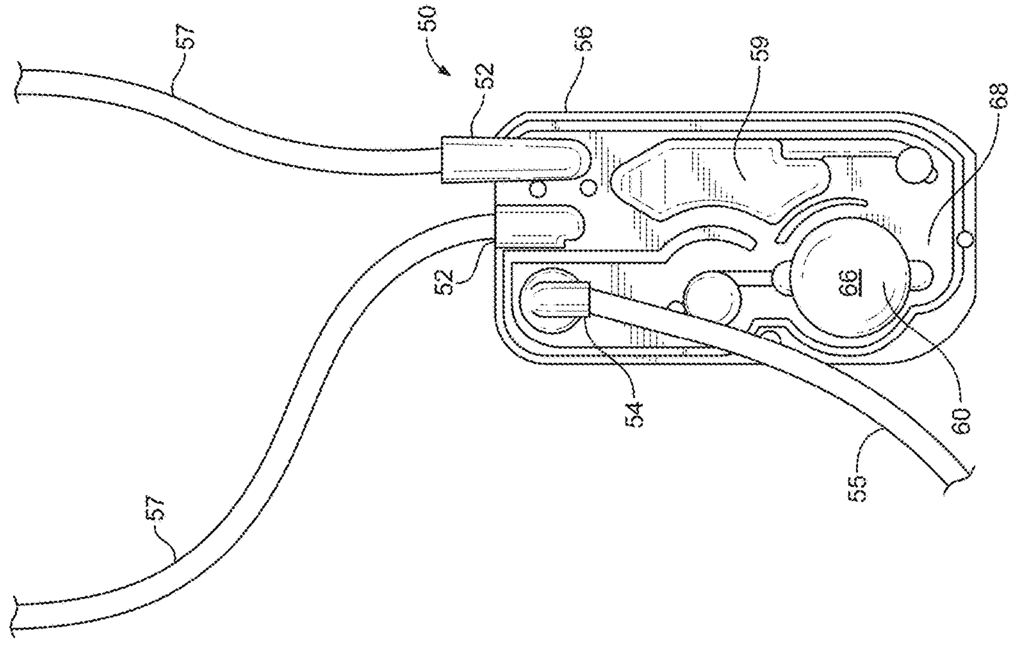
FIG. 2 shows an example of a cassette that can be used with the pump of FIG. 1.

FIG. 2 shows an example of a disposable fluid holder, such as a disposable cassette 50, that includes a plastic housing and a flexible, elastomeric silicon membrane. Any structure, material, function, method, or step that is described and/or illustrated in U.S. Pat. No. 4,842,584, which is incorporated herein by reference in its entirety, including but not limited to the pumping cassette, can be used by itself or with or instead of any structure, material, function, method, or step that is described and/or illustrated in this specification. The plastic housing of the cassette 50 can include one or more (e.g., two as shown) fluid inlets 52 and a fluid outlet 54 formed in a main body 56. The cassette 50 can be temporarily positioned for example in the loader 20 of a pump driver 14. The one or more fluid inlets 52 are coupled with one or more inlet tubes 57 in fluid communication with one or more sources of medical fluid, such as one or more IV bags, vials, and/or syringes, etc., containing medical fluid. If multiple inlets 52 and inlet tubes 57 are provided, as shown, then multiple sources of medical fluid can be simultaneously supplied to a patient through the cassette 50. The fluid outlet 54 is coupled to an outlet tube 55 in fluid communication with the patient, normally by way of a needle leading into a patient's blood vessel.

A flexible, elastomeric membrane forms a diaphragm 60 within a pumping chamber 66 on an inner face 68 of the main body 56. In operation, fluid enters through one or more of the inlets 52 and is forced through the outlet 54 under pressure. One or more fluid channels within the main body 56 of the cassette 50 convey the fluid between the inlets 52 and the outlet 54 by way of the pumping chamber 66. Before use, the cassette is typically primed with fluid, usually saline solution. A volume of fluid is delivered to the outlet 54 when a plunger 136 of the pump 10 (see, e.g., FIG. 3A) displaces the diaphragm to expel the fluid from the pumping chamber 66. During an intake stroke, the plunger 136 retracts from the diaphragm 60, and the fluid is then drawn in through the inlet 52 and into the pumping chamber 66. In a pumping stroke, the pump 10 displaces the diaphragm 60 of the pumping chamber 66 to force the fluid contained therein through the outlet 54. In some embodiments, the directional movement of flow can be facilitated by one or more directional valve(s) (e.g., at one or more of inlet 52 or outlet 54). The fluid can flow from the cassette 50 in a series of spaced-apart pulses rather than in a continuous flow. In some embodiments, the pump 10 can deliver fluid to a recipient (e.g., a patient) at a pre-set rate, in a pre-determined manner, and for a particular (e.g., pre-selected) time or total dosage. The cassette 50 can include an air trap 59 in communication with an air vent (not shown).

Figure 3A:
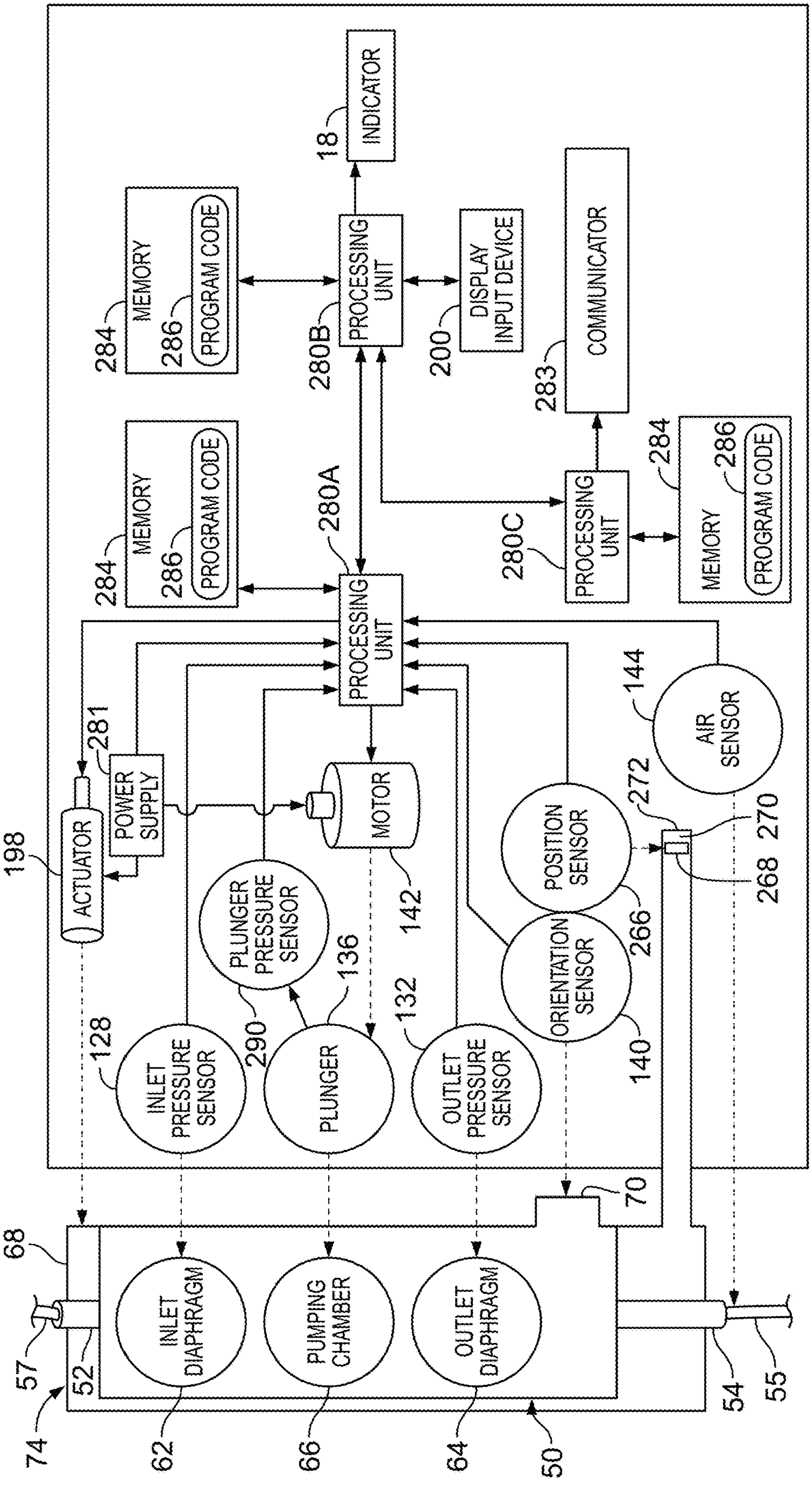
FIG. 3A shows a schematic diagram of functional components for an example of a medical pump system.

FIG. 3A is a schematic diagram of functional components for a medical pump (e.g., the pump 10 of FIG. 1) used in connection with the disposable cassette 50 (see FIG. 2) for delivering a fluid to a patient. One or more processors or processing units 280 can be included in pump 10 that can perform various operations, some examples of which are described in greater detail below. The processing unit(s) 280 and all other electrical components within the pump 10 can be powered by a power supply 281, such as one or more components of power source 90 of pump 10. In some embodiments, the processing unit 280*a* can be configured as a pump motor controller (PMC) to control the electric motor 142 being energized by the power supply 281. When energized, the electric motor 142 can cause the plunger 136 to reciprocate back and forth to periodically actuate, press inward, and/or down-stroke, causing plunger 136 to temporarily press on pumping chamber 66, driving fluid through cassette 50. The motor 142, plunger 136, sensors 128, 290, 132, 140, 266, 144 can be included in or as an integrated part of the pump driver 14 of the pump 10. In some embodiments, as shown, the inlet pressure sensor 128 engages the inlet diaphragm 62 of cassette 50, and the outlet pressure sensor 132 engages the outlet diaphragm 64 of cassette 50. When retracting, moving outward, or on an up-stroke, the plunger 136 can release pressure from pumping chamber 66 and thereby draw fluid from inlet 52 into pumping chamber 66. In some implementations of cassette 50, a flow stop 70 is formed as a pivotal switch in the main body 56 and protrudes a given height from the inner surface 68. This protrusion forms an irregular portion of the inner surface 68 which can be used in some embodiments to align the cassette 50 as well as monitor the orientation of the cassette 50. In some embodiments, one form of a flow stop 70 can provide a manual switch or valve for closing and opening the cassette 50 to fluid flow.

In some embodiments, the processing unit 280*a* can control a loader 20 of the pump 10 with an electronic actuator 198 and a front carriage being energized by the power supply 281. When energized, the actuator 198 can drive the front carriage 74 between closed or open positions. The front carriage 74 in the open position can be configured to receive the cassette 50 and in the closed position can be configured to temporarily securely retain the cassette 50 until the front carriage is moved to the closed position. A position sensor 266 for the cassette 50 can be provided in the pump 10. The position sensor 266 can monitor the position of a slot 268 formed in a position plate 270. The position sensor 266 can monitor a position of an edge 272 of a position plate 270 within the pump 10. By monitoring the position of the position plate 270, the position sensor 266 can detect the overall position of the front carriage of the loader 20. The position sensor 266 can be a linear pixel array sensor that continuously tracks the position of the slot 268. Of course, any other devices can be used for the position sensor 266, such as an opto-tachometer sensor.

A memory 284 can communicate with the processing unit 280*a* and can store program code 286 and data necessary or helpful for the processing unit 280 to receive, determine, calculate, and/or output the operating conditions of pump 10. The processing unit 280*a* retrieves the program code 286 from memory 284 and applies it to the data received from various sensors and devices of pump 10. The memory 284 and/or program code 286 can be included within or integrally attached to (e.g., on the same circuit board) as the processing unit 280*a*, which in some embodiments can be the configuration for any processor or processing unit 280 in this specification.

In some embodiments, the program code 286 can control the pump 10 and/or track a history of pump 10 operation details (which may be recorded and/or otherwise affected or modified, e.g., in part by input from sensors such as air sensor 144, position sensor 266, orientation sensor 140, outlet pressure sensor 132, plunger pressure sensor 290, inlet pressure sensor 128, etc.) and store and/or retrieve those details in the memory 284. The program code 286 can use any one or more of these sensors to help identify or diagnose pumping problems, such as air in a pumping line, a pumping obstruction, an empty fluid source, and/or calculate expected infusate arrival time in a patient. The display/input device 200 can receive information from a user regarding a patient, one or more drugs to be infused, and details about a course of infusion into a patient. The display/input device 200 can provide a clinician with any useful information regarding the pumping therapy, such as pumping parameters (e.g., VTBI, remaining volume, infusion rate, time for infusion, elapsed time of infusion, expected infusate arrival time, and/or time for completion of infusion, etc.) Some or all of the information displayed by the display/input device 200 can be based on the operation details and calculations performed by the program code 286.

In some embodiments, the operation details can include information determined by the processing unit 280*a*. The processing unit 280*a* can process the data from pump 10 to determine some or all of the following operating conditions: whether or when the cassette 50 has been inserted, whether or when the cassette 50 is correctly oriented, whether or when the cassette 50 is not fully seated to the fixed seat 162, whether or when the front carriage assembly 74 is in an open or closed position, whether or when a jam in the front carriage assembly 74 is detected, whether or when there is proper flow of fluid through the cassette 50 to the patient, and whether or when one or more air bubbles are included in the fluid entering, within, and/or leaving cassette 50. The processing unit 280*a* can be configured to determine one or more operating conditions to adjust the operation of the pump 10 to address or improve a detected condition.

For example, the processing unit 280*a* can receive data from a plunger pressure sensor 290 operatively associated with the plunger 136. The plunger pressure sensor 290 can sense the force on plunger 136 and generate a pressure signal based on this force. The plunger pressure sensor 290 can communicate with the processing unit 280*a*, sending the pressure signal to the processing unit 280*a* for use in helping to determine operating conditions of pump 10.

The processing unit 280*a* can receive an array of one or more items of pressure data sensed from the cassette inner surface 68 determined by the plunger pressure sensor 290 and inlet and outlet pressure sensors 128 and 132. The processing unit 280*a* can combine the pressure data from the plunger pressure sensor 290 with data from inlet and outlet pressure sensors 128 and 132 to provide a determination as to the correct or incorrect positioning of cassette 50. In normal operation, this array of pressure data falls within an expected range and the processing unit 280*a* can determine that proper cassette loading has occurred. When the cassette 50 is incorrectly oriented (e.g., backwards or upside down) or when the cassette 50 is not fully seated to the fixed seat 162, one or more parameters or data of the array of pressure data falls outside the expected range and the processing unit 280*a* determines that improper cassette loading has occurred.

As shown, in some embodiments, the processing unit 280*a* can receive data from one or more air sensors 144 in communication with outlet tube 55 attached to the cassette outlet 54. An air sensor 144 can be an ultrasonic sensor configured to measure or detect air or an amount of air in or adjacent to the outlet 54 or outlet tube 55. In normal operation, this air content data falls within an expected range, and the processing unit 280*a* can determine that proper fluid flow is in progress. When the air content data falls outside the expected range, the processing unit 280*a* can determine that improper air content is being delivered to the patient.

Processing unit 280*a* can continuously or periodically communicate with an independent and separate processor or processing unit 280*b* to communicate information to the user and/or to receive data from the user that may affect pumping conditions or parameters. For example, processing unit 280*a* can communicate by wire or wirelessly with processing unit 280*b* which can be configured as a user interface processor or controller (UIC) to control the output and input of display/input device 200, including by displaying an operating condition and/or activate indicator 18 to communicate with a user. In some embodiments, processing unit 280*b* can receive user input regarding pumping conditions or parameters, provide drug library and drug compatibility information, alert a user to a problem or a pumping condition, provide an alarm, provide a message to a user (e.g., instructing a user to check the line or attach more fluid), and/or receive and communication information that modifies or halts operation of the pump 10.

An independent and separate processor or processing unit 280*c* can be configured as a communications engine (CE) for the pump, a pump communications driver, a pump communications module, and/or a pump communications processor. Processing unit 280*c* can continuously or periodically communicate with processing units 280*a* and 280*b* to transmit and/or receive information to and from electronic sources or destinations separate from, outside of, and/or remote from, the pump 10. As shown, processing unit 280*c* can be in electronic communication with or include a memory 284 and program code 286, and processing unit 280*c* can be in communication with and control data flow to and from a communicator 283 which can be configured to communicate, wired or wirelessly, with another electronic entity that it separate from the pump 10, such as a separate or remote user, a server, a hospital electronic medical records system, a remote healthcare provider, a router, another pump, a mobile electronic device, a near field communication (NFC) device such as a radio-frequency identification (RFID) device, and/or a central computer controlling and/or monitoring multiple pumps 10, etc.

As shown schematically in FIG. 3A, a pump 10 can be provided with many components to accomplish controlled pumping of medical fluid from one or more medical fluid sources to a patient. For example, one or more processors or processing units 280 can receive various data useful for the processing unit(s) 280 to calculate and output the operating conditions of pump 10.

The processing unit(s) 280 can retrieve the program code 286 from memory 284 and apply it to the data received from various sensors and devices of pump 10, and generate output(s). The output(s) are used to communicate to the user by the processing unit 280*b*, to activate and regulate the pump driver by the processing unit 280*a*, and to communicate with other electronic devices using processing unit 280*c*.

Figure 3B:
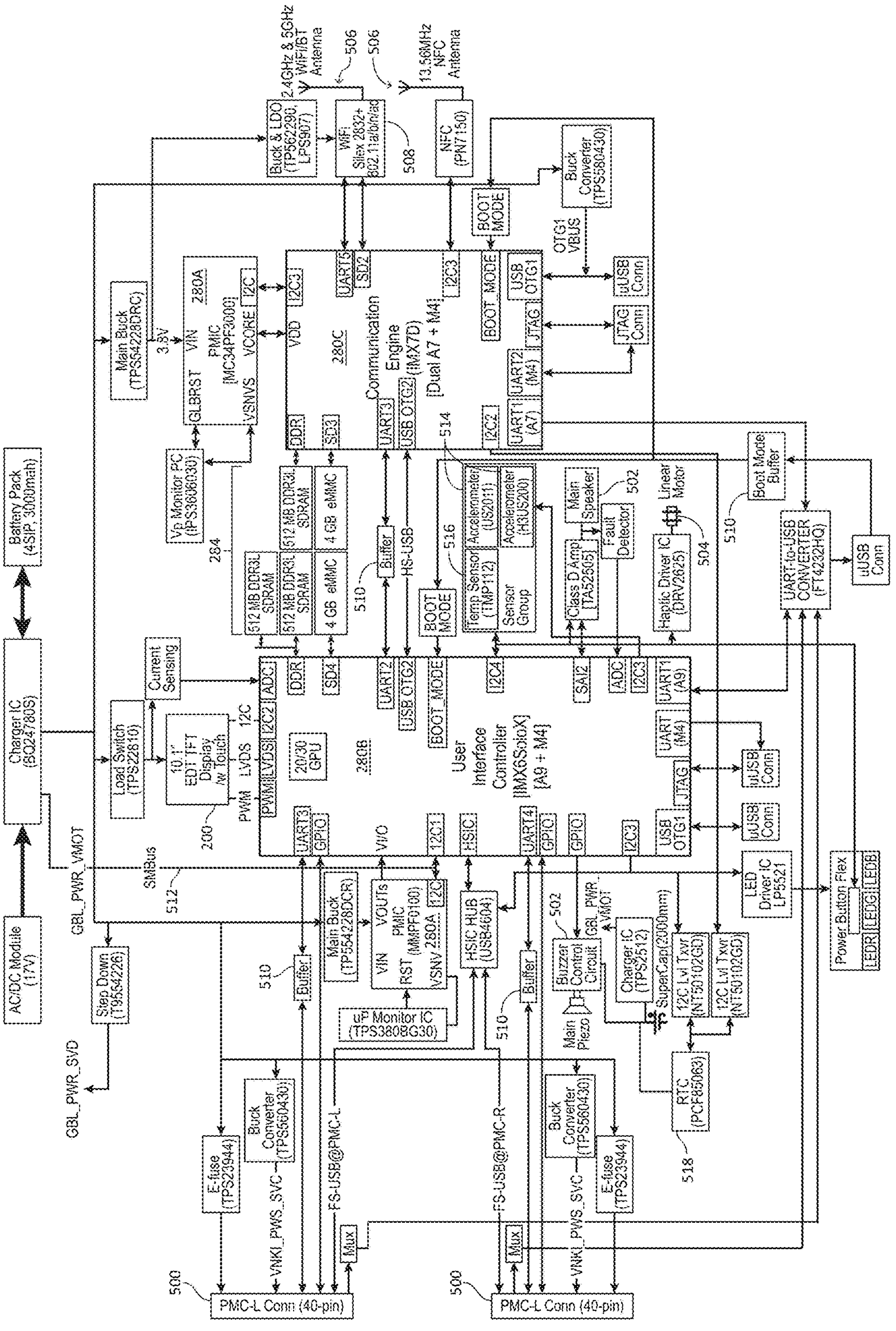
FIG. 3B shows a schematic diagram of electronic components and circuitry for an example of a medical pump system.

FIG. 3B illustrates various examples of electronic components and circuitry that can be provided in electronic communication with each other as shown within the pump 10 with examples of electrical interconnections as shown. As illustrated, all components and circuitry in this example are located inside of the housing 12 of the pump 10. In some embodiments, one or more of the components and/or portions of the circuitry can be located outside of the housing 12 and/or in another housing or device.

As shown in part in FIG. 3B, the communicator 283 or any other portion of the electronics of the pump 10 can be or can comprise one or more of a wire, a bus 512, a receiver, a connector port 500, a transmitter, a transceiver 508, a modem, a codec, an antenna 506, a buffer 510, a multiplexer, a network interface, a router, and/or a hub, etc. The communicator 283 can communicate with another electronic entity in any suitable manner, such as by wire, short-range wireless protocol (Wi-Fi, Bluetooth, ZigBee, etc.), fiber optic cable, cellular data, satellite transmission, and/or any other appropriate electronic medium.

The pump 10 can comprise one or more sensors for determining general operating conditions and/or general standing conditions and/or physical movement of the pump 10. For example, as shown in FIG. 3B, the pump 10 can comprise one or more accelerometers 514 and/or one or more temperature sensors 516. In some embodiments, one of the accelerometers 514 can be configured to detect a falling motion of the pump 10, such as when the pump 10 is dropped or when a pole stand tips over with the pump 10 attached, and another of the accelerometers 514 can be configured to detect the severity of an impact (e.g., "G-shock") when the pump 10 hits the floor or another object during or after a fall. In some implementations, the same accelerometer 514 can be configured to detect both falling and impact severity. One or more of the accelerometers 514 can be in electronic communication with the UIC processor 280*b* as shown in FIG. 3B. The processor 280*b* can be configured to receive one or more electrical signals from one or both of the accelerometers 514 that can enable the processor 280*b* to determine that a fall occurred and/or that can provide various data about a fall of the pump 10, such as the magnitude of the acceleration during the fall, the time duration of the fall, the occurrence of one of more impacts in the fall, and/or the force of impact(s) from the fall.

The processor 280*b* can be configured to record the date and time when the fall occurred and store this information, along with one or more items of data from the accelerometers regarding the fall, in a memory 284. The processor 280*b* can communicate any or all fall data to the CE processor 280*c* which can be configured to send an electronic notice or message to any other local or remote location that a fall occurred and/or to provide information about the fall. The processor 280*b* can communicate any or all fall data or another electronic signal to the PMC processor 280*a* which can, depending on the severity of the fall, cause the processor 280*a* to stop pumping and/or to refrain from pumping again until the pump 10 is fully inspected and/or repaired due to any damaged caused by the fall. The processor 280*b* can be configured to provide a warning or notification on the display 200 or via a speaker 502, haptic vibrator 504, indicator light, and/or by any other user-communication system or component to alert a user that a fall has occurred and/or that the pump 10 will not be permitted to function unless and until an inspection or repair occurs. In some embodiments, the processor 280*b* can require that an override authorization indicator such as a code, key, specialized tool, and/or other device or communication be provided by an authorized inspector and/or repair technician before the pump 10 will operate after a fall.

When the pump 10 is operating at full capacity, which may in some circumstances involve pumping fluid from either or both pumps, displaying information on a screen, charging the battery, and/or communicating information to or from a remote source, the aggregated heat output from all of these components can be significant. Also, if any component of the pump malfunctions in a way that increases its heat output, it can create a risk of damaging other components and/or degrading, altering, and/or halting the performance of the pump 10. Thus, monitoring and managing the temperature of the pump 10 can be advantageous.

The pump 10 can include one or more temperature sensors 516 that can comprise any suitable electronic component or components that is or are configured to measure and/or convey information about an air temperature inside or in the environment of the pump 10. For example, in some embodiments, a temperature-variable resistor or thermistor, a thermocouple, an infrared sensor, and/or a temperature-variable diode or transistor can be used to create an electrical signal indicative of temperature. The pump 10 can include one or more temperature sensors 516 within the housing 12 of the pump 10 or outside of the housing 12 of the pump. In some embodiments, a plurality of temperature sensors 516 can be provided within the housing 12 that are spaced apart from each other and/or are located strategically in one or more different places within the housing 12 that are vulnerable or prone to, or have a tendency toward, over-heating, such as proximate to the battery 94, the display 200, the pump motor(s) 242, and/or any other component or place where over-heating may occur.

The temperature sensor(s) 516 can be in electronic communication with the UIC processor 280*b* as shown in FIG. 3B. The processor 280*b* can be configured to determine when one or more temperature sensors 516 have detected that an acceptable operating temperature has been exceeded (e.g., equal to or greater than about 100 degrees Fahrenheit or 38 degrees Celsius). If the pump 10 includes multiple temperature sensors 516, the processor 280*b* can be configured to determine that one or more specified regions within the pump 10 have exceeded an acceptable operating temperature.

The processor 280*b* can automatically respond to an excess temperature indication from one or more temperature sensor(s) 516 in any suitable way, including: (a) providing a notice to the user on the display 200 that the pump 10 is overheating; (b) communicating to the processor 280*c*, which can communicate a notice outside of the pump, such as to a local or remote location, that the pump 10 is overheating; (c) storing in memory 284 information about an over-heating incident, including the duration and temperature range of the overheating period; (d) deactivating, turning-off, slowing down, modifying, and/or delaying, one or more functions or operations of the pump 10 that are considered to be non-critical and/or not time-sensitive, and/or that are considered to be significant causes of heat generation, such as electrical charging and/or sending or receiving communications outside of the pump 10 (e.g., updating software or data from an external source). In some embodiments, the brightness of the display 200 can automatically be diminished by the processor 280*b* if a temperature sensor 516 in the region of the display 200 detects a temperature in excess of a permissible level. The processor 280*b* can be configured to use a hierarchy of functionality in determining how to manage the modifications in response to an excess temperature detection, such as by modifying the least critical function(s) first and/or by modifying the function(s) performed in the region of a detected temperature increase first. When the processor 280*b* has performed a temperature-induced modification of functionality, and then later one or more of the temperature sensors 516 detects that the temperature has dropped to or below an acceptable level (e.g., less than or equal to about 100 degrees Fahrenheit or 38 degrees Celsius), any modified functionality in the pump 10 and/or in the region of the previously detected increase in temperature can be automatically stopped and the operation of the pump 10 can automatically return to normal.

Automated Pump Updating

Figure 4:
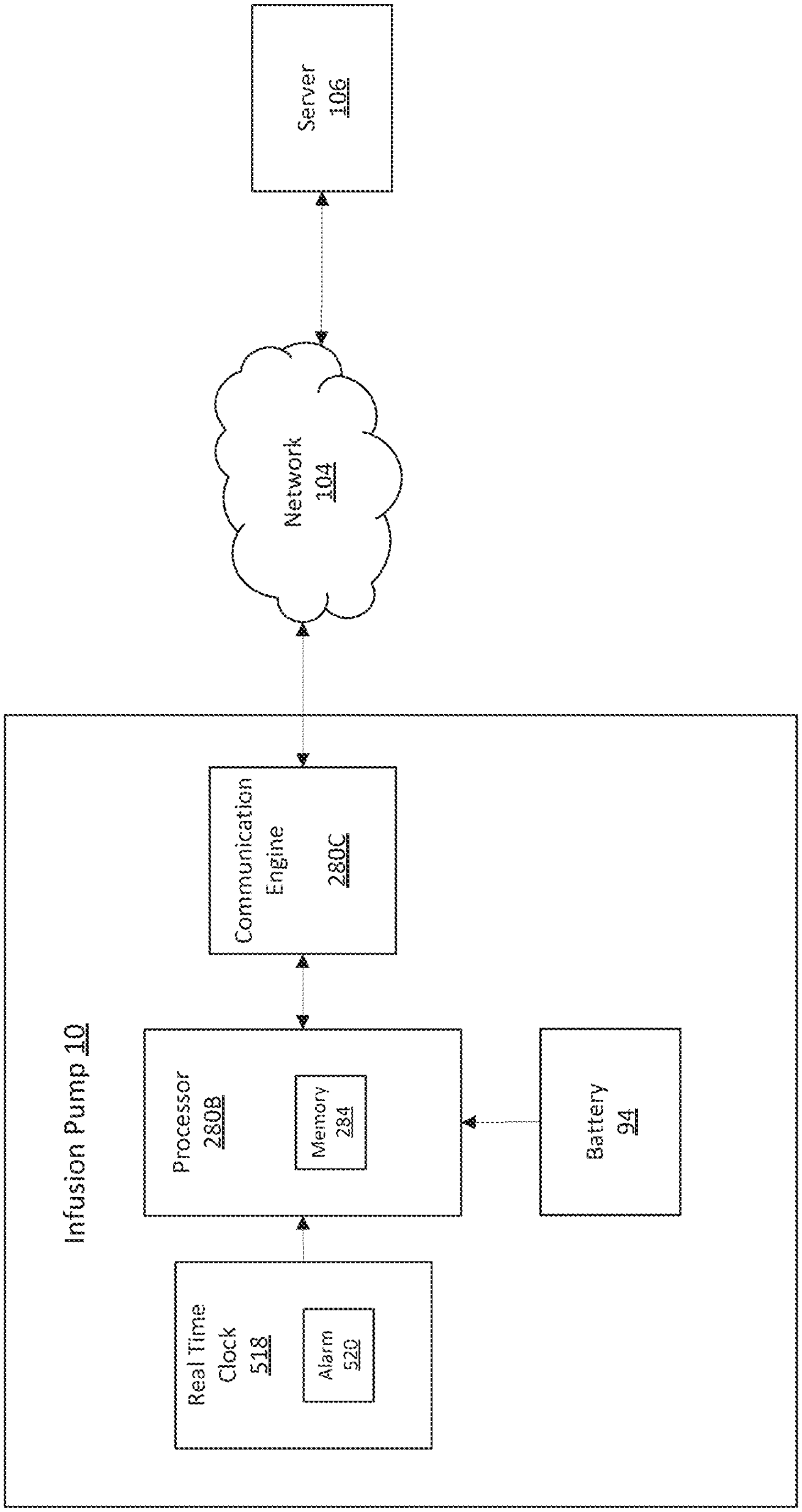
FIG. 4 shows a schematic diagram of a portion the medical pump system of FIGS. 3A-3B.

FIG. 4 illustrates one embodiment of an infusion pump configured for automated updating. The infusion pump can include any of the infusion pumps described herein, including but not limited to infusion pump 10 or infusion pump 204, although infusion pump 10 is shown in FIG. 4 for illustrative purposes. The infusion pump 10 may automatically update its operating software, drug library, or both, according to the method described with respect to FIG. 5, below.

The infusion pump 10 includes a real time clock (RTC) 518, a processor 280B, a communication engine 280C and a battery 94. The real time clock 518 includes circuits or software to execute an alarm function 520. The alarm 520 of the real time clock 518 can activate even when the infusion pump 10 is in an off state, where no power is supplied to the processor 280B or communication engine 280C, and the pump is not providing any therapy. For example, in the off state, the pump 10 may be unplugged from an AC power source and may be in a storage area waiting to be assigned to a patient.

During the off state, the real time clock 518 of the pump 10 may continue to operate. When a designated time occurs, or when a designated period passes, the real time clock 518 may send a signal or command to wake the processor 280B from its off state. In response to the signal or command, the processor 280B executes instructions stored in the memory 284 to determine whether to perform the automated updating procedure. The memory 284 is shown within the processor 280B in FIG. 4, but the memory 284 may be external to the processor 280B (as shown in FIG. 3B) or both, within and external to the processor 280B.

The instructions cause the processor to determine whether the pump 10 is in a state suitable for updating. For example, the processor 280B determines whether the pump 10 is connected to an AC power source, or whether it is receiving power from its internal, rechargeable battery 94. The processor 280B may also determine whether there is enough power or energy stored within the battery 94 to acquire and update the pump 10 with an update. If the pump 10 is receiving power from an AC power source, then the processor 280B determines that the pump is in a state suitable for updating. Similarly, if the pump 10 is receiving power from its battery 94 and if the battery 94 is storing enough power or energy to acquire and update the pump 10, then the processor 280B determines that the pump 10 is in a state suitable for updating. However, if the pump 10 is not storing enough power or energy to acquire and update the pump 10, then the processor 280B determines that the pump 10 is not in a state suitable for updating.

If the processor 280B determines that the pump 10 is in a state suitable for updating, the processor 280B sends a signal or command to wake the communication engine 280C from the off state. Staggering the waking of the processor 280B and communication engine 280C, and only waking the communication engine 280C if the pump is in a suitable state for updating, can save energy stored within the battery 94. The communication engine 280C can include a processor, such as any of the processors described herein. The communication engine 280C wakes and establishes a connection over a network 104 with a server 106 or a cloud environment 106, as discussed in further detail herein. The network 104 and server or cloud environment 106 can include any of the networks, servers or cloud environments described herein.

The server 106 may be referred to as a remote location. The communication engine 280C determines from the server 106 whether there is an update available for acquisition by the infusion pump 10. The update can include an operating software update, a drug library update, or both. If an update is available, the communication engine 280C acquires the update. For example, the infusion pump 10 may acquire the update according to any of the methods described below.

In one example, the communication engine 280C downloads the update from the server 106 or other remote location. In another example, the server 106 or other remote location sends or pushes the update to the infusion pump 10 via the communication engine 280C. Once received, the processor 280B installs the update. For example, the processor 280B may install the updated operating software or save the updated drug library to the memory 284 or other location within the infusion pump 10.

Figure 5:
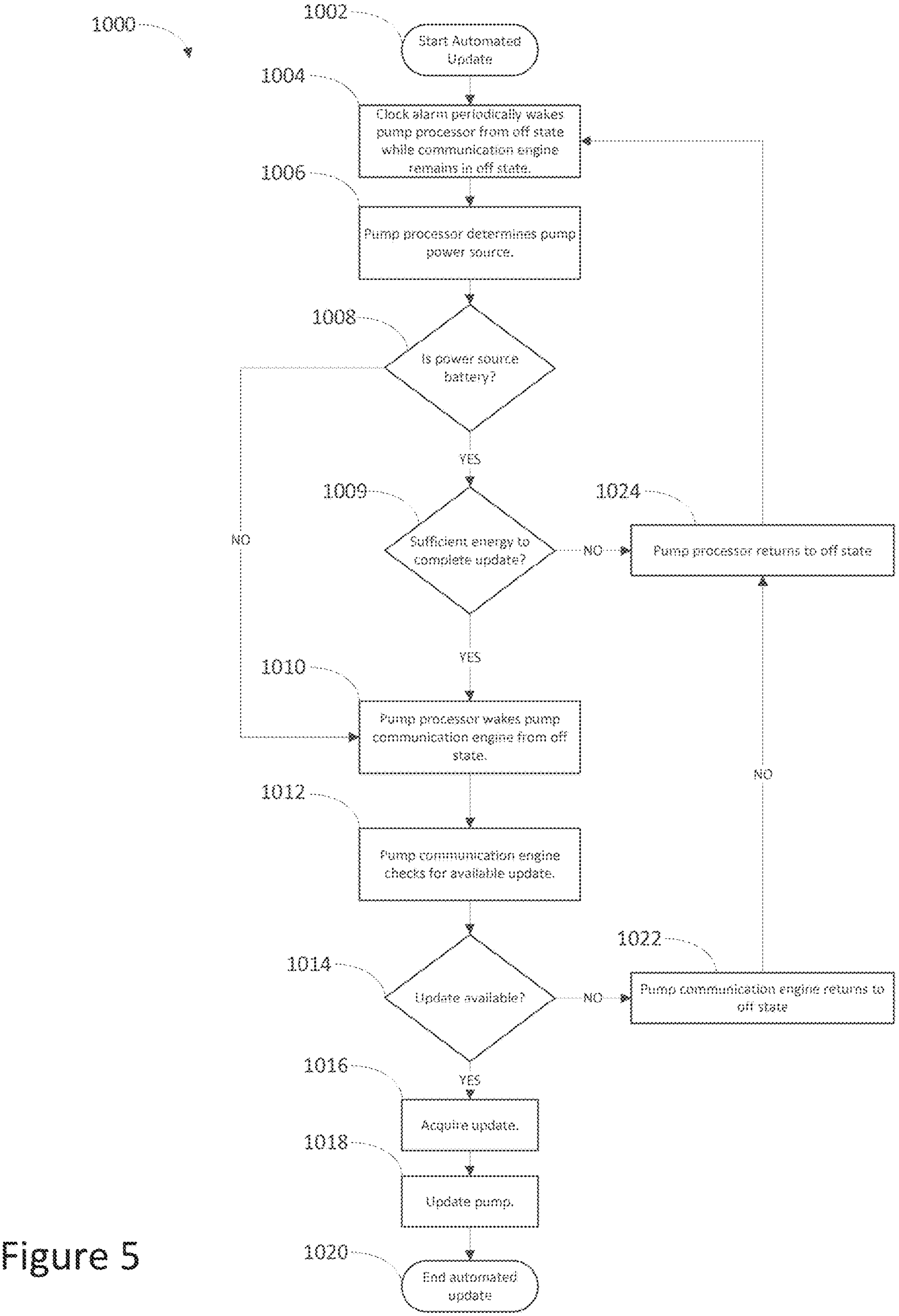
FIG. 5 is a flow chart of a method of automatically updating a medical pump system.

One embodiment of a method of automatically updating an infusion pump is shown in FIG. 5. The method 1000 begins at block 1002. At block 1004 the clock alarm wakes the pump processor from an off state. For example, all circuits within the infusion pump may be powered off, except for a clock, or real-time clock. The clock may have an alarm function that can periodically (e.g., once, twice, three times, four times, six times, ten times, or any other number of times per day, week month or any other time duration) send a signal to wake the pump processor from the off state for the purpose of checking for system software or drug library update availability. At block 1006, the pump processor determines the pump power source, such as whether the pump is powered by an AC power source or from a battery. At block 1008, the processor determines whether the power source is a battery. If it is, the method 1000 proceeds to block 1009. If it isn't, the method 1000 proceeds to block 1010. At block 1010, the pump processor determines whether the battery contains sufficient energy to complete a system software or drug library update. If the battery does contain sufficient energy, the method 1000 proceeds to block 1010. If not, the method 1000 proceeds to block 1024. At block 1024, the pump processor returns to its off state and the method 1000 returns to block 1004.

At block 1010, the pump processor wakes the pump's communication engine from an off state. At block 1012, the communication engine checks for an available update. At block 1014, if an update is available, the method 1000 continues to block 1016. If an update is not available, the method 1000 continues to block 1022. At block 1022, the pump communication engine returns to the off state and the method 1000 continues to block 1024, as discussed above.

At block 1016, the communication engine acquires the update. At block 1018, the processor updates the pump with the update. The update may include an operating software update or a drug library update. The method 1000 ends at block 1020.

Overview of Example Network Environment

Figure 6:
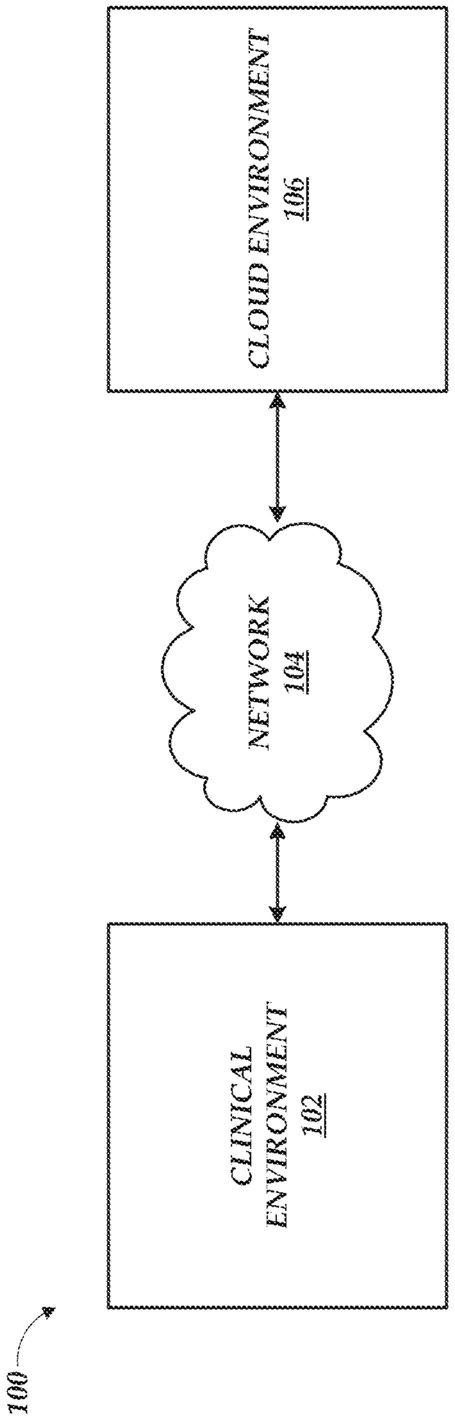
FIG. 6 is a block diagram of an example clinical environment and an example cloud environment.

FIG. 6 illustrates an example network environment 100 in which clinical environment 102 communicates with cloud environment 106 via network 104. The clinical environment 102 may include one or more healthcare facilities (e.g., hospitals). The components of the clinical environment 102 are described in greater detail below with reference to FIG. 7. The network 104 may be any wired network, wireless network, or combination thereof. In addition, the network 104 may be a personal area network, local area network, wide area network, over-the-air broadcast network (e.g., for radio or television), cable network, satellite network, cellular telephone network, or combination thereof. For example, the network 104 may be a publicly accessible network of linked networks such as the Internet. Protocols and components for communicating via the Internet or any of the other aforementioned types of communication networks are well known to those skilled in the art and, thus, are not described in more detail herein. For example, the clinical environment 102 and the cloud environment 106 may each be implemented on one or more wired and/or wireless private networks, and the network 104 may be a public network (e.g., the Internet) via which the clinical environment 102 and the cloud environment 106 communicate with each other. The cloud environment 106 may be a cloud-based platform configured to communicate with multiple clinical environments. The cloud environment 106 may include a collection of services, which are delivered via the network 104 as web services. The components of the cloud environment 106 are described in greater detail below with reference to FIG. 9.

Components of Clinical Environment

Figure 7:
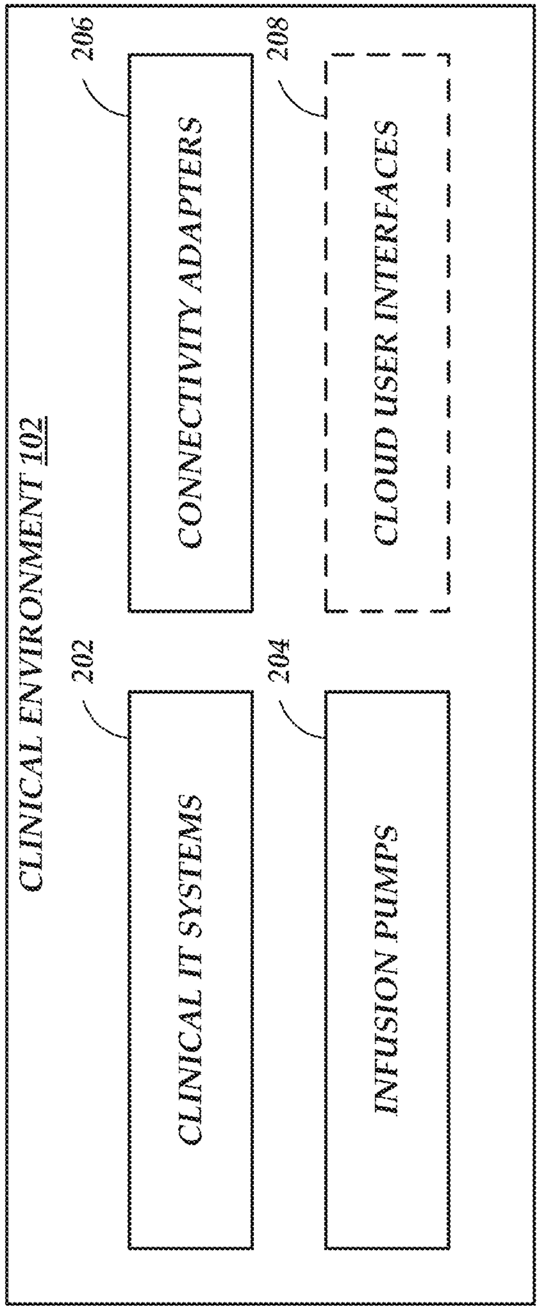
FIG. 7 is a block diagram illustrating example components of a clinical environment.

FIG. 7 illustrates the clinical environment 102, which includes one or more clinical IT systems 202, one or more infusion pumps 204, and one or more connectivity adapters 206. Further, the clinical environment 102 may be configured to provide cloud user interfaces 208 (e.g., generated and provided by the cloud environment 106). The clinical IT system 202 may include a hospital information system (HIS) designed to manage the facilities' operation, such as medical, administrative, financial, and legal issues and the corresponding processing of services. The infusion pump 204 is a medical device configured to deliver medication to a patient. The connectivity adapter 206 is a network component configured to communicate with other components of the clinical environment 102 and also communicate with the cloud environment 106 on behalf of the other components of the clinical environment 102. In some cases, the connectivity adapter 206 is a network appliance with limited storage space (e.g., memory and/or persistent storage). The cloud user interfaces 208 may be provided to a user in the clinical environment 102 via a browser application, desktop application, mobile application, and the like. The user may access status reports and other data stored in the cloud environment 106 via the cloud user interfaces 208.

The components 202-208 illustrated in FIG. 7 may communicate with one or more of the other components in the clinical environment 102. For example, each of the clinical IT system 202 and the infusion pump 204 may communicate with the connectivity adapter 206 via physical local area network (LAN) and/or virtual LAN (VLAN). The components 202-208 may communicate messages in the clinical environment 102 over a message channel of the local network and may communicate data in the clinical environment 102 over a data channel of the local network. Although not shown in FIG. 7, the clinical environment 102 may include other medical devices and non-medical devices that facilitate the operation of the clinical environment 102.

Overview of Messaging in the Clinical Environment

Figure 8:
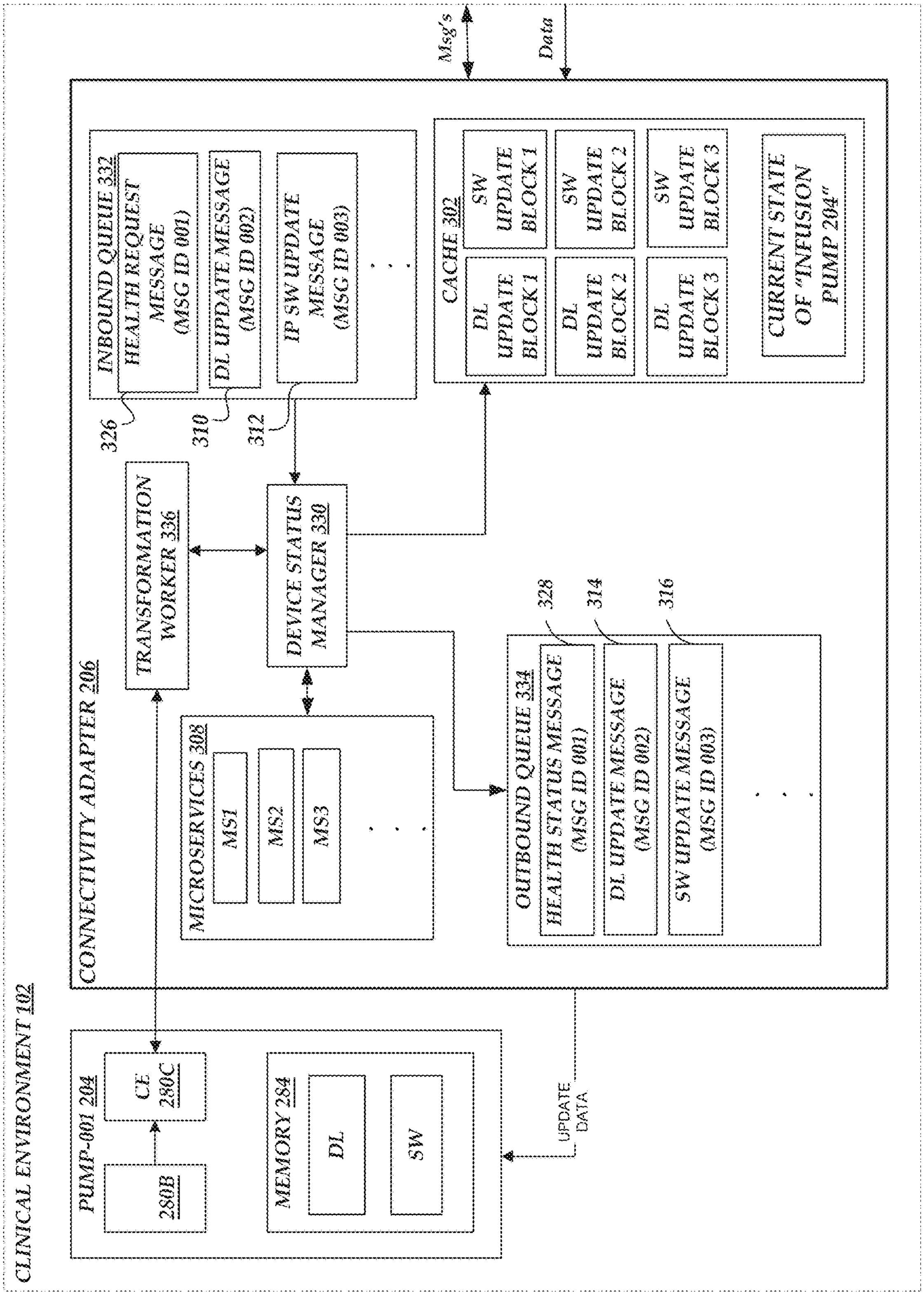
FIG. 8 is a schematic diagram illustrating example components of an infusion pump and a connectivity adapter of a clinical environment.

FIG. 8 illustrates example messages and data received, stored, and transmitted by the connectivity adapter 206 in the clinical environment 102. As shown in FIG. 8, the infusion pump 204 may include a processor 280B and a communication engine 280C, and memory 284 storing at least one or more drug libraries and operational software.

The drug libraries include boundaries for drug delivery for various medications that can be delivered to patients by infusion pumps. The operational software can include the operating system of the infusion pump, as well as other software for performing various functions. Each type of infusion pump and even different versions of the same type of infusion pump may operate with a different operating system.

The processor 280B may generate and send pump messages to the communication engine 280C for storage and transmission to the connectivity adapter 206. In some cases, the messages are each associated with a message ID. A message ID can be a unique identifier or a sequence identifier. The pump messages may include clinical information. The communication engine 280C may send such pump messages to the connectivity adapter 206. Pump messages sent to the connectivity adapter 206 via the communication engine 280C and generated by the processor 280B may be transformed by the transformation worker 336 into a standardized dataset message (e.g., message format used by the connectivity adapter 206 to communicate with the cloud environment 106, sometimes referred herein as simply a message).

The communication engine 280C may also receive messages from the connectivity adapter 206 indicating that updates, such as updates to the drug library or updates to the operational software are available and may send messages to the connectivity adapter 206 requesting the updates (e.g., update data). The communication engine 280C may also receive the update data from the connectivity adapter 206 for storage in the memory 284. The update data may be drug library update data or may be operational software update data. The operational software update may include one or more of a device configuration, a network configuration, certificate(s), language pack(s), software update images, software update patches, security updates, and the like. The update data may be provided over a different communication channel than the communication channel(s) used to send or receive messages.

As also shown in FIG. 8, the connectivity adapter 206 may include transformation worker 336, device status manager 330, cache 302, inbound queue 332, outbound queue 334, and microservices 308. The transformation worker 336 may transform the messages sent to the connectivity adapter 206 from the infusion pump 204 into the standardized dataset message. The transformation worker 336 may also transform messages sent from the connectivity adapter 206 to the infusion pump 204 into a message format usable by the infusion pump 204.

The microservices 308 include one or more programs (e.g., MS1, MS2, MS3 . . . ) that perform specific service functions within the operation of the connectivity adapter 206. For example, a microservice 308 may send the message to the outbound queue 334, while another microservice 308 may receive messages and place them into the inbound queue 332. In addition to performing service functions, one or more microservices 308 may monitor the characteristics of the service functions. For example, the microservice 308 may monitor parameters related to the execution of a service function, such as, for example, the size of a queue 332, 334 or other queue, latency, memory usage, CPU time, and the like. The connectivity adapter 206 may provide the parameters to the cloud environment 106 when one or more parameters exceed a threshold, or the connectivity adapter 206 may provide the parameters upon request from the cloud environment 106.

The inbound queue 332 receives and stores messages from the cloud environment 106 for processing by the connectivity adapter 206. For example, the inbound queue 332 may receive one or more of a health request message 326, a drug library update message 310, and an infusion pump software update message from the cloud environment 106. The health request message 326 may be a request for the health or the status of the connectivity adapter 206. The drug library update message 310 may be notification that a drug library update is available for a least a portion of the infusion pumps 204 associated with the connectivity adapter 206. An infusion pump software update message 312 may be a notification that an update to the operational software for at least a portion of the infusion pumps 204 associated with the connectivity adapter 206 is available. The connectivity adapter 206 may comprise more than one inbound queue such that, for example, there is at least an inbound queue 332 for messages received from the cloud environment 106 over the network 104 and at least another inbound queue for messages received from one or more infusion pumps 204 over the local network. The messages stored in the inbound queue 332 may be associated with one or more message identifiers (IDs). A message ID can be a unique identifier or a sequence identifier. The messages received from the cloud environment 106 may be sent over a message channel associated with the network 104.

The outbound queue 334 receives and stores messages to be sent from the connectivity adapter 206. For example, the outbound queue 334 may receive a health status message 328 to be sent to the cloud environment 106 over the network 104. The outbound queue 334 may also receive a drug library update message 314 and a software update message 316 to be sent to one more infusion pumps over the local network. The health status message 328 may be a message indicating the health of the connectivity adapter 206 and may include one or more parameters from the microservices 308. The drug library update message 314 may be a notification to one or more infusion pumps 204 that a drug library update is available. The software update message 316 may be a notification to one or more infusion pumps 204 that an update to the operational software is available. The connectivity adapter 206 may comprise more than one outbound queue such that, for example, there is at least an outbound queue 334 for messages to be sent to the cloud environment 106 over the network 104 and at least another outbound queue for messages to be sent to one or more infusion pumps 204 over the local network. The messages stored in the outbound queue 334 may be associated with one or more message identifiers (IDs). A message identifier can be a unique identifier or a sequence identifier. The messages sent from the connectivity adapter 206 to the infusion pumps 204 may be sent over a message channel associated with the local network.

The device status manager 330 receives the drug library and operational software updates from the cloud environment 106 and caches blocks of the update data in the cache 302. The device status manager 330 processes the received messages from the inbound queue 332 and sends messages to the outbound queue 334 for transmission to the cloud environment 106 or to the infusion pumps 204. The data received from the cloud environment 106 may be sent over a data channel associated with the network 104 and separate from the message channel of the network 104. Because the data channel in the cloud environment is separate from the message channel in the cloud environment, the data transfer does not interfere with the clinical messaging from the connectivity adapter to the cloud environment. The data sent from the cache 302 to the infusion pumps 204 may be sent over a data channel associated with the local network and separate from the message channel associated with the local network. Because the data channel in the local network is separate from the message channel in the local network, the data transfer does not interfere with the clinical messaging from infusion pumps to the connectivity adapter. Thus, congestion on both the message channel of the cloud environment and the message channel of the local network is reduced.

The device status manager 330 also processes transformed messages provided by the transformation worker 336 and merges the data included in the transformed messages into the cache 302 to update the current state of the infusion pump 204 stored in the cache 302. Additional details regarding the messaging in the clinical environment 102 are provided below.

Components of Cloud Environment

Figure 9:
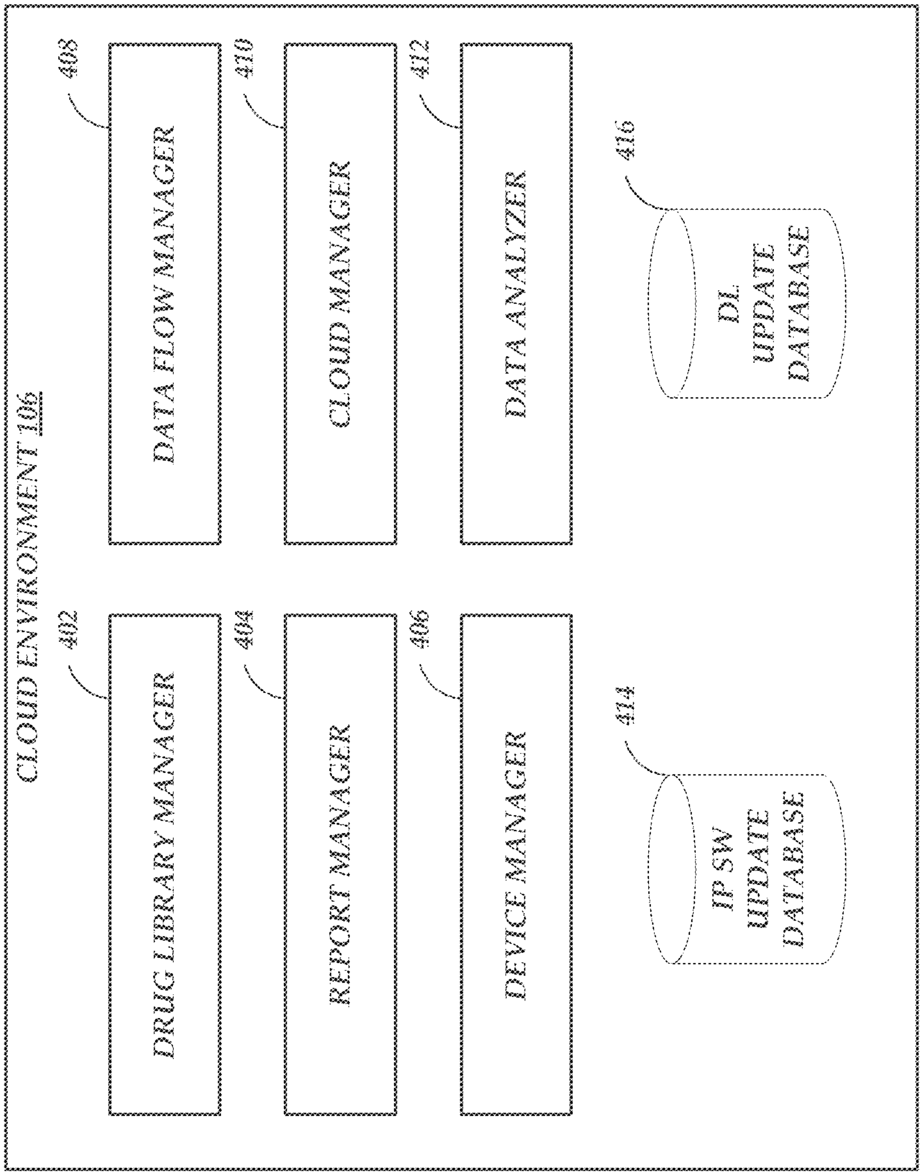
FIG. 9 is a block diagram illustrating example components of a cloud environment.

FIG. 9 illustrates an example of the cloud environment 106, which includes drug library manager (DLM) 402, report manager 404, device manager 406, data flow manager (DFM) 408, cloud manager (CM) 410, data analyzer (DA) 412, infusion pump (IP) software (SW) update database 414 and drug library update database 416.

The DLM 402 may provide a set of features and functions involved in the creation and management of drug libraries for use with infusion pumps. These drug libraries may provide user-defined settings for pump configuration and drug error reduction (DERS).

The report manager 404 may provide various reporting capabilities for clinically relevant infusion data which users can choose to use for further analysis, such as tracking and trending of clinical practices.

The device manager 406 may oversee and manage the maintenance of infusion pumps, providing users the capability to view and manage asset and operational data. For example, the device manager 406 may schedule drug library and software updates for infusion pumps.

The DFM 408 may facilitate storing, caching, and routing of data between compatible infusion pumps, medical network integration or safety software, and compatible external systems. For example, the DFM may store infusion and operational data received from infusion pumps, store and cache infusion pump drug libraries and software images, convert and route network messaging between the cloud environment 106 and the clinical environment 102, convert and route medication order information from a hospital information system to an infusion pump (e.g., auto-programming or smart-pump programming), and/or convert and route alert information and infusion events from infusion pumps to hospital information systems (e.g., alarm/alert forwarding, and auto-documentation, or infusion documentation).

The CM 410 may serve as a general-purpose computing platform for the other modules illustrated in FIG. 9. Functionally, the CM 410 may be similar to Microsoft Windows or Linux operating systems as it provides the following services: networking, computation, user administration and security, storage, and monitoring.

The DA 412 may provide data analytics tools for generating user interfaces and reports based on the data generated and/or received by the other modules illustrated in FIG. 9.

Operational software update database 414 may store operational software and/or updates to the operational software for one or more infusion pumps 204. Drug library update database 416 may store one or more drug libraries and/or updates to the one or more drug libraries that are used by the infusion pumps 204 to regulate aspects of drug delivery.

The databases 414, 416 may also store data generated and/or received by the modules 402-412 of the cloud environment 106. Although not illustrated in FIG. 9, the cloud environment 106 may provide other resources such as processors, memory, disk space, network, etc. The modules 402-412 may be hardware components configured to perform one or more of the techniques described herein. Alternatively, the modules 402-412 may be implemented using software instructions stored in physical storage and executed by one or more processors. Although illustrated as separate components, the modules 402-412 may be implemented as one or more hardware components (e.g., a single component, individual components, or any number of components), one or more software components (e.g., a single component, individual components, or any number of components), or any combination thereof.

The cloud environment 106 can be implemented using a commercial cloud services provider (e.g., Amazon Web Services®, Microsoft Azure®, Google Cloud®, and the like). The cloud environment 106 can be implemented using network infrastructure managed by the provider and/or developer of the modules 402-412 shown in FIG. 9. The features and services provided by one of more of the modules 402-412 may be implemented on one or more hardware computing devices as web services consumable via one or more communication networks. One of more of the modules 402-412 can be provided by one or more virtual machines implemented in a hosted computing environment. The hosted computing environment may include one or more rapidly provisioned and released computing resources, such as computing devices, networking devices, and/or storage devices.

Overview of Messaging in the Cloud Environment

Figure 10:
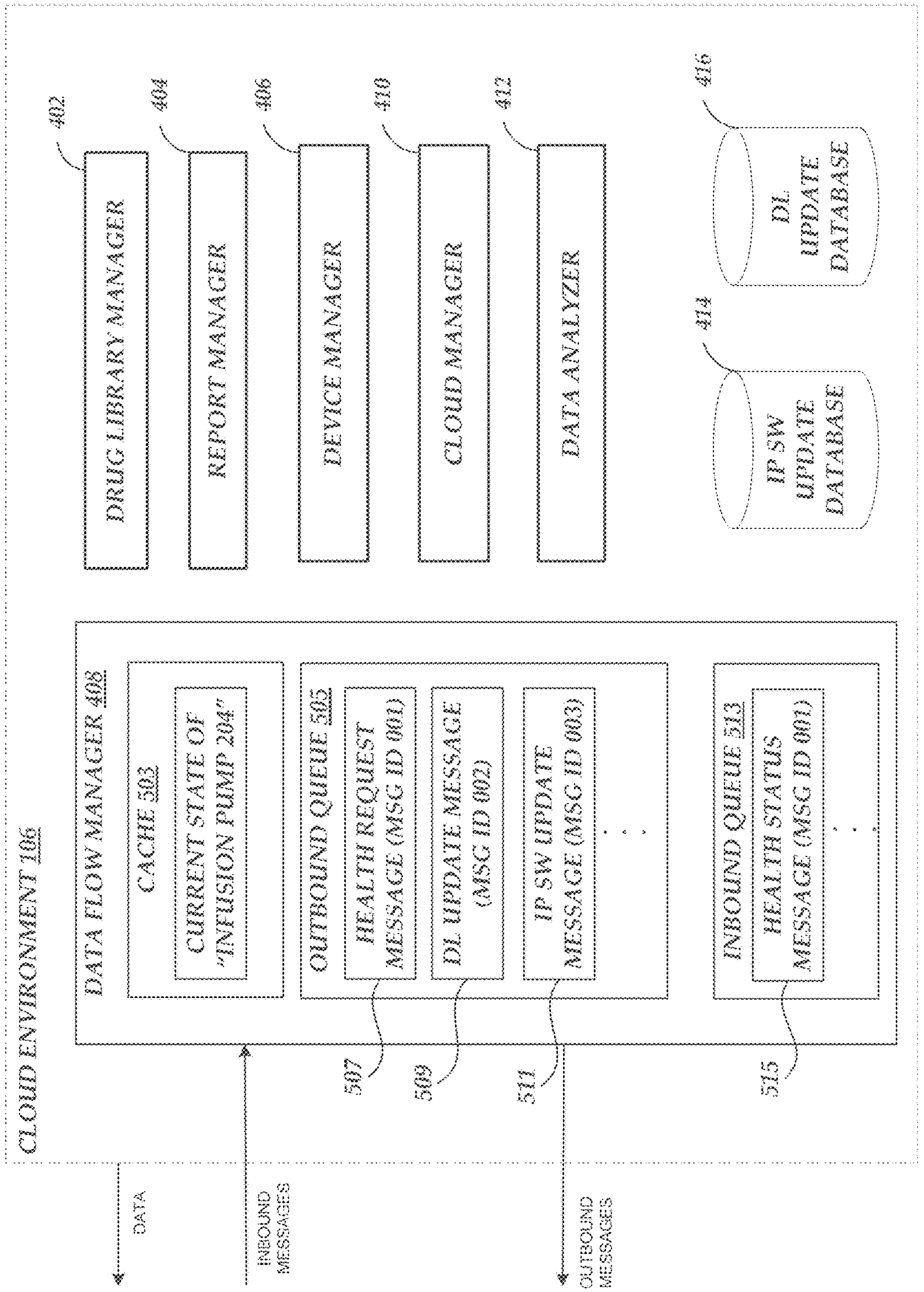
FIG. 10 is a schematic diagram illustrating example components of a data flow manager of a cloud environment.

FIG. 10 illustrates an example of how messages may be received, stored, and transmitted by the cloud environment 106. As shown in FIG. 10, the DFM 408 may include cache 503, outbound queue 505 and inbound queue 513. The outbound queue 505 may include messages to be transmitted to the clinical environment 102. For example, the outbound queue 505 can include a health request message 507, a drug library update message 509 providing a notification that a drug library update is available, and an infusion pump operational software update message 511 providing notification that an update to the infusion pump software is available. When these messages 507, 509, 511 are sent to the connectivity adapter 206, they are stored in the inbound queue 332 of the connectivity adapter 206 as messages 310, 312, respectively, shown in FIG. 8. In other examples, the outbound queue 505 may include command messages (e.g., instructions to update the security settings on the connectivity adapter 206), request messages (e.g., requests for missing messages for logging purposes), log requests, security updates, and the like.

The inbound queue 513 may include messages received from the clinical environment 102. In the example of FIG. 10, the inbound queue 513 includes a health status message 515 providing the status of the connectivity adapter 206. FIG. 8 illustrates the health status message 328 stored in the outbound queue 334 of the connectivity adapter 206 prior to it being sent to the cloud environment 206 and being stored in the inbound queue 513 of the data flow manager 408 as message 515. The inbound and outbound messages may be sent over a message channel of the network 104. The update data from the infusion pump software update database 414 and from the drug library update database 416 may be sent over a data channel of the network 104 that can be separate from the message channel of the network 104.

The cache 503 may store the current state of the infusion pump 204. In some cases, the current state stored in the cache 503 can be identical to the current state stored in the cache 302. In other cases, the current state stored in the cache 503 includes additional information not stored in the cache 302, or vice versa.

The process of reducing the transfer of drug library and operational software files from the cloud environment 106 to infusion pumps 204 is described in greater detail below with reference to FIGS. 11-13.

Infusion Pump Drug Library and Software Updates

Hospitals can have thousands of infusion pumps for infusing drugs to patients. Each infusion pump follows rules contained in drug libraries when delivering the drugs to patients. The rules provide boundaries and guidelines for infusion, such as for example, hard dosing limits, soft dosing limits, rates of infusion, etc., for a plurality of infusible drugs. Drug libraries are often updated with new drugs, drugs being infused in new areas of the facility (e.g., neonatal, ICU, NICU), new infusion treatments, and the like. It is desirable that the infusion pumps include drug library updates in order to maintain the highest level of care for patients.

Further, infusion pumps include operational software that controls pump operations. With a hospital or health care system, there may be many different types of infusion pumps, and each type of infusion pump may have different operational software. As with drug libraries, operational software is often updated. The updates may change software functionality or add additional features. It is also desirable that the infusion pumps run the latest software versions in order to maintain the highest level of care for patients.

In a historical infusion pump network and system, each infusion pump may need to access a hospital server and storage where the updates are stored and download drug library and operational software updates. This is time consuming, and the volume of network traffic created by potentially thousands of infusion pumps receiving updates can significantly slow down the hospital network, or significantly impact clinical workflows.

However, in an example pump network and system described herein, a connectivity adapter can download the drug library and operational software updates once from cloud-based storage and can distribute the updates to infusion pumps when the infusion pumps are available to receive the updates. This relieves network traffic to the server and to the storage storing the updates and reduces the computing time needed to update the infusion pumps over the historical infusion pump networks and systems.

The connectivity adapter can communicate with a plurality of infusion pumps. To reduce local network congestion between the plurality of infusion pumps and the connectivity adapter, the connectivity adapter can stagger blocks of the updates to the infusion pumps.

The connectivity adapter and the cloud environment can communicate over a first network. The first network is the network connection established between the connectivity adapter and the cloud. the first network has two channels: a first channel to receive the update command and a second channel to obtain the update data. The connectivity adapter and each of the plurality of infusion pumps communicate over a second network. The second network is a network connection established between an infusion pump and the connectivity adapter. The second network has two channels: a first channel to receive the update command and a second channel to obtain the update data (e.g., files). This pattern applies to each infusion pump attached to the connected adapter; therefore, there are multiple second network connections for the connectivity adapter.

The update data can be operational software only; drug library data only; or both operational software and drug library information. The user can initiate the update from the cloud environment. A message can be sent from the server in the cloud environment with the update URL that the connectivity adapter can then update to the local URL for use by the infusion pumps as described in greater detail below. Alternatively, the infusion pump can request if there is an update available. The message is routed to the server in the cloud environment. If an update exists, a message can be sent from the cloud environment with the update URL that the connectivity adapter can update to the local URL, in the same manner as when the update is initiated from the cloud environment.

So as to not flood the hospital network, the connectivity adapter can stagger the updates between the connectivity adapter and its connected devices, which can be infusion pumps, medication compounding devices, and the like. For example, connectivity adapter 1 and connectivity adapter 2 can each have 500 connected devices that need to have the update. Each connectivity adapter can schedule the update for a subset of the connected devices, such as for example, 100 devices at a time. The connectivity adapters can be within separate hospital networks.

In another example, connectivity adapter 1 and connectivity adapter 2 can each have 500 connected devices that need to have the update. Connectivity adapter 1 can notify the cloud environment that it can process up to 100 updates and connectivity adapter 2 is too busy to process any updates. The cloud server then schedules updates for 100 of the devices that are connected to connectivity adapter 1. Additionally, connectivity adapter 1 could opt to stagger the update with a subset of the 100 devices as described above.

In another example, connectivity adapter 1 and connectivity adapter 2 can each have 500 connected devices that need to have the update. Both connectivity adapters can exist on the same hospital network. So as to not flood the hospital network, the cloud server will limit the number of updates each connectivity adapter can service concurrently. For example, the cloud server can limit the number of concurrent updates to 100 connected devices, it can then schedule 60 updates for connectivity adapter 1 and 40 updates for connectivity adapter 2. As the updates complete, additional devices can be added such that there are no more than 100 connected devices being updates at a time on the hospital network.

The user, via a user interface, can specific a predetermined number of infusion pumps or connected devices to update. The system can specify a predetermined number of pumps based on network traffic. The system may portion this group into smaller portions. For example, the user may schedule an update for 1000 connected devices. The system can redistribute the predetermined number of connected devices to update in chunks of 100 connected devices. Example methods of staggering updates to the connected devices can be independently responding to requesting devices, staggering groups of connected devices to receive the updates, and staggering the blocks of update data.

The connectivity adapter can determine specific connected devices to receive a different subset of cached blocks during the download of the update data. In another example, each connected device to receive an update can be provided with a local URL which is the location of where to obtain the update data. The connected device then connects to the connectivity adapter independently of any other connected devices and streams the update data. Since each connected device can stream the update data independently, a first connected device in communication with the connectivity adapter could be block 100 while a second connected device could be streaming block 50 of the update. In another example the connectivity adapter can delay the start of the streaming to subsets of the requesting connected devices to reduce the network load. The connectivity adapter can request to deliver an update to the connected devices and each connected device can confirm to the connectivity adapter that it is ready or is not ready to receive an update.

Figure 11:
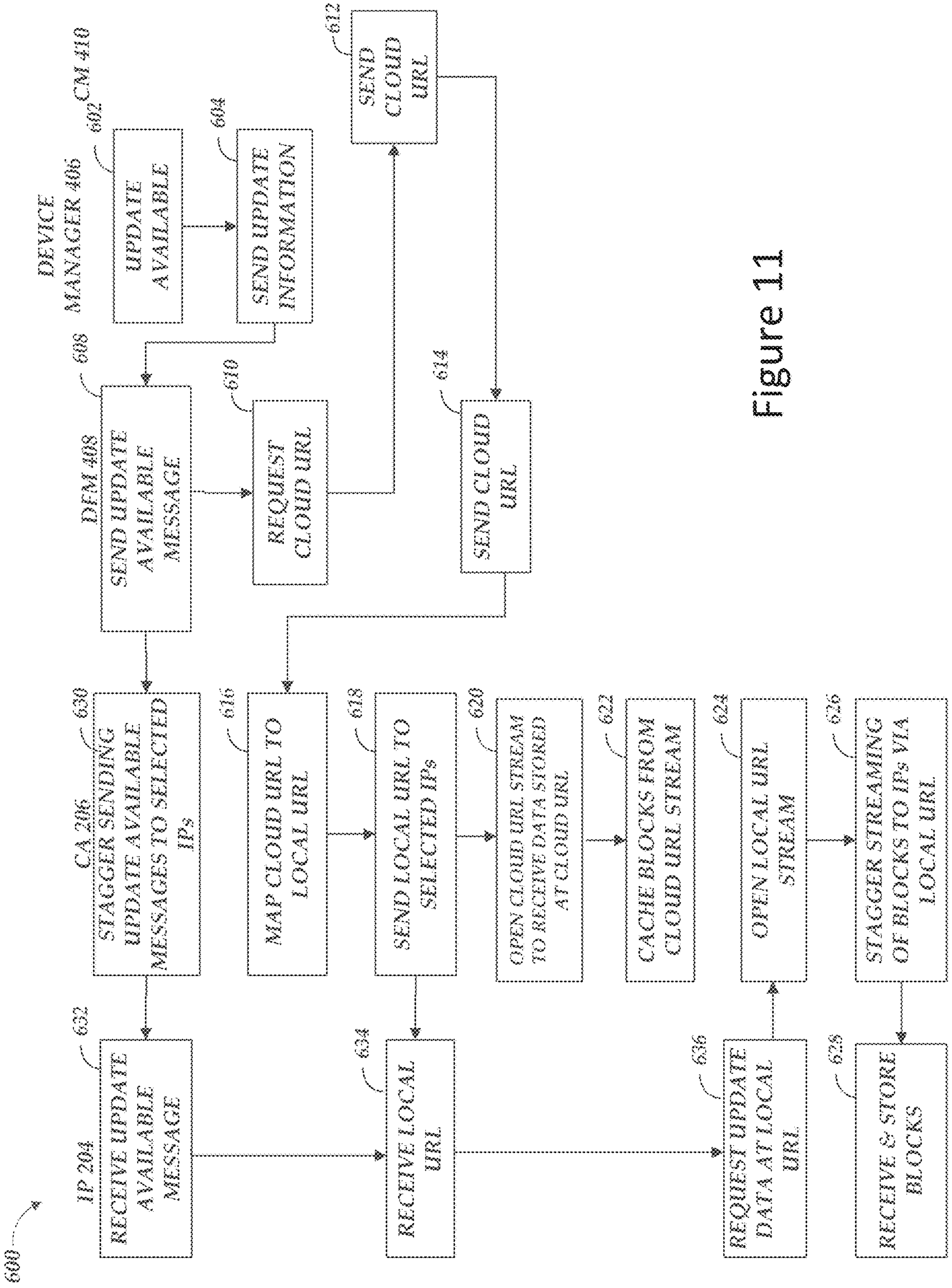
FIG. 11 is a block diagram illustrating an example system for reducing the transfer of drug library and operational software files to a plurality of infusion pumps.
Figure 12:
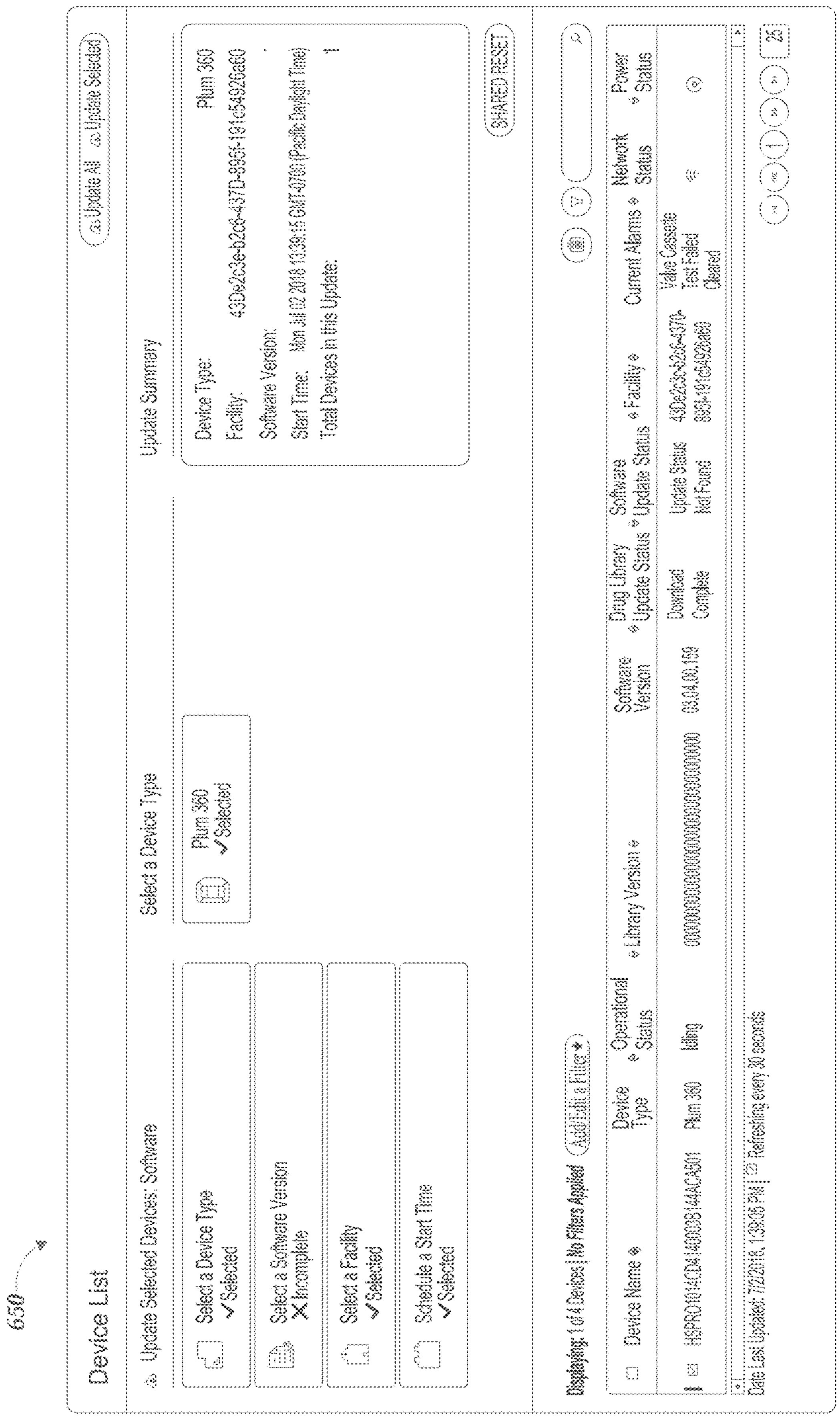
FIG. 12 illustrates an example user interface for scheduling a software update.

With reference to FIG. 11, an example system 600 for reducing the transfer of drug library and operational software update files to a plurality of infusion pumps (IPs) 204 is described in greater detail. The illustrated system 600 comprises the cloud manager (CM) 410, the device manager 406, the data flow manager (DFM) 408, one or more connectivity adapters (CA) 206, and one or more infusion pumps (IP) 204. The device manager 406 can interface with the user via the cloud user interface 208 (see FIG. 7). For example, the user loads the update data into the CM 410, logs into the device manager 406, and schedules an update for the infusion pumps 204 associated with the system. Scheduling the update includes providing the device manager 406 with update information. The device manager 406 detects the upload of the update data onto the CM 410 and stores the update record (e.g., a cloud URL). The update can be available immediately or can be scheduled for a future time. The update can be a drug library update 416 or the update can be an update of infusion pump operational software 414. The update is not bound by the connectivity adapter 206. Update information can specify one or more filters, such as, for example, specific infusion pumps 204 (e.g., update infusion pumps 1, 2, and 3), specific infusion pump versions (e.g., update all infusion pump operational software version 1.0 to version 1.1), the type(s) of infusion pumps 204 (e.g., update all type 0 infusion pumps 204), and/or the facilities associated with the infusion pumps 204 for which the update 414, 416 applies (e.g., update all infusion pumps 204 in facility XYZ, where XYZ is the facility identifier).

The process of reducing the transfer of drug library and operational software update files to a plurality of infusion pumps (IPs) 204 performed by the system 600 illustrates example algorithm(s) that may be programmed, using any suitable programming environment or language, to create machine code capable of execution by a CPU or microcontroller. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then then executed by the CPU or microcontroller. For example, when the process of reducing the transfer of drug library and operational software update files to a plurality of infusion pumps (IPs) 204 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. The process of reducing the transfer of drug library and operational software update files to a plurality of infusion pumps (IPs) 204 or portions thereof may be implemented on multiple processors, serially or in parallel.

At block 602, the device manager 406 can receive a message from the cloud user interface 208 that the user has scheduled an update. FIG. 12 illustrates an example user interface 650 for scheduling a software update. As shown, the user interface 650 includes fields for selecting a device type, selecting a software version, selecting a facility, and scheduling a start time. User interface 650 can provide an update summary and a device list.

At block 604, the device manager 406 can send the scheduled update information to the DFM 408. The DFM 408 can generate a unique key to identify the scheduled event, as scheduled by the user, for one or more pumps. The update information can include information pertaining to the type of update (e.g., drug library update 416 or operational software update 414), the scheduled availability of the update, the infusion pumps 204 to receive the update, the type of infusion pump 204 to receive the update, facility identifiers, and other associated identifiers. The DFM 408 can wait until the scheduled time to notify the connectivity adapter 206 that the update is available. The DFM 408 can notify the connectivity adapter 206 of the scheduled update and the connectivity adapter 206 can wait until the scheduled time to notify the infusion pumps 204 that the update is available.

The DFM 408 can receive the update information from the device manager 406. At block 608, the DFM 408 can send a message to one or more connectivity adapters 206 indicating that an update is available. The message can be one of the drug library (DL) update message 509 or the infusion pump (IP) software (SW) update message 511. The message can be send over the cloud message channel.

At block 610, the DFM 408 can request a cloud URL from the CM 410. The cloud URL can be the location within the cloud environment 106 storing the update 414, 416. The cloud URL can be a temporary URL having a defined lifetime. At block 612, the CM 410 can send the cloud URL to the DFM 408. At block 614, the DFM 408 can send the cloud URL to the connectivity adapter 206. The cloud URL can be sent over the cloud data channel.

The connectivity adapter 206 can receive the message indicating that an update is available and the cloud URL from the DFM 408. The received message can be one of the DL update message 310 or the IP SW update message 312.

At block 630, the connectivity adapter 206 can send a message to the selected infusion pumps 204 that an update is available. The connectivity adapter 206 can stagger the update notifications to the selected infusion pumps 204. For example, if 100 infusion pumps 204 are scheduled to receive an update, the connectivity adapter 206 may only notify 50 infusion pumps 204 and as individual update downloads complete new updates are scheduled for the remaining infusion pumps 204. The message can be one of the DL update message 314 or the IP SW update message 316. The message can be sent over the local message channel. The selected infusion pumps 204 can be the infusion pumps intended to receive the drug library or operational software update.

At block 616, the connectivity adapter 206 can create a local URL and maps the cloud URL to the local URL. The local URL can be a URL identifying a location in the connectivity adapter 206 within the clinical environment 102. At block 618, the connectivity adapter 206 can send the local URL to the infusion pumps 204 identified in the update available message. The local URL can be sent over the local data channel.

At block 620, the connectivity adapter 206 can open a cloud URL stream to receive the update data stored at the cloud URL. The update data can be streamed from storage 414, 416 at the cloud URL over the cloud data channel. The messaging between the connectivity adapter 206 and the DFM 408 can occur on the cloud message channel that is separate from the cloud data channel. Thus, the cloud data channel can solve the problem of data packet prioritization because the data streaming, which is occurring on a separate channel, does not interfere with the infusion pump clinical messaging. Further, the cloud data channel can strengthen and simplify the security of the network by allowing the infusion pumps 204 to receive data over a secured isolated virtual local network (VLAN) that is not exposed to public networks. Advantageously, the infusion pumps 204 can request and receive the update data from the connectivity adapter 206 should the network connection between the connectivity adapter 206 and cloud environment 106 become unavailable because the updates are stored at the connectivity adapter 206.

The connectivity adapter 206 can be pre-notified of an available update, stream the update data before the scheduled update time, and notify the infusion pumps 204 of the available update at the scheduled time. This can also provide the advantage of being able to update the infusion pumps 204 at the scheduled update time should the network connection with the cloud environment 106 become unavailable at the scheduled update time.

At block 622, the connectivity adapter 206 can cache blocks of the streaming update data in the cache 302. The connectivity adapter 206 can associate data in the cache 302 with the local URL. Once the update is stored in the cache 302 at the connectivity adapter 206, the cloud data channel between the connectivity adapter 206 and the DFM 408 may no longer be needed. This can reduce network activity as the cloud environment 106 does not need to be accessed to individually update each infusion pump 204.

At block 632, the selected infusion pumps 204 can receive the message 314, 316 from the connectivity adapter 206 that an update is available. At block 634, the infusion pumps 204 can receive the local URL from the connectivity adapter 206.

At block 636, the selected infusion pumps 204 can request the update data at the local URL from the connectivity adapter 206. The request can include an HTTP multi-part GET request. Each infusion pump 204 can request the update data when it is available to receive the update data.

The update data from the connectivity adapter 206 to the infusion pump 204 can be streamed over the local data channel within the local network. The messaging between the connectivity adapter 206 and the infusion pumps 204 can occur over the local message channel that is separate from the local data channel. Thus, the local data channel within the local or hospital network can also solve the problem of data packet prioritization because the data streaming, which is occurring on a separate channel does not interfere with the clinical infusion pump messaging on the local message channel. Another advantage of separating the messages and the data onto a local message channel and a local data channel, respectively, can be allowing the infusion pump communication engine 280C to actively download into its storage 284 large files, which can be, for example, 300 MBs or more, without interrupting the infusion pump processor 280B, which is performing clinical functions. Once the clinical functions are complete, the user can initiate the update without waiting for the update data to be downloaded.

At block 624, the connectivity adapter 206 can open the local URL stream. At block 626, the connectivity adapter 206 can stagger streaming of the blocks of update data via the local URL. The connectivity adapter 206 can stagger the update data in blocks by independently responding to requests from the group of infusion pumps 204. For example, infusion pump 204A can be downloading block five and infusion pump 204B can be downloading block seven from the local URL cache 302, while the connectivity adapter 206 can be downloading block ten from the cloud URL.

As described above at block 630, the connectivity adapter 206 can stagger update notifications to the infusion pumps 204. For example, if 100 infusion pumps 204 are scheduled to receive an update, the connectivity adapter 206 may only notify 50 infusion pumps 204 and as individual update downloads complete new updates are scheduled for the remaining infusion pumps 204.

The infusion pumps 204 can also include functionality to avoid network slowdowns. The infusion pumps 204 can check within its memory 284 to determine whether the available update is already there. If the update is available, the infusion pump 204 may not request the update. The infusion pump 204 can check within its memory 284, for example, to determine whether another update is already pending. If another update is pending, the infusion pump 204 may not request the update. The system 600 may not permit a drug library update and an operational software update to occur at the same or near to the same time.

The infusion pump 204 can utilize an exponential backoff procedure when requesting the update data from the connectivity adapter 206. For example, when the request from the infusion pump 204 for the update data is unfilled or ignored, the infusion pump 204 can re-request the update data according to a process, such as an exponential backoff process to prevent network congestion. In an exponential backoff process, the rate at which the infusion pump 204 sends the re-requests can be decreased gradually in order to find an acceptable request rate. The infusion pump 204 can re-request the update data randomly to prevent network congestion.

At block 628, the infusion pump 204 can receive and store the blocks of update data in the memory 284. As discussed above, the update data can be an updated or new drug library, updated operational software for the infusion pump 204, which may include one or more of application software, language packs, security updates, and device configuration, digital certificates, and/or the like.

The infusion pump 204 can initiate the request to the connectivity adapter 206 for update data, such as an updated drug library, without being notified of an available update. For example, the infusion pump 204 can send a request to the connectivity adapter 206 for a known missing drug library, or to ask if an update is available. The connectivity adapter 206 can store a plurality of drug libraries, including historical versions of drug libraries.

Figure 13:
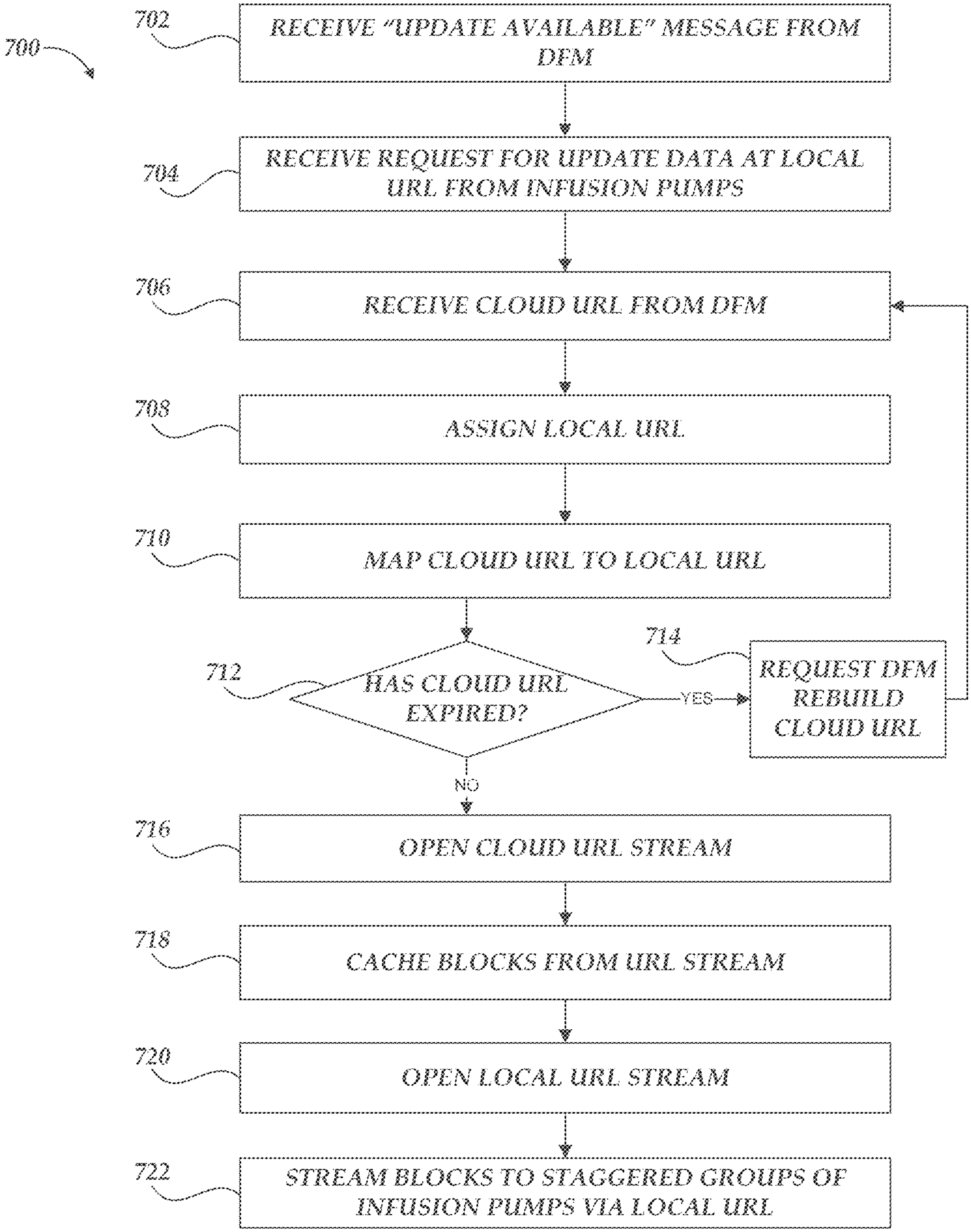
FIG. 13 is a flow chart of an example process to reduce the transfer of drug library and operational software files to a plurality of infusion pumps.

With reference to FIG. 13, an example process 700 to reduce the transfer of drug library and operational software files to a plurality of infusion pumps 204 is described in greater detail. The process 700 illustrates an example algorithm that may be programmed, using any suitable programming environment or language, to create machine code capable of execution by a CPU or microcontroller. Various embodiments may be coded using assembly, C, OBJEC- TIVE-C, C++, JAVA, or other human-readable languages and then compiled, assembled, or otherwise transformed into machine code that can be loaded into read-only memory (ROM), erasable programmable read-only memory (EPROM), or other recordable memory that is coupled to the CPU or microcontroller and then then executed by the CPU or microcontroller. For example, when the process 700 is initiated, a set of executable program instructions stored on one or more non-transitory computer-readable media (e.g., hard drive, flash memory, removable media, etc.) may be loaded into memory (e.g., random access memory or "RAM") of a computing device of the clinical environment 102 and/or the cloud environment 106. The executable instructions may then be executed by a hardware-based computer processor (e.g., a central processing unit or "CPU") of the computing device. The process 700 or portions thereof may be implemented on multiple processors, serially or in parallel. For convenience, the steps of the example process 700 are described as being performed by the connectivity adapter 206.

At block 702, the connectivity adapter 206 can receive the drug library update message 310 or the infusion pump operational software update message 312.

The connectivity adapter 206 can notify the infusion pumps 204 that an update is available at the local URL. The connectivity adapter 206 can send a drug library update message 314 or a software update message 316 over the local message channel associated with the local network. The connectivity adapter 206 can stagger notifying the infusion pumps 204 by notifying a portion of the selected infusion pumps 204 and notifying subsequent portion of the selected infusion pumps 204 as individual update downloads complete.

At block 704, the connectivity adapter 206 can receive request(s) from the infusion pump(s) 204 for the update data at the local URL.

At block 706, the connectivity adapter 206 can receive the cloud URL from the DFM 408. The cloud URL can have an expiration time.

At block 708, the connectivity adapter 206 can assign a local URL. The connectivity adapter 206 can create the local URL. At block 710, the connectivity adapter 206 can map the cloud URL to the local URL.

At block 712, the connectivity adapter 206 can determine whether the cloud URL has expired. If the cloud URL is active, the process 700 can move to block 716.

If the cloud URL has expired, the process can move to block 714. At block 714, the connectivity adapter 206 can request that the DFM 408 rebuild the cloud URL. The DFM can determine a new cloud URL and can send the new cloud URL to the connectivity adapter 206. The process 700 can move to block 704 and repeat blocks 704-712 for the new cloud URL.

At block 716, the connectivity adapter 206 can open the cloud URL stream and at block 718, can cache the blocks of update data from the URL stream over the cloud data channel associated with the network 104.

At block 720, in response to receiving requests for the update data from the infusion pumps 204, the connectivity adapter 206 can open the local URL stream. At block 722, the connectivity adapter 206 can stream blocks of update data to staggered groups of infusion pumps 204. The blocks of update data can be streamed over the local data channel to the infusion pumps 204. Staggering can be performed in a variety of ways. For example, the connectivity adapter 206 can stream blocks of data in parallel to a small group of infusion pumps 204. If the infusion pump's initial request for data is rejected or ignored, the infusion pumps 204 can re-request the update data at a rate as determined by an exponential backoff process.

As described above, the updates can include operational software updates or drug library updates. The receiving and storing of the blocks of update data can occur in the background when the infusion pump 204 is operating. However, the installation and running of the updates can occur under controlled conditions, such as when the infusion pump 204 is not being used to infuse medication to patients.

Terminology and Conclusion

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in this description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single disclosed embodiment.

Embodiments of the disclosed systems and methods may be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules but may be represented in hardware and/or firmware. Moreover, although in some embodiments a module may be separately compiled, in other embodiments a module may represent a subset of instructions of a separately compiled program and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

A number of applications, publications, and external documents may be incorporated by reference herein. Any conflict or contradiction between a statement in the body text of this specification and a statement in any of the incorporated documents is to be resolved in favor of the statement in the body text.

Terms of equality and inequality (e.g., less than, greater than) are used herein as commonly used in the field, e.g., accounting for uncertainties present in measurement and control systems. Thus, such terms can be read as approximately equal, approximate less than, and/or approximately greater than. In other aspects of the invention, an acceptable threshold of deviation or hysteresis can be established by the pump manufacturer, the editor of the drug library, or the user of a pump.

While the embodiments of the invention disclosed herein are presently considered to be preferred, various changes and modifications can be made without departing from the scope of the invention. Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above. The scope of the invention is indicated in the appended claims, and all changes that come within the meaning and range of equivalents are intended to be embraced therein.

What is claimed is:

1. A method of automatically updating software stored on an infusion pump, the method comprising:

waking a processor within the infusion pump from an infusion pump off state, while maintaining a communication engine within the infusion pump in a communication engine off state;

while the communication engine remains in the communication engine off state, determining that the infusion pump is receiving electrical power from a battery coupled to the infusion pump;

while the communication engine remains in the communication engine off state, and before determining whether an update is available, determining that the battery contains sufficient energy to complete a system software or drug library update;

in response to and subsequent to determining that the battery contains sufficient energy to complete the system software or drug library update waking the communication engine within the infusion pump from the communication engine off state; and communicating with a server over a network, using the communication engine, to determine whether the update is available to be acquired from a remote location.

2. The method of claim 1, further comprising:

determining that the update is not available; and causing the communication engine to return to the communication engine off state; and causing the processor to return to the infusion pump off state.

3. The method of claim 1, further comprising:

determining that the update is available;

acquiring the update; and updating the infusion pump with the update.

4. The method of claim 3, wherein acquiring the update comprises receiving the update via a wired or wireless network.

5. The method of claim 3, wherein the update comprises an operating software update.

6. The method of claim 5, further comprising installing the operating software update.

7. The method of claim 3, wherein the update comprises a drug library update.

8. The method of claim 1, wherein waking the processor comprises waking the processor a predetermined number of times during a predetermined period.

9. The method of claim 8, wherein the predetermined number of times is one of one, two, three, or four times, and the predetermined period is a day.

10. The method of claim 1, wherein the processor receives no electrical power while in the infusion pump off state.

11. An infusion pump configured to automatically determine whether to receive an update, comprising:

a battery;

a processor configured to receive power from the battery;

a communication engine in communication with the processor and configured to communicate with a remote location;

a memory in communication with the processor and storing instructions that when executed by the processor configure the processor to:

wake the processor from an infusion pump off state while maintaining the communication in a communication engine off state;

while the communication engine remains in the communication engine off state, determine that the infusion pump is receiving electrical power from the battery;

while the communication engine remains in the communication engine off state, and before determining whether an update is available, determine whether the battery contains sufficient energy to complete a system software or drug library update; and in response to and subsequent to determining that the battery contains sufficient energy to complete the system software or drug library update, wake the communication engine from the communication engine off state;

communicate with a server over a network, using the communication engine, to determine whether the update is available to be acquired from the remote location; and a clock in communication with the processor and configured to: (a) wake the processor from the infusion pump off state in response to an alarm signal generated by the clock; and (b) cause the processor to execute the instructions in response to the alarm signal.

12. The infusion pump of claim 11, wherein the processor receives no electrical power while in the infusion pump off state.

13. The infusion pump of claim 11, wherein the instructions further enable the processor to determine that the update is not available, and in response to determining that the update is not available, cause the communication engine to return to the communication off state and the processor to return to the infusion pump off state.

14. The infusion pump of claim 11, wherein the instructions further enable the processor to determine that the update is available, and in response to determining that the update is available, cause the communication engine to acquire the update, and cause the processor to update the infusion pump with the update.

15. The infusion pump of claim 14, wherein the instructions cause the communication engine to acquire the update by receiving the update via a wired or wireless network.

16. The infusion pump of claim 14, wherein the update comprises an operating software update and wherein the instructions cause the processor to update the infusion pump by installing the operating software update on the infusion pump.

17. The infusion pump of claim 14, wherein the update comprises a drug library update, and wherein the instructions cause the processor to update the infusion pump by storing the drug library update within the infusion pump.

18. The infusion pump of claim 11, wherein the instructions further enable the processor to, in response to determining that the battery is not storing enough energy to acquire the update and update the infusion pump with the update, cause the infusion pump to return to the infusion pump off state.

19. The infusion pump of claim 11, wherein the instructions are configured to wake the processor by waking the processor a predetermined number of times during a predetermined period.

20. The infusion pump of claim 19, wherein the predetermined number of times is one of one, two, three, or four times, and the predetermined period is a day.

* * * * *